United States Patent
Bretschneider et al.

(10) Patent No.: US 8,859,466 B2
(45) Date of Patent: Oct. 14, 2014

(54) OXASPIROCYCLIC SPIRO-SUBSTITUTED TETRAMIC ACID AND TETRONIC ACID DERIVATIVES

(75) Inventors: Thomas Bretschneider, Lohmar (DE); Reiner Fischer, Monheim (DE); Gudrun Lange, Kelkheim (DE); Stefan Lehr, Liederbach (DE); Christian Arnold, Langenfeld (DE); Dieter Feucht, Eschborn (DE); Eva-Maria Franken, Limonest (FR); Martin Jeffrey Hills, Idstein (DE); Heinz Kehne, Hofheim (DE); Olga Malsam, Rösrath (DE); Christopher Hugh Rosinger, Hofheim (DE); Jan Dittgen, Frankfurt (DE); Ulrich Görgens, Ratingen (DE); Isolde Häuser-Hahn, Leverkusen (DE)

(73) Assignee: Bayer CropScience AG, Monheim (DE)

( * ) Notice: Subject to any disclaimer, the term of this patent is extended or adjusted under 35 U.S.C. 154(b) by 1292 days.

(21) Appl. No.: 12/671,548

(22) PCT Filed: Jul. 22, 2008

(86) PCT No.: PCT/EP2008/005973
§ 371 (c)(1),
(2), (4) Date: May 10, 2011

(87) PCT Pub. No.: WO2009/015801
PCT Pub. Date: Feb. 5, 2009

(65) Prior Publication Data
US 2011/0263424 A1    Oct. 27, 2011

(30) Foreign Application Priority Data

Aug. 2, 2007    (EP) .................................... 07113674

(51) Int. Cl.
| | | |
|---|---|---|
| C07D 491/107 | (2006.01) |
| A61K 31/4025 | (2006.01) |
| A01N 43/36 | (2006.01) |
| C07D 493/10 | (2006.01) |
| C07D 491/10 | (2006.01) |
| C07D 307/94 | (2006.01) |

(52) U.S. Cl.
CPC ............ *C07D 493/10* (2013.01); *C07D 491/10* (2013.01); *C07D 307/94* (2013.01)
USPC ............................. 504/283; 514/409; 548/408

(58) Field of Classification Search
None
See application file for complete search history.

(56) References Cited

U.S. PATENT DOCUMENTS

| | | | |
|---|---|---|---|
| 2,842,476 A | 7/1958 | Schreiber et al. |
| 4,021,224 A | 5/1977 | Pallos et al. |
| 4,186,130 A | 1/1980 | Teach |
| 4,438,130 A | 3/1984 | Kaplan |
| 4,525,201 A | 6/1985 | Kollmeyer et al. |
| 4,623,727 A | 11/1986 | Hubele |
| 4,639,266 A | 1/1987 | Heubach et al. |
| 4,844,734 A | 7/1989 | Iwasaki et al. |
| 4,881,966 A | 11/1989 | Nyffeler et al. |
| 4,888,049 A | 12/1989 | Iwasaki et al. |
| 4,891,057 A | 1/1990 | Sohn et al. |
| 4,902,340 A | 2/1990 | Hubele |
| 4,985,063 A | 1/1991 | Fischer et al. |
| 5,045,560 A | 9/1991 | Fischer et al. |
| 5,116,836 A | 5/1992 | Fischer et al. |
| 5,216,159 A | 6/1993 | Thurkauf et al. |
| 5,225,434 A | 7/1993 | Bertram et al. |
| 5,258,527 A | 11/1993 | Krauskopf et al. |
| 5,262,383 A | 11/1993 | Fischer et al. |
| 5,286,860 A | 2/1994 | Blum et al. |
| 5,314,863 A | 5/1994 | Loher et al. |

(Continued)

FOREIGN PATENT DOCUMENTS

| | | |
|---|---|---|
| AU | 2003206693 A1 | 7/2003 |
| CA | 1 162 071 A1 | 2/1984 |

(Continued)

OTHER PUBLICATIONS

English language translation of WO 2008/067873 A1 cited as FP103 (2008).

(Continued)

*Primary Examiner* — Michael Barker
(74) *Attorney, Agent, or Firm* — Sterne, Kessler, Goldstein & Fox P.L.L.C.

(57) ABSTRACT

The present invention relates to novel oxaspirocyclic spirophenyl-substituted tetramic acid and tetronic acid derivatives of the formula (I)

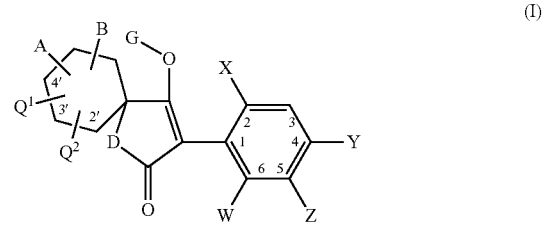

in which
W, X, Y, Z, A, B, D, $Q^1$, $Q^2$, and G have the meanings given above,
to a plurality of processes for their preparation and to their use as pesticides and/or herbicides. The invention also provides selective herbicidal compositions comprising, firstly, oxaspirocyclic spirophenyl-substituted tetramic acid and tetronic acid derivatives and, secondly, a crop plant compatibility-improving compound.
The invention furthermore relates to increasing the activity of crop protection compositions comprising compounds of the formula (I) by addition of ammonium salts or phosphonium salts and, if appropriate, penetrants.

11 Claims, No Drawings

(56) References Cited

U.S. PATENT DOCUMENTS

| | | | |
|---|---|---|---|
| 5,380,852 A | 1/1995 | Schutze et al. |
| 5,401,700 A | 3/1995 | Sohn et al. |
| 5,407,897 A | 4/1995 | Cary et al. |
| 5,462,912 A | 10/1995 | Hioki et al. |
| 5,462,913 A | 10/1995 | Fischer et al. |
| 5,504,057 A | 4/1996 | Fischer et al. |
| 5,508,436 A | 4/1996 | Fischer et al. |
| 5,516,750 A | 5/1996 | Willms et al. |
| 5,538,937 A | 7/1996 | Hasebe et al. |
| 5,567,671 A | 10/1996 | Fischer et al. |
| 5,589,469 A | 12/1996 | Fischer et al. |
| 5,610,122 A | 3/1997 | Fischer et al. |
| 5,622,917 A | 4/1997 | Fischer et al. |
| 5,683,965 A | 11/1997 | Bachmann et al. |
| 5,700,758 A | 12/1997 | Rosch et al. |
| 5,705,476 A | 1/1998 | Hoffarth |
| 5,739,079 A | 4/1998 | Holdgrun et al. |
| 5,792,755 A | 8/1998 | Sagenmuller et al. |
| 5,811,374 A | 9/1998 | Bertram et al. |
| 5,830,825 A | 11/1998 | Fischer et al. |
| 5,830,826 A | 11/1998 | Fischer et al. |
| 5,994,274 A | 11/1999 | Fischer et al. |
| 6,110,872 A | 8/2000 | Lieb et al. |
| 6,114,374 A | 9/2000 | Lieb et al. |
| 6,133,296 A | 10/2000 | Lieb et al. |
| 6,140,358 A | 10/2000 | Lieb et al. |
| 6,200,932 B1 | 3/2001 | Fischer et al. |
| 6,235,680 B1 | 5/2001 | Ziemer et al. |
| 6,251,827 B1 | 6/2001 | Ziemer et al. |
| 6,288,102 B1 | 9/2001 | Hagemann et al. |
| 6,316,486 B1 | 11/2001 | Lieb et al. |
| 6,358,887 B1 | 3/2002 | Fischer et al. |
| 6,417,370 B1 | 7/2002 | Lieb et al. |
| 6,451,843 B1 | 9/2002 | Lieb et al. |
| 6,458,965 B1 | 10/2002 | Lieb et al. |
| 6,472,419 B1 | 10/2002 | Fischer et al. |
| 6,511,940 B1 | 1/2003 | Ziemer et al. |
| 6,589,976 B1 | 7/2003 | Fischer et al. |
| 6,602,823 B1 | 8/2003 | Rochling et al. |
| 6,608,211 B1 | 8/2003 | Hagemann et al. |
| 6,645,914 B1 | 11/2003 | Woznica et al. |
| 6,861,391 B1 | 3/2005 | Fischer et al. |
| 6,894,005 B1 | 5/2005 | Maetzke et al. |
| 2002/0013341 A1 | 1/2002 | Duan et al. |
| 2003/0216260 A1 | 11/2003 | Ruther et al. |
| 2003/0224939 A1 | 12/2003 | Miles |
| 2004/0072802 A1 | 4/2004 | Duan et al. |
| 2005/0009880 A1 | 1/2005 | Cottrell et al. |
| 2005/0054535 A1 | 3/2005 | Fischer et al. |
| 2005/0090399 A1 | 4/2005 | Friedmann et al. |
| 2005/0096386 A1 | 5/2005 | Cottrell et al. |
| 2005/0261501 A1 | 11/2005 | De Nanteuil et al. |
| 2006/0160847 A1 | 7/2006 | Fischer et al. |
| 2006/0166829 A1 | 7/2006 | Fischer et al. |
| 2007/0015664 A1 | 1/2007 | Fischer et al. |
| 2007/0032539 A1 | 2/2007 | Himmler |
| 2007/0129252 A1 | 6/2007 | Fischer et al. |
| 2007/0225167 A1 | 9/2007 | Fischer et al. |
| 2007/0225170 A1 | 9/2007 | Fischer et al. |
| 2007/0244007 A1 | 10/2007 | Fischer et al. |
| 2007/0275858 A1 | 11/2007 | Fischer et al. |
| 2007/0298968 A1 | 12/2007 | Bretschneider et al. |
| 2007/0298969 A1 | 12/2007 | Fischer et al. |
| 2008/0167188 A1 | 7/2008 | Fischer et al. |
| 2008/0220973 A1 | 9/2008 | Fischer et al. |
| 2008/0305955 A1 | 12/2008 | Bretschneider et al. |
| 2008/0318776 A1 | 12/2008 | Fischer et al. |
| 2009/0029858 A1 | 1/2009 | Fischer et al. |
| 2009/0209513 A1 | 8/2009 | Fischer et al. |
| 2009/0215624 A1 | 8/2009 | Fischer et al. |
| 2009/0227563 A1 | 9/2009 | Fischer et al. |
| 2009/0239906 A1 | 9/2009 | Fischer et al. |
| 2009/0298828 A1 | 12/2009 | Fischer et al. |
| 2009/0305891 A1 | 12/2009 | Fischer et al. |
| 2010/0004127 A1 | 1/2010 | Fischer et al. |
| 2010/0009850 A1 | 1/2010 | Fischer et al. |

FOREIGN PATENT DOCUMENTS

| | | |
|---|---|---|
| CA | 2 671 179 A1 | 6/2008 |
| DE | 2 218 097 A1 | 11/1972 |
| DE | 2 350 547 A1 | 4/1974 |
| DE | 3 241 933 A1 | 5/1983 |
| DE | 196 21 522 A1 | 12/1997 |
| DE | 10 2005 059 8 | 6/2007 |
| DE | 10 2006 007 8 | 8/2007 |
| DE | 10 2006 050 1 | 4/2008 |
| DE | 10 2006 057 0 | 6/2008 |
| DE | 10 2007 001 8 | 7/2008 |
| EP | 0 036 106 A2 | 9/1981 |
| EP | 0 086 750 A2 | 8/1983 |
| EP | 0 094 349 A2 | 11/1983 |
| EP | 0 174 562 A2 | 3/1986 |
| EP | 0 191 736 A2 | 8/1986 |
| EP | 0 262 399 A2 | 4/1988 |
| EP | 0 269 806 A1 | 6/1988 |
| EP | 0 333 131 A1 | 9/1989 |
| EP | 0 346 620 A1 | 12/1989 |
| EP | 0 355 599 A1 | 2/1990 |
| EP | 0 377 893 A2 | 7/1990 |
| EP | 0 415 211 A2 | 3/1991 |
| EP | 0 442 073 A2 | 8/1991 |
| EP | 0 442 077 A2 | 8/1991 |
| EP | 0 453 086 A2 | 10/1991 |
| EP | 0 456 063 A2 | 11/1991 |
| EP | 0 492 366 A2 | 7/1992 |
| EP | 0 521 334 A1 | 1/1993 |
| EP | 0 528 156 A1 | 2/1993 |
| EP | 0 582 198 A2 | 2/1994 |
| EP | 0 595 130 A1 | 5/1994 |
| EP | 0 596 298 A2 | 5/1994 |
| EP | 0 613 618 A1 | 9/1994 |
| EP | 0 613 884 A2 | 9/1994 |
| EP | 0 613 885 A2 | 9/1994 |
| EP | 0 647 637 A1 | 4/1995 |
| EP | 0 664 081 A2 | 7/1995 |
| EP | 0 668 267 A1 | 8/1995 |
| EP | 0 681 865 A2 | 11/1995 |
| EP | 1 598 350 A1 | 11/2005 |
| FR | 2 600 494 A1 | 12/1987 |
| GB | 2 266 888 A | 11/1993 |
| JP | 00 053 670 A | 2/2000 |
| JP | 02 205 984 A | 7/2002 |
| WO | WO 91/07874 A1 | 6/1991 |
| WO | WO 91/08202 A1 | 6/1991 |
| WO | WO 92/06094 A1 | 4/1992 |
| WO | WO 92/16108 A1 | 10/1992 |
| WO | WO 94/11374 A1 | 5/1994 |
| WO | WO 95/01971 A1 | 1/1995 |
| WO | WO 95/07897 A1 | 3/1995 |
| WO | WO 95/17817 A1 | 7/1995 |
| WO | WO 95/20572 A1 | 8/1995 |
| WO | WO 95/26954 A1 | 10/1995 |
| WO | WO 96/20196 A1 | 7/1996 |
| WO | WO 96/25395 A1 | 8/1996 |
| WO | WO 96/35664 A1 | 11/1996 |
| WO | WO 97/01535 A1 | 1/1997 |
| WO | WO 97/02243 A1 | 1/1997 |
| WO | WO 97/36868 A1 | 10/1997 |
| WO | WO 97/43275 A2 | 11/1997 |
| WO | WO 98/05638 A2 | 2/1998 |
| WO | WO 98/06721 A1 | 2/1998 |
| WO | WO 98/25928 A1 | 6/1998 |
| WO | WO 98/35553 A1 | 8/1998 |
| WO | WO 99/16748 A1 | 4/1999 |
| WO | WO 99/24437 A1 | 5/1999 |
| WO | WO 99/43649 A1 | 9/1999 |
| WO | WO 99/48869 A1 | 9/1999 |
| WO | WO 99/55673 A1 | 11/1999 |
| WO | WO 99/66795 A1 | 12/1999 |
| WO | WO 00/35278 A1 | 6/2000 |
| WO | WO 01/17972 A2 | 3/2001 |

(56) References Cited

FOREIGN PATENT DOCUMENTS

| | | | |
|---|---|---|---|
| WO | WO 01/23354 | A2 | 4/2001 |
| WO | WO 01/74770 | A1 | 10/2001 |
| WO | WO 03/013249 | A1 | 2/2003 |
| WO | WO 03/059065 | A1 | 7/2003 |
| WO | WO 03/062244 | A1 | 7/2003 |
| WO | WO 2004/007448 | A1 | 1/2004 |
| WO | WO 2004/024688 | A1 | 3/2004 |
| WO | WO 2004/065366 | A1 | 8/2004 |
| WO | WO 2004/080962 | A1 | 9/2004 |
| WO | WO 2004/111042 | A1 | 12/2004 |
| WO | WO 2005/044791 | A2 | 5/2005 |
| WO | WO 2005/044796 | A1 | 5/2005 |
| WO | WO 2005/048710 | A1 | 6/2005 |
| WO | WO 2005/049569 | A1 | 6/2005 |
| WO | WO 2005/066125 | A1 | 7/2005 |
| WO | WO 2005/092897 | A2 | 10/2005 |
| WO | WO 2006/000355 | A1 | 1/2006 |
| WO | WO 2006/024411 | A2 | 3/2006 |
| WO | WO 2006/029799 | A1 | 3/2006 |
| WO | WO 2006/056281 | A1 | 6/2006 |
| WO | WO 2006/056282 | A1 | 6/2006 |
| WO | WO 2006/089633 | A2 | 8/2006 |
| WO | WO 2007/048545 | A2 | 5/2007 |
| WO | WO 2007/068427 | A2 | 6/2007 |
| WO | WO 2007/068428 | A2 | 6/2007 |
| WO | WO 2007/073856 | A2 | 7/2007 |
| WO | WO 2007/096058 | A1 | 8/2007 |
| WO | WO 2007/121868 | A1 | 11/2007 |
| WO | WO 2007/140881 | A1 | 12/2007 |
| WO | WO 2008/067873 | A1 | 6/2008 |
| WO | WO 2008/067910 | A1 | 6/2008 |
| WO | WO 2008/083950 | A2 | 7/2008 |

OTHER PUBLICATIONS

English language translation of WO 2008/067910 A1 cited as FP104 (2008).

English language translation of WO 2008/083950 A2 cited as FP106 (2008).

Baur, P., et al., "Polydisperse Ethoxylated Fatty Alcohol Surfactants as Accelerators of Cuticular Penetration. I. Effects of Ethoxy Chain Length and the Size of the Penetrants," *Pesticide Science*, 51(2):131-152, Wiley, Chichester, Royaume-Uni UK (1997).

Bhatfacharya, B., "Isoquinoline Derivatives: Part XVIII—Formation of 1-Alkyl-(or alkaryl or aryl)-3-methyl-7-chloro-(or 5-chloro)-isoquinolines," *Indian Journal of Chemistry*, 6:341-345, National Institute of Science Communication and Information Resources, India (1968).

Compagnon, P.L. And Miocque, M., "Addition Des Reactifs Nucleophiles Sur La Triple Liaison Nitrile," *Ann. Chim.*, 14(5):11-22, Wiley Interscience, France (1970).

Edward, J.T. and Jitrangsri, C., "Stereochemistry of the Bucherer-Bergs and Strecker Reactions of 4-*tert*-Butylcyclohexanone," *Canadian Journal of Chemistry*, 53:3339-3350, National Research Council of Canada, Canada (1975).

Harrison, H.R., et al., "Use of Molecular Sieves in the Methyl Esterification of Carboxylic Acids," *Chemistry and Industry*, p. 1568, Society of Chemical Industry, UK (1968).

Ito, M., et al., "Synthesis and Insecticidal Activity of Novel N-Oxydihydropyrrole Derivatives with a Substituted Spirocyclohexyl Group," *Bioscience, Biotechnology, and Biochemistry*, 67(6):1230-1238, Japan Society for Bioscience, Biotechnology, and Agrochemistry, Japan (2003).

Munday, L., "Amino-Acids of the Cyclohexane Series. Part 1," *Journal of Chemical Society*, 10:4372-4379, Royal Society of Chemistry, UK (1961).

Schmierer, R. And Mildenberger, H., "Cyclisierung von N-Acylalanin- and N-Acylglycinestern," *Liebigs Ann. Der Chemie*, 5:1095-1098, VCH, Weinheim, Allemagne (1985).

Sonntag, N.O.V., "The Reaction of Aliphatic Acid Chlorides," *Chemical Reviews*, 52(2):237-416, ACS Publications, USA (1953).

Suzuki, S., et al., "Studies on Antiviral Agents IV. Biological Activity of Tenuazomc Acid Derivatives," *Chemical and Pharmaceutical Bulletin*, 15(8):1120-1122, Pharmaceutical Society of Japan, Japan (1967).

English language Abstract of European Patent Publication No. EP 0 346 620 A1 (1989).

English language Abstract of German Patent Publication No. DE 10 2005 059 892 A1 (2007).

English language Abstract of German Patent Publication No. De 10 2006 050 148 A1 (2008).

English language Abstract of German Patent Publication No. De 10 2006 057 037 A1 (2008).

English language Abstract of German Patent Publication No. DE 10 2007 001 866 A1 (2008).

English language Abstract of Japanese Patent Publication No. JP 00-053670 A (2000).

English language Abstract of Japanese Patent Publication No. JP 02-205984 A (2002).

English language Abstract of WIPO Patent Publication No. WO 2008/067873 A1 (2008).

English language Abstract of WIPO Patent Publication No. WO 2008/067910 A1 (2008).

English language Abstract of WIPO Patent Publication No. WO 2008/083950 A2 (2008).

International Search Report for Application No. PCT/EP2008/005973, European Patent Office, The Netherlands, mailed on Nov. 28, 2008.

English language translation of NPL-3 (1970).

English language machine translation of NPL8 (1985).

OXASPIROCYCLIC SPIRO-SUBSTITUTED TETRAMIC ACID AND TETRONIC ACID DERIVATIVES

The present invention relates to novel oxaspirocyclic spiro-substituted tetramic and tetronic acid derivatives, to a plurality of processes for their preparation and to their use as pesticides and/or herbicides. The invention also provides selective herbicidal compositions comprising, firstly, the oxaspirocyclic spiro-substituted tetramic and tetronic acid derivatives and, secondly, a crop plant compatibility-improving compound.

The present invention furthermore relates to the boosting of the action of crop protection compositions comprising, in particular, oxaspirocyclic spiro-substituted tetramic and tetronic acid derivatives, through the addition of ammonium salts or phosphonium salts and optionally penetrants, to the corresponding compositions, to processes for producing them and to their application in crop protection as insecticides and/or acaricides and/or for preventing unwanted plant growth.

For 3-acylpyrrolidine-2,4-diones pharmaceutical properties have been previously described (S. Suzuki et al. Chem. Pharm. Bull. 15 1120 (1967)). Furthermore, N-phenylpyrrolidine-2,4-diones have been synthesized by R. Schmierer and H. Mildenberger (Liebigs Ann. Chem. 1985, 1095). Biological activity of these compounds has not been described.

EP-A-0 262 399 and GB-A-2 266 888 disclose similarly structured compounds (3-aryl-pyrrolidine-2,4-diones) for which, however, no herbicidal, insecticidal or acaricidal action has been disclosed. Known compounds with herbicidal, insecticidal or acaricidal action are unsubstituted bicyclic 3-arylpyrrolidine-2,4-dione derivatives (EP-A-355 599, EP-A-415 211 and JP-A-12-053 670) and also substituted monocyclic 3-arylpyrrolidine-2,4-dione derivatives (EP-A-377 893 and EP-A-442 077).

Additionally known are polycyclic 3-arylpyrrolidine-2,4-dione derivatives (EP-A-442 073) and 1H-arylpyrrolidinedione derivatives (EP-A-456 063, EP-A-521 334, EP-A-596 298, EP-A-613 884, EP-A-613 885, WO 94/01 997, WO 95/26 954, WO 95/20 572, EP-A-0 668 267, WO 96/25 395, WO 96/35 664, WO 97/01 535, WO 97/02 243, WO 97/36 868, WO 97/43275, WO 98/05638, WO 98/06721, WO 98/25928, WO 99/24437, WO 99/43649, WO 99/48869 and WO 99/55673, WO 01/17972, WO 01/23354, WO 01/74770, WO 03/013249, WO 03/062244, WO 2004/007448, WO 2004/024 688, WO 04/065366, WO 04/080962, WO 04/111042, WO 05/044791, WO 05/044796, WO 05/048710, WO 05/049596, WO 05/066125, WO 05/092897, WO 06/000355, WO 06/029799, WO 06/056281, WO 06/056282, WO 06/089633, WO 07/048545, DEA 102 00505 9892, WO 07/073856, WO 07/096058, WO 07/121868, WO 07/140881, DEA 102 00600 7882, DEA 102 00605 0148, DEA 102 00605 7036 and DEA 102 00605 7037). Furthermore known are ketal-substituted 1-H-arylpyrrolidine-2,4-diones from WO 99/16748 and (spiro)-ketal-substituted N-alkoxyalkoxy-substituted arylpyrrolidinediones from JP-A-14 205 984 and Ito M. et. al., Bioscience, Biotechnology and Biochemistry 67, 1230-1238, (2003). The addition of safeners to ketoenols is also known in principle from WO 03/013249. Moreover, WO 06/024411 discloses herbicidal compositions comprising ketoenols.

It is known that certain Δ³-dihydrofuran-2-one derivatives have herbicidal, insecticidal or acaricidal properties: EP-A-528 156, EP-A-647 637, WO 95/26 954, WO 96/20 196, WO 96/25 395, WO 96/35 664, WO 97/01 535, WO 97/02 243, WO 97/36 868, WO 98/05 638, WO 98/06 721, WO 99/16 748, WO 98/25 928, WO 99/43 649, WO 99/48 869, WO 99/55 673, WO 01/23354, WO 01/74 770, WO 01/17 972, WO 04/024 688, WO 04/080 962, WO 04/111 042, WO 05/092 897, WO 06/000 355, WO 06/029 799, WO 07/048545, WO 07/073856, WO 07/096058, DEA 102 00605 7036, DEA 102 00700 1866.

However, the herbicidal and/or acaricidal and/or insecticidal activity and/or activity spectrum and/or the plant compatibility of the known compounds, in particular with respect to crop plants, is/are not always satisfactory.

This invention now provides novel compounds of the formula (I)

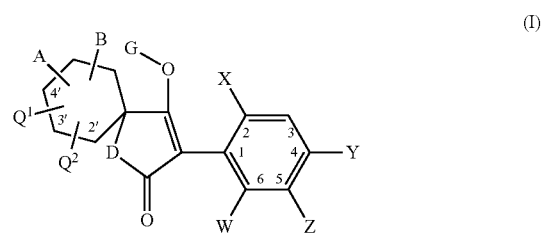

(I)

in which
W represents hydrogen, alkyl, alkenyl, alkynyl, optionally substituted cycloalkyl, halogen, alkoxy, alkenyloxy, haloalkyl, haloalkoxy or cyano,
X represents halogen, alkyl, alkenyl, alkynyl, optionally substituted cycloalkyl, alkoxy, alkenyloxy, alkylthio, alkylsulphinyl, alkylsulphonyl, haloalkyl, haloalkoxy, haloalkenyloxy, nitro or cyano,
Y and Z independently of one another represent hydrogen, alkyl, alkenyl, alkynyl, optionally substituted cycloalkyl, alkoxy, halogen, haloalkyl, haloalkoxy, cyano, nitro or in each case optionally substituted aryl or hetaryl,
A and B and the carbon atom to which they are attached represent a tetrahydrofuran ring or tetrahydropyran ring, each of which is optionally substituted by alkyl, haloalkyl, alkoxy, alkoxyalkyl or optionally substituted phenyl,
D represents NH or oxygen,
$Q^1$, $Q^2$ independently of one another represent hydrogen, alkyl, haloalkyl or alkoxy,
G represents hydrogen (a) or represents one of the groups

(b)

(c)

(d)

(e)

(f)

E, or

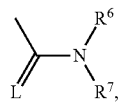

in which
E represents a metal ion or an ammonium ion,
L represents oxygen or sulphur,
M represents oxygen or sulphur,
R¹ represents in each case optionally halogen- or cyano-substituted alkyl, alkenyl, alkoxyalkyl, alkylthioalkyl or polyalkoxyalkyl or represents in each case optionally halogen-, alkyl- or alkoxy-substituted cycloalkyl or heterocyclyl or represents in each case optionally substituted phenyl, phenylalkyl, hetaryl, phenoxyalkyl or hetaryloxyalkyl,
R² represents in each case optionally halogen- or cyano-substituted alkyl, alkenyl, alkoxyalkyl or polyalkoxyalkyl or represents in each case optionally substituted cycloalkyl, phenyl or benzyl,
R³, R⁴ and R⁵ independently of one another represent in each case optionally halogen-substituted alkyl, alkoxy, alkylamino, dialkylamino, alkylthio, alkenylthio or cycloalkylthio or represent in each case optionally substituted phenyl, benzyl, phenoxy or phenylthio,
R⁶ and R⁷ independently of one another represent hydrogen, represent in each case optionally halogen- or cyano-substituted alkyl, cycloalkyl, alkenyl, alkoxy, alkoxyalkyl, represent in each case optionally substituted phenyl or benzyl, or together with the nitgrogen atom to which they are attached form an optionally substituted cycle which optionally contains oxygen or sulphur.

Depending inter alia on the nature of the substituents, the compounds of the formula (I) may be present as optical isomers or isomer mixtures of varying composition which, if appropriate, may be separated in a customary manner. The present invention provides the pure isomers and the isomer mixtures, their preparation and use and compositions comprising them. However, for the sake of simplicity, hereinbelow only compounds of the formula (I) are referred to, although what is meant are both the pure compounds and, if appropriate, mixtures having various proportions of isomeric compounds.

Including D for NH (1) and D for O (2), the following principal structures (I-1) to (I-2) result:

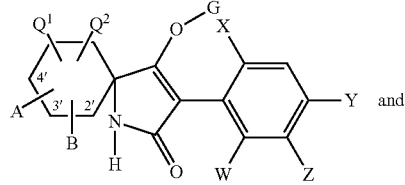

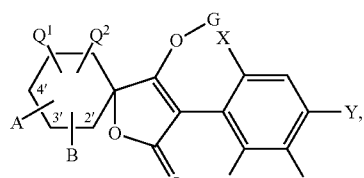

in which
A, B, G, Q¹, Q², W, X, Y and Z have the meaning given above.

Including the various meanings (a), (b), (c), (d), (e), (f) and (g) of the group G, the following principal structures (I-1-a) to (I-1-g) result if D represents NH (1),

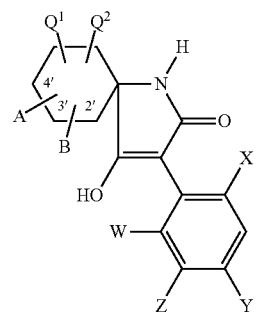

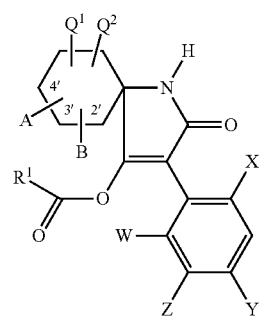

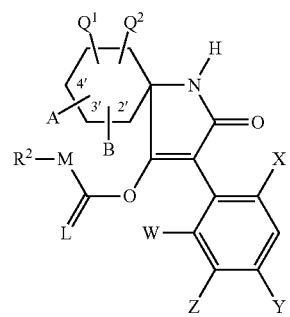

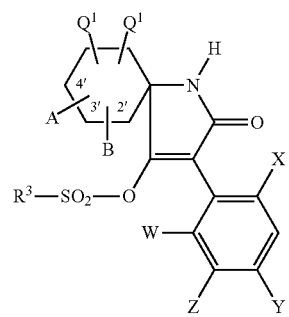

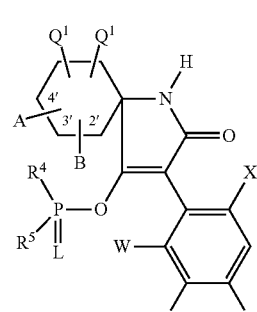

-continued

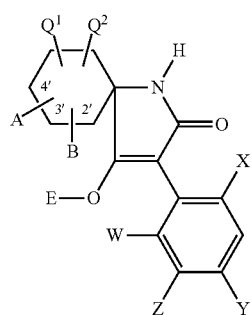
(I-1-f)

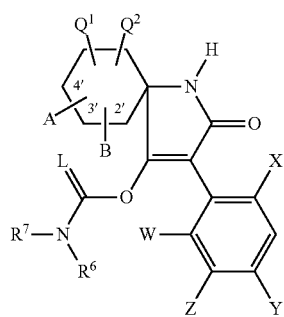
(I-1-g)

in which

A, B, E, L, M, $Q^1$, $Q^2$, W, X, Y, Z, $R^1$, $R^2$, $R^3$, $R^4$, $R^5$, $R^6$ and $R^7$ have the meanings given above.

Including the various meanings (a), (b), (c), (d), (e), (f) and (g) of the group G, the following principal structures (I-2-a) to (I-2-g) result if D represents O (2)

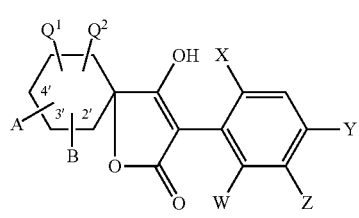
(I-2-a)

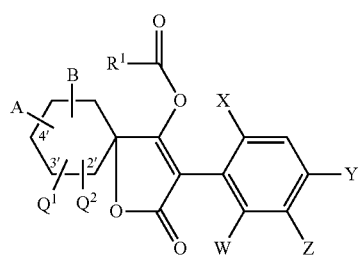
(I-2-b)

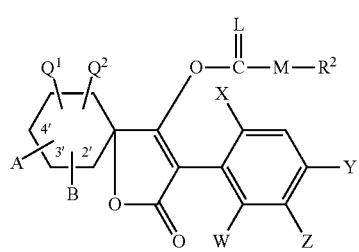
(I-2-c)

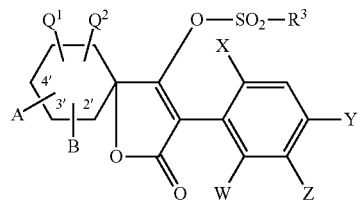
(I-2-d)

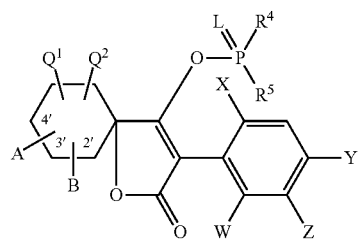
(I-2-e)

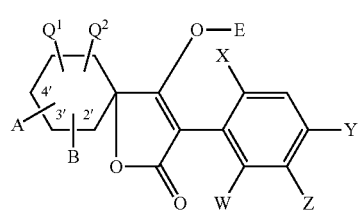
(I-2-f)

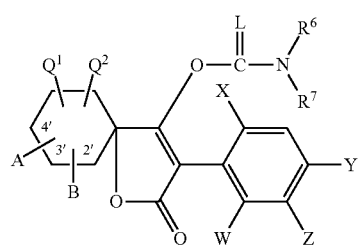
(I-2-g)

in which

A, B, E, L, M, $Q^1$, $Q^2$, W, X, Y, Z, $R^1$, $R^2$, $R^3$, $R^4$, $R^5$, $R^6$ and $R^7$ have the meaning given above.

Furthermore, it has been found that the novel compounds of the formula (I) are obtained by one of the processes described below:

(A) compounds of the formula (I-1-a)

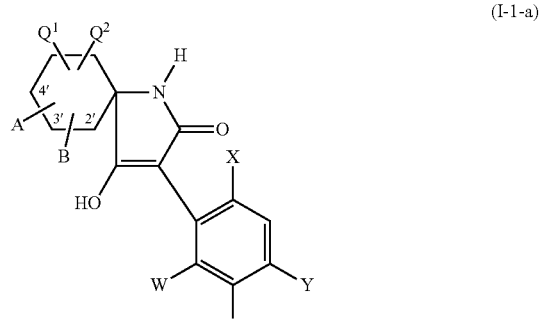
(I-1-a)

in which

A, B, $Q^1$, $Q^2$, W, X, Y and Z have the meanings given above are obtained when compounds of the formula (II)

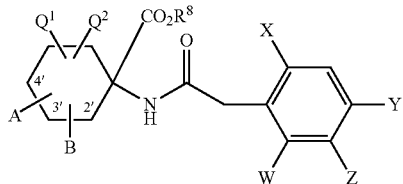
(II)

in which

A, B, Q$^1$, Q$^2$, W, X, Y and Z have the meanings given above, and

R$^8$ represents alkyl (preferably C$_1$-C$_6$-alkyl), are condensed intramolecularly in the presence of a diluent and in the presence of a base.

(B) Moreover, it has been found that compounds of the formula (I-2-a)

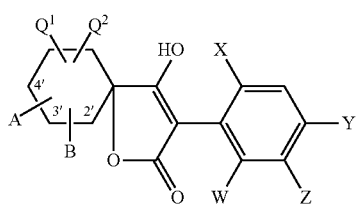
(I-2-a)

in which

A, B, Q$^1$, Q$^2$, W, X, Y and Z have the meanings given above are obtained when compounds of the formula (III)

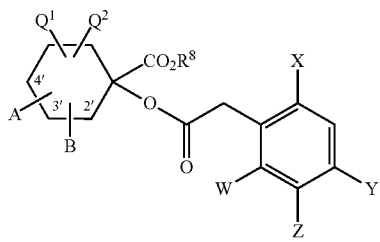
(III)

in which

A, B, Q$^1$, Q$^2$, W, X, Y, Z and R$^8$ have the meanings given above are condensed intramolecularly in the presence of a diluent and in the presence of a base.

Moreover, it has been found (C) that the compounds of the formulae (I-1-b) to (I-2-b) shown above in which R$^1$, A, B, Q$^1$, Q$^2$, W, X, Y and Z have the meanings given above are obtained when compounds of the formulae (I-1-a) to (I-2-a) shown above in which A, B, Q$^1$, Q$^2$, W, X, Y and Z have the meanings given above are in each case reacted α) with compounds of the formula (IV)

(IV)

in which

R$^1$ has the meaning given above and

Hal represents halogen (in particular chlorine or bromine) or

β) with carboxylic anhydrides of the formula (V)

(V)

in which

R$^1$ has the meaning given above, if appropriate in the presence of a diluent and if appropriate in the presence of an acid binder;

(D) that the compounds of the formulae (I-1-c) to (I-2-c) shown above in which R$^2$, A, B, Q$^1$, Q$^2$, M, W, X, Y and Z have the meanings given above and L represents oxygen are obtained when compounds of the formulae (I-1-a) to (I-2-a) shown above in which A, B, Q$^1$, Q$^2$, W, X, Y and Z have the meanings given above are in each case reacted with chloroformic esters or chloroformic thioesters of the formula (VI)

(VI)

in which

R$^2$ and M have the meanings given above, if appropriate in the presence of a diluent and if appropriate in the presence of an acid binder;

(E) that compounds of the formulae (I-1-c) to (I-2-c) shown above in which R$^2$, A, B, Q$^1$, Q$^2$, M, W, X, Y and Z have the meanings given above and L represents sulphur are obtained when compounds of the formulae (I-1-a) to (I-2-a) shown above in which A, B, Q$^1$, Q$^2$, W, X, Y and Z have the meanings given above are in each case reacted with chloromonothioformic esters or chlorodithioformic esters of the formulal (VII)

(VII)

in which

M and R$^2$ have the meanings given above, if appropriate in the presence of a diluent and if appropriate in the presence of an acid binder, (F) that compounds of the formulae (I-1-d) to (I-2-d) shown above in which R$^3$, A, B, Q$^1$, Q$^2$, W, X, Y and Z have the meanings given above are obtained when compounds of the formulae (I-1-a) to (I-2-a) shown above in which A, B, Q$^1$, Q$^2$, W, X, Y and Z have the meanings given above are in each case reacted with sulphonyl chlorides of the formula (VIII)

(VIII)

in which

R$^3$ has the meaning given above, if appropriate in the presence of a diluent and if appropriate in the presence of an acid binder, (G) that compounds of the formulae (I-1-e) to (I-2-e) shown above in which L, $R^4$, $R^5$, A, B, $Q^1$, $Q^2$, W, X, Y and Z have the meanings given above are obtained when compounds of the formulae (I-1-a) to (I-2-a) shown above in which A, B, $Q^1$, $Q^2$, W, X, Y and Z have the meanings given above are in each case
reacted with phosphorus compounds of the formula (IX)

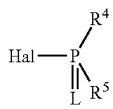   (IX)

in which
L, $R^4$ and $R^5$ have the meanings given above and
Hal represents halogen (in particular chlorine or bromine),
if appropriate in the presence of a diluent and if appropriate in the presence of an acid binder,
(H) that compounds of the formulae (I-1-f) to (I-2-f) shown above in which E, A, B, $Q^1$, $Q^2$, W, X, Y and Z have the meanings given above are obtained when compounds of the formulae (I-1-a) to (I-2-a), in which A, B, $Q^1$, $Q^2$, W, X, Y and Z have the meanings given above are in each case reacted
with metal compounds or amines of the formulae (X) or (XI), respectively, $Me(OR^{10})_t$   (X)

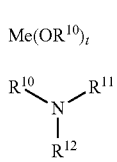   (XI)

in which
Me represents a mono- or divalent metal (preferably an alkali metal or alkaline earth metal, such as lithium, sodium, potassium, magnesium or calcium),
t represents the number 1 or 2 and
$R^{10}$, $R^{11}$, $R^{12}$ independently of one another represent hydrogen or alkyl (preferably $C_1$-$C_8$-alkyl),
if appropriate in the presence of a diluent,
(I) that compounds of the formulae (I-1-g) to (I-2-g) shown above in which L, $R^6$, $R^7$, A, B, $Q^1$, $Q^2$, W, X, Y and Z have the meanings given above are obtained when compounds of the formulae (I-1-a) to (I-2-a) shown above in which A, B, $Q^1$, $Q^2$, W, X, Y and Z have the meanings given above, are in each case reacted
α) with isocyanates or isothiocyanates of the formula (XII)

$R^6$—N═C═L   (XII)

in which
$R^6$ and L have the meanings given above,
if appropriate in the presence of a diluent and if appropriate in the presence of a catalyst, or
β) with carbamoyl chlorides or thiocarbamoyl chlorides of the formula (XIII)

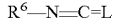   (XIII)

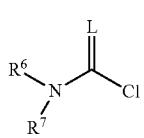

in which
L, $R^6$ and $R^7$ have the meanings given above, if appropriate in the presence of a diluent and if appropriate in the presence of an acid binder,
(Jα) that compounds of the formulae (I-1a) to (I-2-g) shown above in which A, B, D, G, $Q^1$, $Q^2$, W, X, Y and Z have the meaning given above are obtained when compounds of the formulae (I-1-a') to (I-2-g') in which A, B, D, G, $Q^1$, $Q^2$, W, X and Y have the meaning given above and Z' preferably represents bromine or iodine

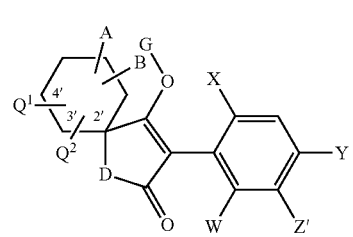   (I-1-a' to I-2-g')

and
(Jβ) that compounds of the formulae (I-1-a) to (I-2-g) shown above in which A, B, D, G, $Q^1$, $Q^2$, W, X, Y and Z have the meaning given above are obtained when compounds of the formulae (I-1-a") to (I-2-g") in which A, B, D, G, $Q^1$, $Q^2$, W, X and Z have the meaning given above and Y' preferably represents bromine or iodine

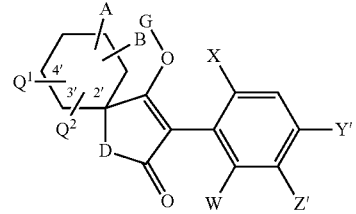   (I-1-a" to I-2-g")

are coupled when (het)aryl derivatives capable of coupling, for example phenylboronic acids of the formulae (XVα) and (XVβ)

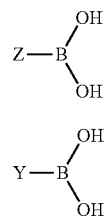   (XVα)

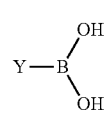   (XVβ)

or esters thereof, are coupled in the presence of a solvent, in the presence of a catalyst (for example Pd complexes) and in presence of a base (for example sodium carbonate, potassium phosphate).

Furthermore, it has been found that the novel compounds of the formula (I) are very effective as pesticides, preferably as insecticides and/or acaricides and/or herbicides, and additionally frequently tolerated very well by plants, in particular crop plants.

Surprisingly, it has now also been found that certain oxaspirocyclic spiro-substituted tetramic and tetronic acid derivatives, when used together with the crop plant compatibility-improving compounds (safeners/antidotes) described below, efficiently prevent damage to the crop plants and can be used in a particularly advantageous manner as broad-spectrum combination preparations for the selective control of unwanted plants in crops of useful plants, such as, for example, in cereals, but also in maize, soya beans and rice.

The invention also provides selective herbicidal compositions comprising an effective amount of an active compound combination comprising, as components, (a') at least one compound of the formula (I) in which A, B, D, G, $Q^1$, $Q^2$, W, X, Y and Z are as defined above and (b') at least one crop plant compatibility-improving compound from the following group of compounds:

4-dichloroacetyl-1-oxa-4-azaspiro[4.5]decane (AD-67, MON-4660), 1-dichloroacetylhexahydro-3,3,8a-trimethylpyrrolo[1,2-a]pyrimidin-6(2H)-one (dicyclonon, BAS-145138), 4-dichloroacetyl-3,4-dihydro-3-methyl-2H-1,4-benzoxazine (benoxacor), 1-methylhexyl 5-chloroquinoline-8-oxyacetate (cloquintocet-mexyl—cf. also related compounds in EP-A-86750, EP-A-94349, EP-A-191736, EP-A-492366), 3-(2-chlorobenzyl)-1-(1-methyl-1-phenylethyl)urea (cumyluron), α-(cyanomethoximino)phenylacetonitrile (cyometrinil), 2,4-dichlorophenoxyacetic acid (2,4-D), 4-(2,4-dichlorophenoxy)butyric acid (2,4-DB), 1-(1-methyl-1-phenylethyl)-3-(4-methylphenyl)urea (daimuron, dymron), 3,6-dichloro-2-methoxybenzoic acid (dicamba), S-1-methyl-1-phenylethyl piperidine-1-thiocarboxylate (dimepiperate), 2,2-dichloro-N-(2-oxo-2-(2-propenylamino) ethyl)-N-(2-propenyl)acetamide (DKA-24), 2,2-dichloro-N, N-di-2-propenylacetamide (dichlormid), 4,6-dichloro-2-phenylpyrimidine (fenclorim), ethyl 1-(2,4-dichlorophenyl)-5-trichloromethyl-1H-1,2,4-triazole-3-carboxylate (fenchlorazole-ethyl—cf. also related compounds in EP-A-174562 and EP-A-346620), phenylmethyl 2-chloro-4-trifluoromethylthiazole-5-carboxylate (flurazole), 4-chloro-N-(1,3-dioxolan-2-ylmethoxy)-α-trifluoroacetophenone oxime (fluxofenim), 3-dichloroacetyl-5-(2-furanyl)-2,2-dimethyloxazolidine (furilazole, MON-13900), ethyl 4,5-dihydro-5, 5-diphenyl-3-isoxazolecarboxylate (isoxadifen-ethyl—cf. also related compounds in WO-A-95/07897), 1-(ethoxycarbonyl)ethyl 3,6-dichloro-2-methoxybenzoate (lactidichlor), (4-chloro-o-tolyloxy)acetic acid (MCPA), 2-(4-chloro-o-tolyloxy)propionic acid (mecoprop), diethyl 1-(2,4-dichlorophenyl)-4,5-dihydro-5-methyl-1H-pyrazole-3,5-dicarboxylate (mefenpyr-diethyl—cf. also related compounds in WO-A-91/07874), 2-dichloromethyl-2-methyl-1,3-dioxolane (MG-191), 2-propenyl-1-oxa-4-azaspiro[4.5]decane-4-carbodithioate (MG-838), 1,8-naphthalic anhydride, α-(1, 3-dioxolan-2-ylmethoximino)phenylacetonitrile (oxabetrinil), 2,2-dichloro-N-(1,3-dioxolan-2-ylmethyl)-N-(2-propenyl)acetamide (PPG-1292), 3-dichloroacetyl-2,2-dimethyloxazolidine (R-28725), 3-dichloroacetyl-2,2,5-trimethyloxazolidine (R-29148), 4-(4-chloro-o-tolyl)butyric acid, 4-(chlorophenoxy)butyric acid, diphenylmethoxyacetic acid, methyl diphenylmethoxyacetate, ethyl diphenylmethoxyacetate, methyl 1-(2-chlorophenyl)-5-phenyl-1H-pyrazole-3-carboxylate, ethyl 1-(2,4-dichlorophenyl)-5-methyl-1H-pyrazole-3-carboxylate, ethyl 1-(2,4-dichlorophenyl)-5-isopropyl-1H-pyrazole-3-carboxylate, ethyl 1-(2,4-dichlorophenyl)-5-(1,1-dimethylethyl)-1H-pyrazole-3-carboxylate, ethyl 1-(2,4-dichlorophenyl)-5-phenyl-1H-pyrazole-3-carboxylate (cf. also related compounds in EP-A-269806 and EP-A-333131), ethyl 5-(2,4-dichlorobenzyl)-2-isoxazoline-3-carboxylate, ethyl 5-phenyl-2-isoxazoline-3-carboxylate, ethyl 5-(4-fluorophenyl)-5-phenyl-2-isoxazoline-3-carboxylate (cf. also related compounds in WO-A-91/08202), 1,3-dimethylbut-1-yl 5-chloroquinoline-8-oxyacetate, 4-allyloxybutyl 5-chloro-quinoline-8-oxyacetate, 1-allyloxyprop-2-yl 5-chloroquinoline-8-oxyac- etate, methyl 5-chloroquinoxaline-8-oxyacetate, ethyl 5-chloroquinoline-8-oxyacetate, allyl 5-chloroquinoxaline-8-oxyacetate, 2-oxoprop-1-yl 5-chloroquinoline-8-oxyacetate, diethyl 5-chloroquinoline-8-oxymalonate, diallyl 5-chloroquinoxaline-8-oxymalonate, diethyl 5-chloroquinoline-8-oxymalonate (cf. also related compounds in EP-A-582198), 4-carboxychroman-4-ylacetic acid (AC-304415, cf. EP-A-613618), 4-chlorophenoxyacetic acid, 3,3'-dimethyl-4-methoxybenzophenone, 1-bromo-4-chloromethylsulphonylbenzene, 1-[4-(N-2-methoxybenzoylsulphamoyl)phenyl]-3-methylurea (also known as N-(2-methoxybenzoyl)-4-[(methylaminocarbonyl)amino]benzenesulphonamide), 1-[4-(N-2-methoxybenzoylsulphamoyl)-phenyl]-3,3-dimethylurea, 1-[4-(N-4,5-dimethylbenzoylsulphamoyl)phenyl]-3-methylurea, 1-[4-(N-naphthylsulphamoyl)phenyl]-3, 3-dimethylurea, N-(2-methoxy-5-methylbenzoyl)-4-(cyclopropylaminocarbonyl)benzenesulphonamide, and/or one of the following compounds, defined by general formulae of the general formula (IIa)

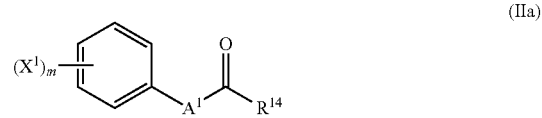

or of the general formula (IIb)

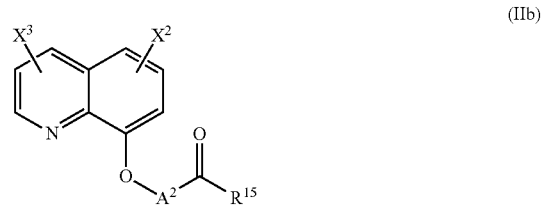

or of the formula (IIc)

where
m represents a number 0, 1, 2, 3, 4 or 5,
$A^1$ represents one of the divalent heterocyclic groupings shown below,

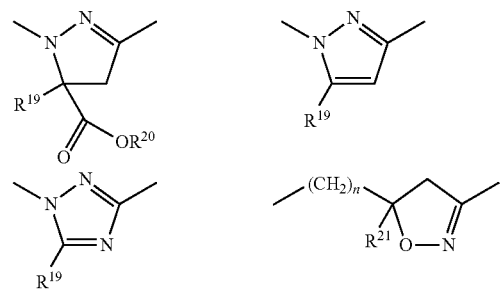

n represents a number 0, 1, 2, 3, 4 or 5, $A^2$ represents optionally $C_1$-$C_4$-alkyl- and/or $C_1$-$C_4$-alkoxy-carbonyl- and/or $C_1$-$C_4$-alkenyloxy-carbonyl-substituted alkanediyl having 1 or 2 carbon atoms, $R^{14}$ represents hydroxyl, mercapto, amino, $C_1$-$C_6$-alkoxy, $C_1$-$C_6$-alkylthio, $C_1$-$C_6$-alkylamino or di($C_1$-$C_4$-alkyl) amino, $R^{15}$ represents hydroxyl, mercapto, amino, $C_1$-$C_7$-alkoxy, $C_1$-$C_6$-alkylthio, $C_1$-$C_6$-alkenyloxy, $C_1$-$C_6$-alkenyloxy-$C_1$-$C_6$-alkoxy, $C_1$-$C_6$-alkylamino or di($C_1$-$C_4$-alkyl) amino, $R^{16}$ represents optionally fluorine-, chlorine- and/or bromine-substituted $C_1$-$C_4$-alkyl, $R^{17}$ represents hydrogen, in each case optionally fluorine-, chlorine- and/or bromine-substituted $C_1$-$C_6$-alkyl, $C_2$-$C_6$-alkenyl or $C_2$-$C_6$-alkynyl, $C_1$-$C_4$-alkoxy-$C_1$-$C_4$-alkyl, dioxolanyl-$C_1$-$C_4$-alkyl, furyl, furyl-$C_1$-$C_4$-alkyl, thienyl, thiazolyl, piperidinyl, or optionally fluorine-, chlorine- and/or bromine- or $C_1$-$C_4$-alkyl-substituted phenyl, $R^{18}$ represents hydrogen, in each case optionally fluorine-, chlorine- and/or bromine-substituted $C_1$-$C_6$-alkyl, $C_2$-$C_6$-alkenyl or $C_2$-$C_6$-alkynyl, $C_1$-$C_4$-alkoxy-$C_1$-$C_4$-alkyl, dioxolanyl-$C_1$-$C_4$-alkyl, furyl, furyl-$C_1$-$C_4$-alkyl, thienyl, thiazolyl, piperidinyl, or optionally fluorine-, chlorine- and/or bromine- or $C_1$-$C_4$-alkyl-substituted phenyl, $R^{17}$ and $R^{18}$ also together represent $C_3$-$C_6$-alkanediyl or $C_2$-$C_5$-oxaalkanediyl, each of which is optionally substituted by $C_1$-$C_4$-alkyl, phenyl, furyl, a fused benzene ring or by two substituents which, together with the C atom to which they are attached, form a 5- or 6-membered carbocycle, $R^{19}$ represents hydrogen, cyano, halogen, or represents in each case optionally fluorine-, chlorine- and/or bromine-substituted $C_1$-$C_4$-alkyl, $C_3$-$C_6$-cycloalkyl or phenyl, $R^{20}$ represents hydrogen, in each case optionally hydroxyl-, cyano-, halogen- or $C_1$-$C_4$-alkoxy-substituted $C_1$-$C_6$-alkyl, $C_3$-$C_6$-cycloalkyl or tri-($C_1$-$C_4$-alkyl)silyl, $R^{21}$ represents hydrogen, cyano, halogen, or represents in each case optionally fluorine-, chlorine- and/or bromine-substituted $C_1$-$C_4$-alkyl, $C_3$-$C_6$-cycloalkyl or phenyl, $X^1$ represents nitro, cyano, halogen, $C_1$-$C_4$-alkyl, $C_1$-$C_4$-haloalkyl, $C_1$-$C_4$-alkoxy or $C_1$-$C_4$-haloalkoxy, $X^2$ represents hydrogen, cyano, nitro, halogen, $C_1$-$C_4$-alkyl, $C_1$-$C_4$-haloalkyl, $C_1$-$C_4$-alkoxy or $C_1$-$C_4$-haloalkoxy, $X^3$ represents hydrogen, cyano, nitro, halogen, $C_1$-$C_4$-alkyl, $C_1$-$C_4$-haloalkyl, $C_1$-$C_4$-alkoxy or $C_1$-$C_4$-haloalkoxy, and/or the following compounds, defined by general formulae of the general formula (IId)

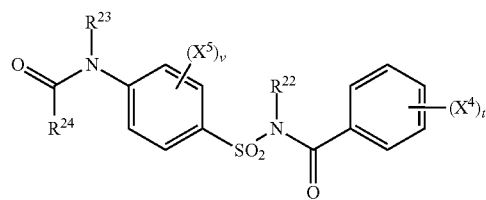

(IId)

or of the general formula (IIe)

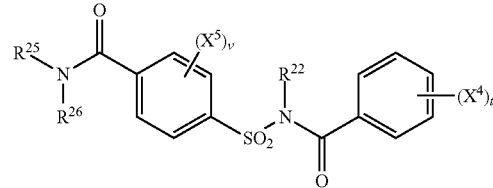

(IIe)

where t represents a number 0, 1, 2, 3, 4 or 5, v represents a number 0, 1, 2, 3, 4 or 5, $R^{22}$ represents hydrogen or $C_1$-$C_4$-alkyl, $R^{23}$ represents hydrogen or $C_1$-$C_4$-alkyl, $R^{24}$ represents hydrogen, in each case optionally cyano-, halogen- or $C_1$-$C_4$-alkoxy-substituted $C_1$-$C_6$-alkyl, $C_1$-$C_6$-alkoxy, $C_1$-$C_6$-alkylthio, $C_1$-$C_6$-alkylamino or di($C_1$-$C_4$-alkyl)amino, or in each case optionally cyano-, halogen- or $C_1$-$C_4$-alkyl-substituted $C_3$-$C_6$-cycloalkyl, $C_3$-$C_6$-cycloalkyloxy, $C_3$-$C_6$-cycloalkylthio or $C_3$-$C_6$-cycloalkylamino, $R^{25}$ represents hydrogen, optionally cyano-, hydroxyl-, halogen- or $C_1$-$C_4$-alkoxy-substituted $C_1$-$C_6$-alkyl, in each case optionally cyano- or halogen-substituted $C_3$-$C_6$-alkenyl or $C_3$-$C_6$-alkynyl, or optionally cyano-, halogen- or $C_1$-$C_4$-alkyl-substituted $C_3$-$C_6$-cycloalkyl, $R^{26}$ represents hydrogen, optionally cyano-, hydroxyl-, halogen- or $C_1$-$C_4$-alkoxy-substituted $C_1$-$C_6$-alkyl, in each case optionally cyano- or halogen-substituted $C_3$-$C_6$-alkenyl or $C_3$-$C_6$-alkynyl, optionally cyano-, halogen- or $C_1$-$C_4$-alkyl-substituted $C_3$-$C_6$-cycloalkyl, or optionally nitro-, cyano-, halogen-, $C_1$-$C_4$-alkyl, $C_1$-$C_4$-haloalkyly-, $C_1$-$C_4$-alkoxy- or $C_1$-$C_4$-haloalkoxy-substituted phenyl, or together with $R^{25}$ represents in each case optionally $C_1$-$C_4$-alkyl-substituted $C_2$-$C_6$-alkanediyl or $C_2$-$C_5$-oxaalkanediyl, $X^4$ represents nitro, cyano, carboxyl, carbamoyl, formyl, sulphamoyl, hydroxyl, amino, halogen, $C_1$-$C_4$-alkyl, $C_1$-$C_4$-haloalkyl, $C_1$-$C_4$-alkoxy or $C_1$-$C_4$-haloalkoxy, and $X^5$ represents nitro, cyano, carboxyl, carbamoyl, formyl, sulphamoyl, hydroxyl, amino, halogen, $C_1$-$C_4$-alkyl, $C_1$-$C_4$-haloalkyl, $C_1$-$C_4$-alkoxy or $C_1$-$C_4$-haloalkoxy.

The formula (I) provides a general definition of the compounds according to the invention. Preferred substituents or ranges of the radicals listed in the formulae mentioned above and below are illustrated below:

W preferably represents hydrogen, $C_1$-$C_6$-alkyl, $C_2$-$C_6$-alkenyl, $C_2$-$C_6$-alkynyl, represents $C_3$-$C_6$-cycloalkyl which is optionally mono- or disubstituted by $C_1$-$C_2$-alkyl, $C_1$-$C_2$-alkoxy, fluorine, chlorine, trifluoromethyl or $C_3$-$C_6$-cycloalkyl, represents halogen, $C_1$-$C_6$-alkoxy, $C_1$-$C_4$-haloalkyl, $C_1$-$C_4$-haloalkoxy or cyano, X preferably represents halogen, $C_1$-$C_6$-alkyl, $C_2$-$C_6$-alkenyl, $C_2$-$C_6$-alkynyl, represents $C_3$-$C_6$-cycloalkyl which is optionally mono- or disubstituted by $C_1$-$C_2$-alkyl, $C_1$-$C_2$-alkoxy, fluorine, chlorine, trifluoromethyl or $C_3$-$C_6$-cycloalkyl, represents $C_1$-$C_6$-haloalkyl, $C_1$-$C_6$-alkoxy, $C_3$-$C_6$-alkenyloxy, $C_1$-$C_6$-alkylthio, $C_1$-$C_6$-alkylsulphinyl, $C_1$-$C_6$-alkylsulphonyl, $C_1$-$C_6$-haloalkoxy, $C_3$-$C_6$-haloalkenyloxy, nitro or cyano, Y and Z independently of one another preferably represent hydrogen, halogen, $C_1$-$C_6$-alkyl, $C_2$-$C_6$-alkenyl, $C_2$-$C_6$-alkynyl, represent $C_3$-$C_6$-cycloalkyl which is optionally mono- or disubstituted by $C_1$-$C_2$-alkyl, $C_1$-$C_2$-alkoxy, fluorine, chlorine, trifluoromethyl or $C_3$-$C_6$-cycloalkyl, represent $C_1$-$C_6$-alkoxy, $C_1$-$C_6$-haloalkyl, $C_1$-$C_6$-haloalkoxy, cyano, $C_2$-$C_6$-alkenyl, $C_2$-$C_6$-alkynyl or represent one of the (het)aryl radicals

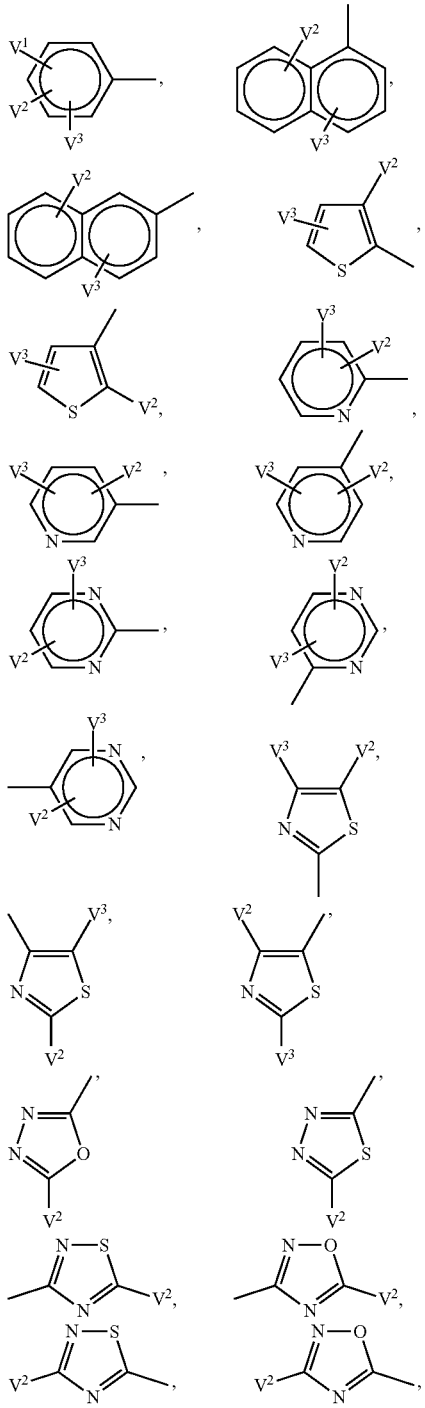

where in the case of (het)aryl only one of the radicals Y or Z may represent (het)aryl, $V^1$ preferably represents hydrogen, halogen, $C_1$-$C_{12}$-alkyl, $C_1$-$C_6$-alkoxy, $C_1$-$C_6$-alkylthio, $C_1$-$C_6$-alkylsulphinyl, $C_1$-$C_6$-alkylsulphonyl, $C_1$-$C_4$-haloalkyl, $C_1$-$C_4$-haloalkoxy, nitro, cyano or represents phenyl, phenoxy, phenoxy-$C_1$-$C_4$-alkyl, phenyl-$C_1$-$C_4$-alkoxy, phenylthio-$C_1$-$C_4$-alkyl or phenyl-$C_1$-$C_4$-alkylthio, each of which is optionally mono- or polysubstituted by halogen, $C_1$-$C_6$-alkyl, $C_1$-$C_6$-alkoxy, $C_1$-$C_4$-haloalkyl, $C_1$-$C_4$-haloalkoxy, nitro or cyano, $V^2$ and $V^3$ independently of one another preferably represent hydrogen, halogen, $C_1$-$C_6$-alkyl, $C_1$-$C_6$-alkoxy, $C_1$-$C_4$-haloalkyl or $C_1$-$C_4$-haloalkoxy, A and B and the carbon atom (3'- or 4'-position) to which they are attached preferably represent a tetrahydrofuran ring or tetrahydropyran ring which is optionally mono- or disubstituted by $C_1$-$C_6$-alkyl, $C_1$-$C_4$-haloalkyl, $C_1$-$C_6$-alkoxy or $C_1$-$C_4$-alkoxy-$C_1$-$C_4$-alkyl, D preferably represents NH (1) or oxygen (2), $Q^1$ and $Q^2$ independently of one another preferably represent hydrogen, $C_1$-$C_6$-alkyl, $C_1$-$C_2$-haloalkyl or $C_1$-$C_4$-alkoxy, G preferably represents hydrogen (a) or represents one of the groups

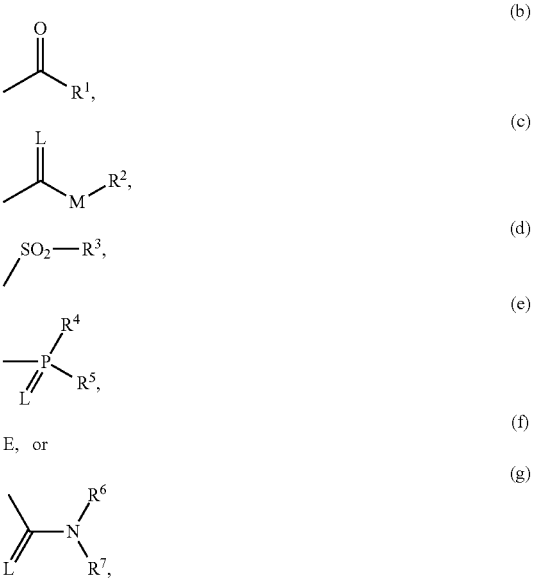

in which

E represents a metal ion or an ammonium ion,

L represents oxygen or sulphur and

M represents oxygen or sulphur, $R^1$ preferably represents in each case optionally halogen- or cyano-substituted $C_1$-$C_{20}$-alkyl, $C_2$-$C_{20}$-alkenyl, $C_1$-$C_8$-alkoxy-$C_1$-$C_8$-alkyl, $C_1$-$C_8$-alkylthio-$C_1$-$C_8$-alkyl or poly-$C_1$-$C_8$-alkoxy-$C_1$-$C_8$-alkyl or represents optionally halogen-, $C_1$-$C_6$-alkyl- or $C_1$-$C_6$-alkoxy-substituted $C_3$-$C_8$-cycloalkyl in which optionally one or two not directly adjacent methylene groups are replaced by oxygen and/or sulphur, represents optionally halogen-, cyano-, nitro-, $C_1$-$C_6$-alkyl-, $C_1$-$C_6$-alkoxy-, $C_1$-$C_6$-haloalkyl-, $C_1$-$C_6$-haloalkoxy-, $C_1$-$C_6$-alkylthio- or $C_1$-$C_6$-alkylsulphonyl-substituted phenyl, represents optionally halogen-, nitro-, cyano-, $C_1$-$C_6$-alkyl-, $C_1$-$C_6$-alkoxy-, $C_1$-$C_6$-haloalkyl- or $C_1$-$C_6$-haloalkoxy-substituted phenyl-$C_1$-$C_6$-alkyl, represents optionally halogen- or $C_1$-$C_6$-alkyl-substituted 5- or 6-membered hetaryl having one or two heteroatoms from the group consisting of oxygen, sulphur and nitrogen, represents optionally halogen- or $C_1$-$C_6$-alkyl-substituted phenoxy-$C_1$-$C_6$-alkyl or represents optionally halogen-, amino- or $C_1$-$C_6$-alkyl-substituted 5- or 6-membered hetaryloxy-$C_1$-$C_6$-alkyl having one or two heteroatoms from the group consisting of oxygen, sulphur and nitrogen, $R^2$ preferably represents in each case optionally halogen- or cyano-substituted $C_1$-$C_{20}$-alkyl, $C_2$-$C_{20}$-alkenyl, $C_1$-$C_8$-alkoxy-$C_2$-$C_8$-alkyl or poly-$C_1$-$C_8$-alkoxy-$C_2$-$C_8$-alkyl, represents optionally halogen-, $C_1$-$C_6$-alkyl- or $C_1$-$C_6$-alkoxy-substituted $C_3$-$C_8$-cycloalkyl or represents in each case optionally halogen-, cyano-, nitro-, $C_1$-$C_6$-alkyl-, $C_1$-$C_6$-alkoxy-, $C_1$-$C_6$-haloalkyl- or $C_1$-$C_6$-haloalkoxy-substituted phenyl or benzyl, $R^3$ preferably represents optionally halogen-substituted $C_1$-$C_8$-alkyl or in each case optionally halogen-, $C_1$-$C_6$-alkyl-, $C_1$-$C_6$-alkoxy-, $C_1$-$C_4$-haloalkyl-, $C_1$-$C_4$-haloalkoxy-, cyano- or nitro-substituted phenyl or benzyl, $R^4$ and $R^5$ independently of one another preferably represent in each case optionally halogen-substituted $C_1$-$C_8$-alkyl, $C_1$-$C_8$-alkoxy, $C_1$-$C_8$-alkylamino, di-($C_1$-$C_8$-alkyl)amino, $C_1$-$C_8$-alkylthio or $C_3$-$C_8$-alkenylthio or represent in each case optionally halogen-, nitro-, cyano-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkyl- or $C_1$-$C_4$-haloalkyl-substituted phenyl, phenoxy or phenylthio, $R^6$ and $R^7$ independently of one another preferably represent hydrogen, in each case optionally halogen- or cyano-substituted $C_1$-$C_8$-alkyl, $C_3$-$C_8$-cycloalkyl, $C_1$-$C_8$-alkoxy, $C_3$-$C_8$-alkenyl or $C_1$-$C_8$-alkoxy-$C_2$-$C_8$-alkyl, represent in each case optionally halogen-, $C_1$-$C_8$-alkyl-, $C_1$-$C_8$-haloalkyl- or $C_1$-$C_8$-alkoxy-substituted phenyl or benzyl or together represent an optionally $C_1$-$C_6$-alkyl-substituted $C_3$-$C_6$-alkylene radical in which optionally one methylene group is replaced by oxygen or sulphur.

In the radical definitions mentioned as being preferred, halogen represents fluorine, chlorine, bromine and iodine, in particular fluorine, chlorine and bromine.

W particularly preferably represents hydrogen, chlorine, bromine, $C_1$-$C_4$-alkyl, $C_2$-$C_4$-alkenyl, $C_2$-$C_4$-alkynyl, represents $C_3$-$C_6$-cycloalkyl which is optionally monosubstituted by methyl, ethyl, methoxy, fluorine, chlorine, trifluoromethyl or cyclopropyl, represents $C_1$-$C_4$-alkoxy, $C_1$-$C_2$-haloalkyl or $C_1$-$C_2$-haloalkoxy, X particularly preferably represents chlorine, bromine, $C_1$-$C_4$-alkyl, $C_2$-$C_4$-alkenyl, $C_2$-$C_4$-alkynyl, represents $C_3$-$C_6$-cycloalkyl which is optionally monosubstituted by methyl, ethyl, methoxy, fluorine, chlorine, trifluoromethyl or cyclopropyl, represents $C_1$-$C_4$-alkoxy, $C_1$-$C_4$-haloalkyl, $C_1$-$C_4$-haloalkoxy or cyano, Y and Z independently of one another particularly preferably represent hydrogen, fluorine, chlorine, bromine, iodine, $C_1$-$C_4$-alkyl, $C_2$-$C_4$-alkenyl, $C_2$-$C_4$-alkynyl, represent $C_3$-$C_6$-cycloalkyl which is optionally monosubstituted by methyl, ethyl, methoxy, fluorine, chlorine, trifluoromethyl or cyclopropyl, represents $C_1$-$C_6$-alkoxy, $C_1$-$C_4$-haloalkyl, $C_1$-$C_4$-haloalkoxy, cyano, $C_2$-$C_4$-alkenyl, $C_2$-$C_4$-alkynyl or represent one of the (het)aryl radicals

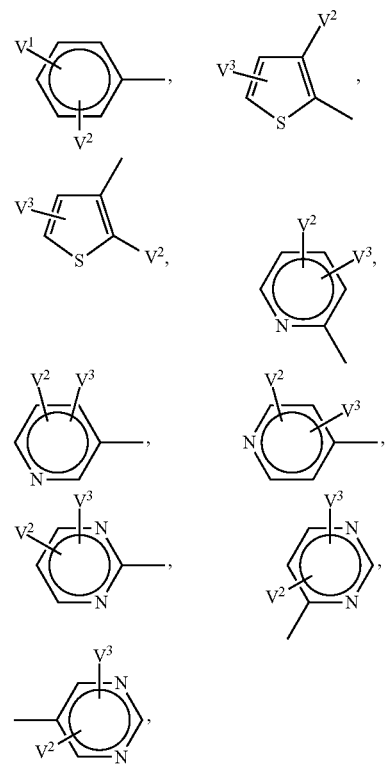

where in the case of (het)aryl only one of the radicals Y or Z may represent (het)aryl, $V^1$ particularly preferably represents hydrogen, fluorine, chlorine, bromine, $C_1$-$C_6$-alkyl, $C_1$-$C_4$-alkoxy, $C_1$-$C_2$-haloalkyl, $C_1$-$C_2$-haloalkoxy, nitro, cyano or represents phenyl which is optionally mono- or disubstituted by fluorine, chlorine, bromine, $C_1$-$C_4$-alkyl, $C_1$-$C_4$-alkoxy, $C_1$-$C_2$-haloalkyl, $C_1$-$C_2$-haloalkoxy, nitro or cyano, $V^2$ and $V^3$ independently of one another particularly preferably represent hydrogen, fluorine, chlorine, bromine, $C_1$-$C_4$-alkyl, $C_1$-$C_4$-alkoxy, $C_1$-$C_2$-haloalkyl or $C_1$-$C_2$-haloalkoxy, A and B and the carbon atom (3'- or 4'-position) to which they are attached particularly preferably represent a tetrahydrofuran ring or tetrahydropyran ring which is optionally monosubstituted by $C_1$-$C_4$-alkyl, $C_1$-$C_3$-haloalkyl, $C_1$-$C_4$-alkoxy or $C_1$-$C_4$-alkoxy-$C_1$-$C_2$-alkyl, D particularly preferably represents NH (1) or oxygen (2), $Q^1$ and $Q^2$ independently of one another particularly preferably represent hydrogen, methyl, ethyl, trifluoromethyl, methoxy or ethoxy, G particularly preferably represents hydrogen (a) or represents one of the groups

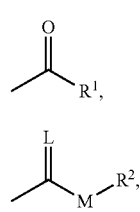

-continued

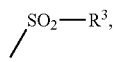
(d)

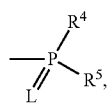
(e)

(f)
E, or

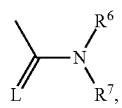
(g)

in which
E represents a metal ion or an ammonium ion,
L represents oxygen or sulphur and
M represents oxygen or sulphur,
$R^1$ particularly preferably represents $C_1$-$C_{16}$-alkyl, $C_2$-$C_{16}$-alkenyl, $C_1$-$C_6$-alkoxy-$C_1$-$C_4$-alkyl, $C_1$-$C_6$-alkylthio-$C_1$-$C_4$-alkyl or poly-$C_1$-$C_6$-alkoxy-$C_1$-$C_4$-alkyl, each of which is optionally mono- to trisubstituted by fluorine or chlorine, or represents $C_3$-$C_7$-cycloalkyl which is optionally mono- or disubstituted by fluorine, chlorine, $C_1$-$C_5$-alkyl or $C_1$-$C_5$-alkoxy and in which optionally one or two not directly adjacent methylene groups are replaced by oxygen and/or sulphur,
represents phenyl which is optionally mono- to trisubstituted by fluorine, chlorine, bromine, cyano, nitro, $C_1$-$C_4$-alkyl, $C_1$-$C_4$-alkoxy, $C_1$-$C_3$-haloalkyl, $C_1$-$C_3$-haloalkoxy, $C_1$-$C_4$-alkylthio or $C_1$-$C_4$-alkylsulphonyl,
represents phenyl-$C_1$-$C_4$-alkyl which is optionally mono- or disubstituted by fluorine, chlorine, bromine, $C_1$-$C_4$-alkyl, $C_1$-$C_4$-alkoxy, $C_1$-$C_3$-haloalkyl or $C_1$-$C_3$-haloalkoxy,
represents pyrazolyl, thiazolyl, pyridyl, pyrimidyl, furanyl or thienyl, each of which is optionally mono- or disubstituted by fluorine, chlorine, bromine or $C_1$-$C_4$-alkyl,
represents phenoxy-$C_1$-$C_5$-alkyl which is optionally mono- or disubstituted by fluorine, chlorine, bromine or $C_1$-$C_4$-alkyl or
represents pyridyloxy-$C_1$-$C_5$-alkyl, pyrimidyloxy-$C_1$-$C_5$-alkyl or thiazolyloxy-$C_1$-$C_5$-alkyl, each of which is optionally mono- or disubstituted by fluorine, chlorine, bromine, amino or $C_1$-$C_4$-alkyl,
$R^2$ particularly preferably represents $C_1$-$C_{16}$-alkyl, $C_2$-$C_{16}$-alkenyl, $C_1$-$C_6$-alkoxy-$C_2$-$C_6$-alkyl or poly-$C_1$-$C_6$-alkoxy-$C_2$-$C_6$-alkyl, each of which is optionally mono- to trisubstituted by fluorine or chlorine,
represents $C_3$-$C_7$-cycloalkyl which is optionally mono- or disubstituted by fluorine, chlorine, $C_1$-$C_4$-alkyl or $C_1$-$C_4$-alkoxy or
represents phenyl or benzyl, each of which is optionally mono- to trisubstituted by fluorine, chlorine, bromine, cyano, nitro, $C_1$-$C_4$-alkyl, $C_1$-$C_3$-alkoxy, $C_1$-$C_3$-haloalkyl or $C_1$-$C_3$-haloalkoxy,
$R^3$ particularly preferably represents $C_1$-$C_6$-alkyl which is optionally mono- to trisubstituted by fluorine or chlorine or represents phenyl or benzyl, each of which is optionally mono- or disubstituted by fluorine, chlorine, bromine, $C_1$-$C_4$-alkyl, $C_1$-$C_4$alkoxy, $C_1$-$C_2$-haloalkoxy, $C_1$-$C_2$-haloalkyl, cyano or nitro, $R^4$ and $R^5$ independently of one another particularly preferably represent $C_1$-$C_6$-alkyl, $C_1$-$C_6$-alkoxy, $C_1$-$C_6$-alkylamino, di-($C_1$-$C_6$-alkyl)amino, $C_1$-$C_6$-alkylthio or $C_3$-$C_4$-alkenylthio, each of which is optionally mono- to trisubstituted by fluorine or chlorine, or represent phenyl, phenoxy or phenylthio, each of which is optionally mono- or disubstituted by fluorine, chlorine, bromine, nitro, cyano, $C_1$-$C_3$-alkoxy, $C_1$-$C_3$-haloalkoxy, $C_1$-$C_3$-alkylthio, $C_1$-$C_3$-haloalkylthio, $C_1$-$C_3$-alkyl or $C_1$-$C_3$-haloalkyl,
$R^6$ and $R^7$ independently of one another particularly preferably represent hydrogen, represent $C_1$-$C_6$-alkyl, $C_3$-$C_6$-cycloalkyl, $C_1$-$C_6$-alkoxy, $C_3$-$C_6$-alkenyl or $C_1$-$C_6$-alkoxy-$C_2$-$C_6$-alkyl, each of which is optionally mono- to trisubstituted by fluorine or chlorine, represent phenyl or benzyl, each of which is optionally mono- to trisubstituted by fluorine, chlorine, bromine, $C_1$-$C_5$-haloalkyl, $C_1$-$C_5$-alkyl or $C_1$-$C_5$-alkoxy, or together represent an optionally $C_1$-$C_4$-alkyl-substituted $C_3$-$C_6$-alkylene radical in which optionally one methylene group is replaced by oxygen or sulphur.

In the radical definitions mentioned as being particularly preferred, halogen represents fluorine, chlorine and bromine, in particular fluorine and chlorine.

W very particularly preferably represents hydrogen, chlorine, bromine, methyl, ethyl, vinyl, ethynyl, propynyl, cyclopropyl, methoxy, ethoxy or trifluoromethyl, X very particularly preferably represents chlorine, bromine, methyl, ethyl, propyl, isopropyl, vinyl, ethynyl, propynyl, cyclopropyl, methoxy, ethoxy, trifluoromethyl, difluoromethoxy, trifluoromethoxy or cyano, Y and Z independently of one another very particularly preferably represent hydrogen, fluorine, chlorine, bromine, iodine, methyl, ethyl, vinyl, ethynyl, propynyl, cyclopropyl, methoxy, trifluoromethyl, trifluoromethoxy, cyano or a phenyl radical,

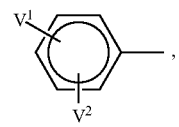

where in the case of phenyl only one of the radicals Y or Z may represent phenyl, $V^1$ very particularly preferably represents hydrogen, fluorine, chlorine, bromine, methyl, ethyl, n-propyl, isopropyl, tert-butyl, methoxy, ethoxy, n-propoxy, isopropoxy, trifluoromethyl or trifluoromethoxy, $V^2$ very particularly preferably represents hydrogen, fluorine, chlorine, methyl, ethyl, n-propyl, isopropyl, methoxy, ethoxy or trifluoromethyl, A and B and the carbon atom (3'- or 4'-position) to which they are attached very particularly preferably represent a tetrahydrofuran ring or tetrahydropyran ring which is optionally monosubstituted by methyl, ethyl, propyl, trifluoromethyl, methoxy, ethoxy, methoxymethyl or ethoxymethyl, D very particularly preferably represents NH (1) or oxygen (2), $Q^1$ and $Q^2$ very particularly preferably represent hydrogen, G very particularly preferably represents hydrogen (a) or represents one of the groups

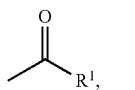 (b)

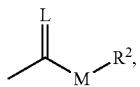 (c)

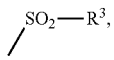 (d)

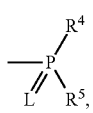 (e)

E, or (f)

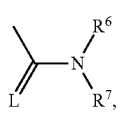 (g)

in which

E represents a metal ion or an ammonium ion,

L represents oxygen or sulphur and

M represents oxygen or sulphur, $R^1$ very particularly preferably represents $C_1$-$C_{10}$-alkyl, $C_2$-$C_{10}$-alkenyl, $C_1$-$C_4$-alkoxy-$C_1$-$C_2$-alkyl, $C_1$-$C_4$-alkylthio-$C_1$-$C_2$-alkyl, each of which is optionally mono- to trisubstituted by fluorine or chlorine, or represents $C_3$-$C_6$-cycloalkyl which is optionally monosubstituted by fluorine, chlorine, methyl, ethyl or methoxy,
represents phenyl which is optionally mono- or disubstituted by fluorine, chlorine, bromine, cyano, nitro, methyl, ethyl, n-propyl, isopropyl, methoxy, ethoxy, trifluoromethyl or trifluoromethoxy,
represents furanyl, thienyl or pyridyl, each of which is optionally monosubstituted by chlorine, bromine or methyl, $R^2$ very particularly preferably represents $C_1$-$C_{10}$-alkyl, $C_2$-$C_{10}$-alkenyl or $C_1$-$C_4$-alkoxy-$C_2$-$C_4$-alkyl, each of which is optionally mono- to trisubstituted by fluorine or chlorine,
represents cyclopentyl or cyclohexyl
or represents phenyl or benzyl, each of which is optionally mono- or disubstituted by fluorine, chlorine, cyano, nitro, methyl, ethyl, methoxy, trifluoromethyl or trifluoromethoxy, $R^3$ very particularly preferably represents methyl, ethyl, propyl or isopropyl, each of which is optionally mono- to trisubstituted by fluorine or chlorine, or represents phenyl which is optionally monosubstituted by fluorine, chlorine, bromine, methyl, ethyl, isopropyl, tert-butyl, methoxy, ethoxy, isopropoxy, trifluoromethyl, trifluoromethoxy, cyano or nitro, $R^4$ and $R^5$ independently of one another very particularly preferably represent $C_1$-$C_4$-alkoxy or $C_1$-$C_4$-alkylthio or represent phenyl, phenoxy or phenylthio, each of which is optionally monosubstituted by fluorine, chlorine, bromine, nitro, cyano, methyl, methoxy, trifluoromethyl or trifluoromethoxy, $R^6$ and $R^7$ independently of one another very particularly preferably represent hydrogen, represent $C_1$-$C_4$-alkyl, $C_3$-$C_6$-cycloalkyl, $C_1$-$C_4$-alkoxy, $C_3$-$C_4$-alkenyl or $C_1$-$C_4$-alkoxy-$C_2$-$C_4$-alkyl, represent phenyl which is optionally mono- or disubstituted by fluorine, chlorine, bromine, methyl, methoxy or trifluoromethyl, or together represent a $C_5$-$C_6$-alkylene radical in which optionally one methylene group is replaced by oxygen or sulphur.

W especially preferably represents hydrogen, chlorine, bromine, methyl, ethyl or methoxy, X especially preferably represents chlorine, bromine, methyl, ethyl or methoxy, Y and Z independently of one another especially preferably represent hydrogen, chlorine, bromine, methyl or represent the radical

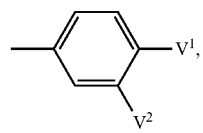

where in this case only one of the radicals Y or Z may represent

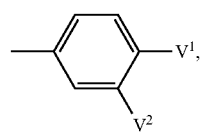

$V^1$ especially preferably represents fluorine or chlorine, $V^2$ especially preferably represents hydrogen, fluorine or chlorine, A and B and the carbon atom (4'-position) to which they are attached especially preferably represent a tetrahydrofuran ring which is optionally monosubstituted by methyl, ethyl, propyl or methoxymethyl, D especially preferably represents NH (1) or oxygen (2), $Q^1$ and $Q^2$ especially preferably represent hydrogen, G especially preferably represents hydrogen (a) or represents one of the groups

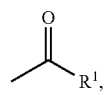 (b)

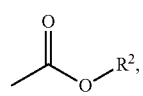 (c)

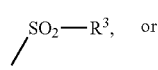 (d)

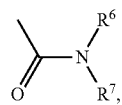 (g)

$R^1$ especially preferably represents $C_1$-$C_{10}$-alkyl, $C_1$-$C_4$-alkoxy-$C_1$-$C_2$-alkyl, $C_3$-$C_6$-cycloalkyl,
represents phenyl which is optionally monosubstituted by chlorine, or represents thienyl, $R^2$ especially preferably represents $C_1$-$C_{10}$-alkyl, $C_2$-$C_{10}$-alkenyl, or represents benzyl, R³ especially preferably represents methyl,
R⁶ and R⁷ together especially preferably represent a $C_5$-$C_6$-alkylene radical in which optionally one methylene group is replaced by oxygen or sulphur.
W very especially preferably represents hydrogen, chlorine, bromine, methyl or ethyl,
X very especially preferably represents chlorine, bromine, methyl, ethyl, methoxy, ethoxy or cyclopropyl,
Y very especially preferably represents hydrogen, methyl, ethyl, chlorine, bromine, iodine, fluorine, trifluoromethoxy or cyclopropyl,
Z very especially preferably represents hydrogen, bromine, methyl or the radicals

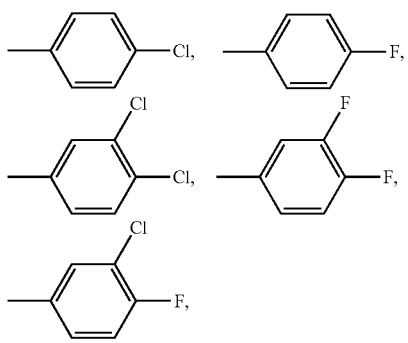

A and B and the carbon atom (4'-position) to which they are attached very especially preferably represent

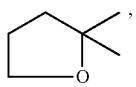,

D very especially preferably represents NH (1) or oxygen (2),
Q¹ and Q² very especially preferably represent hydrogen,
G very especially preferably represents hydrogen (a) or one of the groups

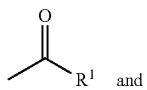 and

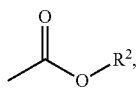

R¹ very especially preferably represents $C_1$-$C_6$-alkyl, $C_1$-$C_4$-alkoxy-$C_1$-$C_2$-alkyl or cyclopropyl,
R² very especially preferably represents $C_1$-$C_6$-alkyl or benzyl.

The general or preferred radical definitions or illustrations listed above can be combined with one another as desired, i.e. including combinations between the respective ranges and preferred ranges. They apply both to the end products and, correspondingly, to precursors and intermediates.

Preference according to the invention is given to the compounds of the formula (I) which contain a combination of the meanings listed above as being preferred (preferable).

Particular preference according to the invention is given to the compounds of the formula (I) which contain a combination of the meanings listed above as being particularly preferred.

Very particular preference according to the invention is given to the compounds of the formula (I) which contain a combination of the meanings listed above as being very particularly preferred.

Special preference according to the invention is given to the compounds of the formula (I) which contain a combination of the meanings listed above as being especially preferred.

Emphasis is given to the compounds of the formula (I) in which G represents hydrogen.

Saturated or unsaturated hydrocarbon radicals, such as alkyl, alkanediyl or alkenyl, can in each case be straight-chain or branched as far as this is possible, including in combination with heteroatoms, such as, for example, an alkoxy.

Unless indicated otherwise, optionally substituted radicals may be mono- or polysubstituted, where in the case of polysubstitutions the substituents may be identical or different.

In addition to the compounds mentioned in the Preparation Examples, the following compounds of the formula (I-1-a) may be specifically mentioned:

TABLE 1

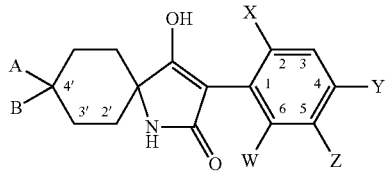

(I-1-a)

| A—B | X | W | Y | Z |
|---|---|---|---|---|
| —O—(CH₂)₃— | CH₃ | H | H | H |
| —O—(CH₂)₃— | Br | H | H | H |
| —O—(CH₂)₃— | Cl | H | H | H |
| —O—(CH₂)₃— | CF₃ | H | H | H |
| —O—(CH₂)₃— | OCH₃ | H | H | H |
| —O—(CH₂)₃— | Br | H | Cl | H |
| —O—(CH₂)₃— | Cl | H | Br | H |
| —O—(CH₂)₃— | Cl | H | Cl | H |
| —O—(CH₂)₃— | Cl | H | CH₃ | H |
| —O—(CH₂)₃— | CH₃ | H | Cl | H |
| —O—(CH₂)₃— | Cl | Cl | H | H |
| —O—(CH₂)₃— | Cl | OCH₃ | H | H |
| —O—(CH₂)₃— | Cl | CH₃ | H | H |
| —O—(CH₂)₃— | Cl | OC₂H₅ | H | H |
| —O—(CH₂)₃— | OCH₃ | OCH₃ | H | H |
| —O—(CH₂)₃— | CH₃ | CH₃ | H | H |
| —O—(CH₂)₃— | C₂H₅ | CH₃ | H | H |
| —O—(CH₂)₃— | C₂H₅ | C₂H₅ | H | H |
| —O—(CH₂)₃— | Br | CH₃ | Br | H |
| —O—(CH₂)₃— | Cl | CH₃ | Cl | H |
| —O—(CH₂)₃— | CH₃ | Br | CH₃ | H |
| —O—(CH₂)₃— | CH₃ | Cl | CH₃ | H |
| —O—(CH₂)₃— | OCH₃ | CH₃ | CH₃ | H |
| —O—(CH₂)₃— | OC₂H₅ | CH₃ | CH₃ | H |
| —O—(CH₂)₃— | OC₃H₇ | CH₃ | CH₃ | H |
| —O—(CH₂)₃— | CH₃ | CH₃ | CH₃ | H |
| —O—(CH₂)₃— | Br | Br | CH₃ | H |
| —O—(CH₂)₃— | Cl | Cl | CH₃ | H |
| —O—(CH₂)₃— | CH₃ | CH₃ | Br | H |
| —O—(CH₂)₃— | OCH₃ | C₂H₅ | CH₃ | H |
| —O—(CH₂)₃— | OC₂H₅ | C₂H₅ | CH₃ | H |
| —O—(CH₂)₃— | CH₃ | CH₃ | OCH₃ | H |
| —O—(CH₂)₃— | Br | Cl | CH₃ | H |
| —O—(CH₂)₃— | Br | CH₃ | Cl | H |
| —O—(CH₂)₃— | Cl | CH₃ | Br | H |

TABLE 1-continued (I-1-a)

| A—B | X | W | Y | Z |
|---|---|---|---|---|
| —O—(CH$_2$)$_3$— | CH$_3$ | CH$_3$ | Cl | H |
| —O—(CH$_2$)$_3$— | C$_2$H$_5$ | CH$_3$ | CH$_3$ | H |
| —O—(CH$_2$)$_3$— | C$_2$H$_5$ | C$_2$H$_5$ | CH$_3$ | H |
| —O—(CH$_2$)$_3$— | C$_2$H$_5$ | CH$_3$ | C$_2$H$_5$ | H |
| —O—(CH$_2$)$_3$— | C$_2$H$_5$ | C$_2$H$_5$ | C$_2$H$_5$ | H |
| —O—(CH$_2$)$_3$— | C$_2$H$_5$ | CH$_3$ | Cl | H |
| —O—(CH$_2$)$_3$— | C$_2$H$_5$ | C$_2$H$_5$ | Cl | H |
| —O—(CH$_2$)$_3$— | C$_2$H$_5$ | CH$_3$ | Br | H |
| —O—(CH$_2$)$_3$— | C$_2$H$_5$ | C$_2$H$_5$ | Br | H |
| —O—(CH$_2$)$_3$— | C$_2$H$_5$ | Cl | CH$_3$ | H |
| —O—(CH$_2$)$_3$— | C$_2$H$_5$ | Br | CH$_3$ | H |
| —O—(CH$_2$)$_3$— | C$_2$H$_5$ | Cl | Cl | H |
| —O—(CH$_2$)$_3$— | C$_2$H$_5$ | Br | Br | H |
| —O—(CH$_2$)$_3$— | C$_2$H$_5$ | Cl | Br | H |
| —O—(CH$_2$)$_3$— | C$_2$H$_5$ | Br | Cl | H |
| —O—(CH$_2$)$_3$— | OCH$_3$ | CH$_3$ | Cl | H |
| —O—(CH$_2$)$_3$— | OCH$_3$ | C$_2$H$_5$ | Cl | H |
| —O—(CH$_2$)$_3$— | OC$_2$H$_5$ | CH$_3$ | Cl | H |
| —O—(CH$_2$)$_3$— | OC$_2$H$_5$ | C$_2$H$_5$ | Cl | H |
| —O—(CH$_2$)$_3$— | Cl | OCH$_3$ | CH$_3$ | H |
| —O—(CH$_2$)$_3$— | Cl | OC$_2$H$_5$ | CH$_3$ | H |
| —O—(CH$_2$)$_3$— | CH$_3$ | CH$_3$ | Cl | H |
| —O—(CH$_2$)$_3$— | Cl | H | Cl | Cl |
| —O—(CH$_2$)$_3$— | CH$_3$ | H | CH$_3$ | CH$_3$ |
| —O—(CH$_2$)$_3$— | CH$_3$ | H | Cl | CH$_3$ |
| —O—(CH$_2$)$_3$— | Br | H | Cl | CH$_3$ |
| —O—(CH$_2$)$_3$— | Br | H | CH$_3$ | CH$_3$ |
| —O—(CH$_2$)$_3$— | Cl | H | Br | CH$_3$ |
| —O—(CH$_2$)$_3$— | Cl | H | Cl | CH$_3$ |
| —O—(CH$_2$)$_3$— | CH$_3$ | H | Br | CH$_3$ |
| —O—(CH$_2$)$_3$— | Cl | H | CH$_3$ | Cl |
| —O—(CH$_2$)$_3$— | CH$_3$ | H | H | CH$_3$ |
| —O—(CH$_2$)$_3$— | Cl | H | H | CH$_3$ |
| —O—(CH$_2$)$_3$— | Br | H | H | CH$_3$ |
| —O—(CH$_2$)$_3$— | CH$_3$ | H | H | Cl |
| —O—(CH$_2$)$_3$— | CH$_3$ | H | H | Br |
| —O—(CH$_2$)$_3$— | CH$_3$ | CH$_3$ | CH$_3$ | CH$_3$ |
| —O—(CH$_2$)$_3$— | CH$_3$ | CH$_3$ | CH$_3$ | F |
| —O—(CH$_2$)$_3$— | CH$_3$ | CH$_3$ | CH$_3$ | Cl |
| —O—(CH$_2$)$_3$— | CH$_3$ | CH$_3$ | CH$_3$ | Br |
| —O—(CH$_2$)$_3$— | CH$_3$ | CH$_3$ | H | Cl |
| —O—(CH$_2$)$_3$— | CH$_3$ | CH$_3$ | H | Br |
| —O—(CH$_2$)$_3$— | Cl | Cl | H | Br |
| —O—(CH$_2$)$_3$— | CH$_3$ | CH$_3$ | 4-Cl—C$_6$H$_4$ | H |
| —O—(CH$_2$)$_3$— | C$_2$H$_5$ | CH$_3$ | 4-Cl—C$_6$H$_4$ | H |
| —O—(CH$_2$)$_3$— | C$_2$H$_5$ | C$_2$H$_5$ | 4-Cl—C$_6$H$_4$ | H |
| —O—(CH$_2$)$_3$— | Cl | CH$_3$ | 4-Cl—C$_6$H$_4$ | H |
| —O—(CH$_2$)$_3$— | Cl | C$_2$H$_5$ | 4-Cl—C$_6$H$_4$ | H |
| —O—(CH$_2$)$_3$— | CH$_3$ | H | H | 4-Cl—C$_6$H$_4$ |
| —O—(CH$_2$)$_3$— | CH$_3$ | CH$_3$ | H | 4-Cl—C$_6$H$_4$ |
| —O—(CH$_2$)$_3$— | CH$_3$ | H | CH$_3$ | 4-Cl—C$_6$H$_4$ |
| —O—(CH$_2$)$_3$— | CH$_3$ | CH$_3$ | CH$_3$ | 4-Cl—C$_6$H$_4$ |
| —O—(CH$_2$)$_3$— | Cl | H | H | 4-Cl—C$_6$H$_4$ |
| —O—(CH$_2$)$_3$— | I | H | H | H |
| —O—(CH$_2$)$_3$— | I | H | CH$_3$ | H |
| —O—(CH$_2$)$_3$— | I | CH$_3$ | H | H |
| —O—(CH$_2$)$_3$— | I | C$_2$H$_5$ | H | H |
| —O—(CH$_2$)$_3$— | CH$_3$ | H | H | I |
| —O—(CH$_2$)$_3$— | CH$_3$ | H | CH$_3$ | I |
| —O—(CH$_2$)$_3$— | I | CH$_3$ | CH$_3$ | H |
| —O—(CH$_2$)$_3$— | I | C$_2$H$_5$ | CH$_3$ | H |
| —O—(CH$_2$)$_3$— | I | CH$_3$ | Cl | H |
| —O—(CH$_2$)$_3$— | I | C$_2$H$_5$ | Cl | H |
| —O—(CH$_2$)$_3$— | I | Cl | CH$_3$ | H |
| —O—(CH$_2$)$_3$— | I | H | CH$_3$ | CH$_3$ |
| —O—(CH$_2$)$_3$— | CH$_3$ | H | I | H |
| —O—(CH$_2$)$_3$— | C$_2$H$_5$ | H | I | H |
| —O—(CH$_2$)$_3$— | CH$_3$ | CH$_3$ | I | H |
| —O—(CH$_2$)$_3$— | C$_2$H$_5$ | CH$_3$ | I | H |
| —O—(CH$_2$)$_3$— | C$_2$H$_5$ | C$_2$H$_5$ | I | H |
| —O—(CH$_2$)$_3$— | Cl | CH$_3$ | I | H |
| —O—(CH$_2$)$_3$— | Cl | C$_2$H$_5$ | I | H |
| —O—(CH$_2$)$_3$— | CH$_3$ | H | I | CH$_3$ |
| —O—(CH$_2$)$_3$— | CH$_3$ | CH$_3$ | H | I |
| —O—(CH$_2$)$_3$— | I | H | H | CH$_3$ |
| —O—(CH$_2$)$_3$— | C$_2$H$_5$ | H | H | H |
| —O—(CH$_2$)$_3$— | cyclopropyl | H | H | H |
| —O—(CH$_2$)$_3$— | cyclopropyl | CH$_3$ | H | H |
| —O—(CH$_2$)$_3$— | cyclopropyl | H | CH$_3$ | H |
| —O—(CH$_2$)$_3$— | cyclopropyl | C$_2$H$_5$ | H | H |
| —O—(CH$_2$)$_3$— | cyclopropyl | CH$_3$ | CH$_3$ | H |
| —O—(CH$_2$)$_3$— | cyclopropyl | C$_2$H$_5$ | CH$_3$ | H |
| —O—(CH$_2$)$_3$— | cyclopropyl | CH$_3$ | Cl | H |
| —O—(CH$_2$)$_3$— | cyclopropyl | C$_2$H$_5$ | Cl | H |
| —O—(CH$_2$)$_3$— | cyclopropyl | Cl | CH$_3$ | H |
| —O—(CH$_2$)$_3$— | CH$_3$ | H | cyclopropyl | H |
| —O—(CH$_2$)$_3$— | C$_2$H$_5$ | H | cyclopropyl | H |
| —O—(CH$_2$)$_3$— | CH$_3$ | CH$_3$ | cyclopropyl | H |
| —O—(CH$_2$)$_3$— | C$_2$H$_5$ | CH$_3$ | cyclopropyl | H |
| —O—(CH$_2$)$_3$— | C$_2$H$_5$ | C$_2$H$_5$ | cyclopropyl | H |
| —O—(CH$_2$)$_3$— | Cl | CH$_3$ | cyclopropyl | H |
| —O—(CH$_2$)$_3$— | Cl | C$_2$H$_5$ | cyclopropyl | H |

In addition to the compounds mentioned in the Preparation Examples, the following compounds of the formula (I-2-a) may be specifically mentioned:

TABLE 2

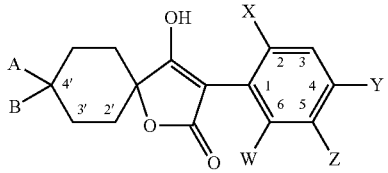

(I-2-a)

| A—B | X | W | Y | Z |
|---|---|---|---|---|
| —O—(CH₂)₃— | CH₃ | H | H | H |
| —O—(CH₂)₃— | Br | H | H | H |
| —O—(CH₂)₃— | Cl | H | H | H |
| —O—(CH₂)₃— | CF₃ | H | H | H |
| —O—(CH₂)₃— | OCH₃ | H | H | H |
| —O—(CH₂)₃— | Br | H | Cl | H |
| —O—(CH₂)₃— | Cl | H | Br | H |
| —O—(CH₂)₃— | Cl | H | Cl | H |
| —O—(CH₂)₃— | Cl | H | CH₃ | H |
| —O—(CH₂)₃— | CH₃ | H | Cl | H |
| —O—(CH₂)₃— | Cl | Cl | H | H |
| —O—(CH₂)₃— | Cl | OCH₃ | H | H |
| —O—(CH₂)₃— | Cl | CH₃ | H | H |
| —O—(CH₂)₃— | Cl | OC₂H₅ | H | H |
| —O—(CH₂)₃— | OCH₃ | OCH₃ | H | H |
| —O—(CH₂)₃— | CH₃ | CH₃ | H | H |
| —O—(CH₂)₃— | C₂H₅ | CH₃ | H | H |
| —O—(CH₂)₃— | C₂H₅ | C₂H₅ | H | H |
| —O—(CH₂)₃— | Br | CH₃ | Br | H |
| —O—(CH₂)₃— | Cl | CH₃ | Cl | H |
| —O—(CH₂)₃— | CH₃ | Br | CH₃ | H |
| —O—(CH₂)₃— | CH₃ | Cl | CH₃ | H |
| —O—(CH₂)₃— | OCH₃ | CH₃ | CH₃ | H |
| —O—(CH₂)₃— | OC₂H₅ | CH₃ | CH₃ | H |
| —O—(CH₂)₃— | OC₃H₇ | CH₃ | CH₃ | H |
| —O—(CH₂)₃— | CH₃ | CH₃ | CH₃ | H |
| —O—(CH₂)₃— | Br | Br | CH₃ | H |
| —O—(CH₂)₃— | Cl | Cl | CH₃ | H |
| —O—(CH₂)₃— | CH₃ | CH₃ | Br | H |
| —O—(CH₂)₃— | OCH₃ | C₂H₅ | CH₃ | H |
| —O—(CH₂)₃— | OC₂H₅ | C₂H₅ | CH₃ | H |
| —O—(CH₂)₃— | CH₃ | CH₃ | OCH₃ | H |
| —O—(CH₂)₃— | Br | Cl | CH₃ | H |
| —O—(CH₂)₃— | Br | CH₃ | Cl | H |
| —O—(CH₂)₃— | Cl | CH₃ | Br | H |
| —O—(CH₂)₃— | CH₃ | CH₃ | Cl | H |
| —O—(CH₂)₃— | C₂H₅ | CH₃ | CH₃ | H |
| —O—(CH₂)₃— | C₂H₅ | C₂H₅ | CH₃ | H |
| —O—(CH₂)₃— | C₂H₅ | CH₃ | C₂H₅ | H |
| —O—(CH₂)₃— | C₂H₅ | C₂H₅ | C₂H₅ | H |
| —O—(CH₂)₃— | C₂H₅ | CH₃ | Cl | H |
| —O—(CH₂)₃— | C₂H₅ | C₂H₅ | Cl | H |
| —O—(CH₂)₃— | C₂H₅ | CH₃ | Br | H |
| —O—(CH₂)₃— | C₂H₅ | C₂H₅ | Br | H |
| —O—(CH₂)₃— | C₂H₅ | Cl | CH₃ | H |
| —O—(CH₂)₃— | C₂H₅ | Br | CH₃ | H |
| —O—(CH₂)₃— | C₂H₅ | Cl | Cl | H |
| —O—(CH₂)₃— | C₂H₅ | Br | Br | H |
| —O—(CH₂)₃— | C₂H₅ | Cl | Br | H |
| —O—(CH₂)₃— | C₂H₅ | Br | Cl | H |
| —O—(CH₂)₃— | OCH₃ | CH₃ | Cl | H |
| —O—(CH₂)₃— | OCH₃ | C₂H₅ | Cl | H |
| —O—(CH₂)₃— | OC₂H₅ | CH₃ | Cl | H |
| —O—(CH₂)₃— | OC₂H₅ | C₂H₅ | Cl | H |
| —O—(CH₂)₃— | Cl | OCH₃ | CH₃ | H |
| —O—(CH₂)₃— | Cl | OC₂H₅ | CH₃ | H |
| —O—(CH₂)₃— | CH₃ | CH₃ | Cl | H |
| —O—(CH₂)₃— | Cl | H | Cl | Cl |
| —O—(CH₂)₃— | CH₃ | H | CH₃ | CH₃ |
| —O—(CH₂)₃— | CH₃ | H | Cl | CH₃ |
| —O—(CH₂)₃— | Br | H | Cl | CH₃ |
| —O—(CH₂)₃— | Br | H | CH₃ | CH₃ |
| —O—(CH₂)₃— | Cl | H | Br | CH₃ |
| —O—(CH₂)₃— | Cl | H | CH₃ | CH₃ |
| —O—(CH₂)₃— | CH₃ | H | Br | CH₃ |
| —O—(CH₂)₃— | Cl | H | CH₃ | Cl |
| —O—(CH₂)₃— | CH₃ | H | H | CH₃ |
| —O—(CH₂)₃— | Cl | H | H | CH₃ |

TABLE 2-continued

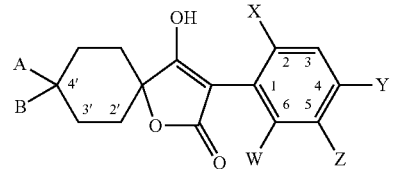

(I-2-a)

| A—B | X | W | Y | Z |
|---|---|---|---|---|
| —O—(CH₂)₃— | Br | H | H | CH₃ |
| —O—(CH₂)₃— | CH₃ | H | H | Cl |
| —O—(CH₂)₃— | CH₃ | H | H | Br |
| —O—(CH₂)₃— | CH₃ | CH₃ | CH₃ | CH₃ |
| —O—(CH₂)₃— | CH₃ | CH₃ | CH₃ | F |
| —O—(CH₂)₃— | CH₃ | CH₃ | CH₃ | Cl |
| —O—(CH₂)₃— | CH₃ | CH₃ | CH₃ | Br |
| —O—(CH₂)₃— | CH₃ | CH₃ | H | Cl |
| —O—(CH₂)₃— | CH₃ | CH₃ | H | Br |
| —O—(CH₂)₃— | Cl | Cl | H | Br |
| —O—(CH₂)₃— | CH₃ | CH₃ | 4-Cl—C₆H₄ | H |
| —O—(CH₂)₃— | C₂H₅ | CH₃ | 4-Cl—C₆H₄ | H |
| —O—(CH₂)₃— | C₂H₅ | C₂H₅ | 4-Cl—C₆H₄ | H |
| —O—(CH₂)₃— | Cl | CH₃ | 4-Cl—C₆H₄ | H |
| —O—(CH₂)₃— | Cl | C₂H₅ | 4-Cl—C₆H₄ | H |
| —O—(CH₂)₃— | CH₃ | H | H | 4-Cl—C₆H₄ |
| —O—(CH₂)₃— | CH₃ | CH₃ | H | 4-Cl—C₆H₄ |
| —O—(CH₂)₃— | CH₃ | H | CH₃ | 4-Cl—C₆H₄ |
| —O—(CH₂)₃— | CH₃ | CH₃ | CH₃ | 4-Cl—C₆H₄ |
| —O—(CH₂)₃— | Cl | H | H | 4-Cl—C₆H₄ |
| —O—(CH₂)₃— | I | H | H | H |
| —O—(CH₂)₃— | I | H | CH₃ | H |
| —O—(CH₂)₃— | I | CH₃ | H | H |
| —O—(CH₂)₃— | I | C₂H₅ | H | H |
| —O—(CH₂)₃— | CH₃ | H | H | I |
| —O—(CH₂)₃— | CH₃ | H | CH₃ | I |
| —O—(CH₂)₃— | I | CH₃ | CH₃ | H |
| —O—(CH₂)₃— | I | C₂H₅ | CH₃ | H |
| —O—(CH₂)₃— | I | CH₃ | Cl | H |
| —O—(CH₂)₃— | I | C₂H₅ | Cl | H |
| —O—(CH₂)₃— | I | Cl | CH₃ | H |
| —O—(CH₂)₃— | I | H | CH₃ | CH₃ |
| —O—(CH₂)₃— | CH₃ | H | I | H |
| —O—(CH₂)₃— | C₂H₅ | H | I | H |
| —O—(CH₂)₃— | CH₃ | CH₃ | I | H |
| —O—(CH₂)₃— | C₂H₅ | CH₃ | I | H |
| —O—(CH₂)₃— | C₂H₅ | C₂H₅ | I | H |
| —O—(CH₂)₃— | Cl | CH₃ | I | H |
| —O—(CH₂)₃— | Cl | C₂H₅ | I | H |
| —O—(CH₂)₃— | CH₃ | H | I | CH₃ |
| —O—(CH₂)₃— | CH₃ | CH₃ | H | I |
| —O—(CH₂)₃— | I | H | H | CH₃ |
| —O—(CH₂)₃— | △ | H | H | H |
| —O—(CH₂)₃— | △ | CH₃ | H | H |
| —O—(CH₂)₃— | △ | H | CH₃ | H |
| —O—(CH₂)₃— | △ | C₂H₅ | H | H |
| —O—(CH₂)₃— | △ | CH₃ | CH₃ | H |
| —O—(CH₂)₃— | △ | C₂H₅ | CH₃ | H |
| —O—(CH₂)₃— | △ | CH₃ | Cl | H |
| —O—(CH₂)₃— | △ | C₂H₅ | Cl | H |

TABLE 2-continued (I-2-a)

[Structure: spiro compound with OH, phenyl ring bearing X, Y, Z, W substituents, numbered positions 1-6 on phenyl and 2'-4' on cycloalkane ring, with A, B substituents]

| A—B | X | W | Y | Z |
|---|---|---|---|---|
| —O—(CH$_2$)$_3$— | △ | Cl | CH$_3$ | H |
| —O—(CH$_2$)$_3$— | CH$_3$ | H | △ | H |
| —O—(CH$_2$)$_3$— | C$_2$H$_5$ | H | △ | H |
| —O—(CH$_2$)$_3$— | CH$_3$ | CH$_3$ | △ | H |
| —O—(CH$_2$)$_3$— | C$_2$H$_5$ | CH$_3$ | △ | H |
| —O—(CH$_2$)$_3$— | C$_2$H$_5$ | C$_2$H$_5$ | △ | H |
| —O—(CH$_2$)$_3$— | Cl | CH$_3$ | △ | H |
| —O—(CH$_2$)$_3$— | Cl | C$_2$H$_5$ | △ | H |

Preferred definitions of the groups listed above in connection with the crop plant compatibility-improving compounds ("herbicide safeners") of the formulae (IIa), (IIb), (IIc), (IId) and (IIe) are defined below.

m preferably represents the numbers 0, 1, 2, 3 or 4.

$A^1$ preferably represents one of the divalent heterocyclic groupings shown below

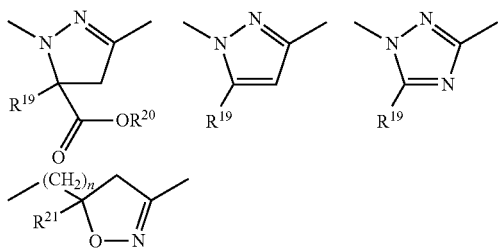

n preferably represents the numbers 0, 1, 2, 3 or 4.

$A^2$ preferably represents in each case optionally methyl-, ethyl-, methoxycarbonyl-, ethoxycarbonyl- or allyloxycarbonyl-substituted methylene or ethylene.

$R^{14}$ preferably represents hydroxyl, mercapto, amino, methoxy, ethoxy, n- or i-propoxy, n-, s- or t-butoxy, methylthio, ethylthio, n- or i-propylthio, n-, s- or t-butylthio, methylamino, ethylamino, n- or i-propylamino, n-, s- or t-butylamino, dimethylamino or diethylamino.

$R^{15}$ preferably represents hydroxyl, mercapto, amino, methoxy, ethoxy, n- or i-propoxy, n-, s- or t-butoxy, 1-methylhexyloxy, allyloxy, 1-allyloxymethylethoxy, methylthio, ethylthio, n- or i-propylthio, n-, s- or t-butylthio, methylamino, ethylamino, n- or i-propylamino, n-, s- or t-butylamino, dimethylamino or diethylamino.

$R^{16}$ preferably represents in each case optionally fluorine-, chlorine-, and/or bromine-substituted methyl, ethyl, n- or i-propyl.

$R^{17}$ preferably represents hydrogen, in each case optionally fluorine- and/or chlorine-substituted methyl, ethyl, n- or i-propyl, n-, s- or t-butyl, propenyl, butenyl, propynyl or butynyl, methoxymethyl, ethoxymethyl, methoxyethyl, ethoxyethyl, dioxolanylmethyl, furyl, furylmethyl, thienyl, thiazolyl, piperidinyl, or optionally fluorine-, chlorine-, methyl-, ethyl-, n- or i-propyl-, n-, s- or t-butyl-substituted phenyl.

$R^{18}$ preferably represents hydrogen, in each case optionally fluorine- and/or chlorine-substituted methyl, ethyl, n- or i-propyl, n-, s- or t-butyl, propenyl, butenyl, propynyl or butynyl, methoxymethyl, ethoxymethyl, methoxyethyl, ethoxyethyl, dioxolanylmethyl, furyl, furylmethyl, thienyl, thiazolyl, piperidinyl, or optionally fluorine-, chlorine-, methyl-, ethyl-, n- or i-propyl-, n-, s- or t-butyl-substituted phenyl, or together with $R^{17}$ represents one of the radicals —CH$_2$—O—CH$_2$—CH$_2$— and —CH$_2$—CH$_2$—O—CH$_2$—CH$_2$— which are optionally substituted by methyl, ethyl, furyl, phenyl, a fused benzene ring or by two substituents which, together with the C atom to which they are attached, form a 5- or 6-membered carbocycle.

$R^{19}$ preferably represents hydrogen, cyano, fluorine, chlorine, bromine, or represents in each case optionally fluorine-, chlorine- and/or bromine-substituted methyl, ethyl, n- or i-propyl, cyclo-propyl, cyclobutyl, cyclopentyl, cyclohexyl or phenyl.

$R^{20}$ preferably represents hydrogen, in each case optionally hydroxyl-, cyano-, fluorine-, chlorine-, methoxy-, ethoxy-, n- or i-propoxy-substituted methyl, ethyl, n- or i-propyl, n-, i-, s- or t-butyl.

$R^{21}$ preferably represents hydrogen, cyano, fluorine, chlorine, bromine, or represents in each case optionally fluorine-, chlorine- and/or bromine-substituted methyl, ethyl, n- or i-propyl, n-, i-, s- or t-butyl, cyclopropyl, cyclobutyl, cyclopentyl, cyclohexyl or phenyl.

$X^1$ preferably represents nitro, cyano, fluorine, chlorine, bromine, methyl, ethyl, n- or i-propyl, n-, i-, s- or t-butyl, difluoromethyl, dichloromethyl, trifluoromethyl, trichloromethyl, chlorodifluoromethyl, fluorodichloromethyl, methoxy, ethoxy, n- or i-propoxy, difluoromethoxy or trifluoromethoxy.

$X^2$ preferably represents hydrogen, nitro, cyano, fluorine, chlorine, bromine, methyl, ethyl, n- or i-propyl, n-, i-, s- or t-butyl, difluoromethyl, dichloromethyl, trifluoromethyl, trichloromethyl, chlorodifluoromethyl, fluorodichloromethyl, methoxy, ethoxy, n- or i-propoxy, difluoromethoxy or trifluoromethoxy.

$X^3$ preferably represents hydrogen, nitro, cyano, fluorine, chlorine, bromine, methyl, ethyl, n- or i-propyl, n-, i-, s- or t-butyl, difluoromethyl, dichloromethyl, trifluoromethyl, trichloromethyl, chlorodifluoromethyl, fluorodichloromethyl, methoxy, ethoxy, n- or i-propoxy, difluoromethoxy or trifluoromethoxy.

t preferably represents the numbers 0, 1, 2, 3 or 4.

v preferably represents the numbers 0, 1, 2, 3 or 4.

$R^{22}$ preferably represents hydrogen, methyl, ethyl, n- or i-propyl.

$R^{23}$ preferably represents hydrogen, methyl, ethyl, n- or i-propyl.

$R^{24}$ preferably represents hydrogen, in each case optionally cyano-, fluorine-, chlorine-, methoxy-, ethoxy-, n- or i-propoxy-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, dimethylamino or diethylamino, or in each case optionally cyano-, fluorine-, chlorine-, bromine-, methyl-, ethyl-, n- or i-propyl-substituted cyclopropyl, cyclobutyl, cyclopentyl, cyclohexyl, cyclopropyloxy, cyclobutyloxy, cyclopentyloxy, cyclohexyloxy, cyclopropylthio, cyclobutylthio, cyclopentylthio, cyclohexylthio, cyclopropylamino, cyclobutylamino, cyclopentylamino or cyclohexylamino.

$R^{25}$ preferably represents hydrogen, in each case optionally cyano-, hydroxyl-, fluorine-, chlorine-, methoxy-, ethoxy-, n- or i-propoxy-substituted methyl, ethyl, n- or i-propyl, n-, i- or s-butyl, in each case optionally cyano-, fluorine-, chlorine- or bromine-substituted propenyl, butenyl, propynyl or butynyl, or in each case optionally cyano-, fluorine-, chlorine-, bromine-, methyl-, ethyl-, n- or i-propyl-substituted cyclopropyl, cyclobutyl, cyclopentyl or cyclohexyl.

$R^{26}$ preferably represents hydrogen, in each case optionally cyano-, hydroxyl-, fluorine-, chlorine-, methoxy-, ethoxy-, n- or i-propoxy-substituted methyl, ethyl, n- or i-propyl, n-, i- or s-butyl, in each case optionally cyano-, fluorine-, chlorine- or bromine-substituted propenyl, butenyl, propynyl or butynyl, in each case optionally cyano-, fluorine-, chlorine-, bromine-, methyl-, ethyl-, n- or i-propyl-substituted cyclopropyl, cyclobutyl, cyclopentyl or cyclohexyl, or optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy- or trifluoromethoxy-substituted phenyl, or together with $R^{25}$ represents in each case optionally methyl- or ethyl-substituted butane-1,4-diyl(trimethylene), pentane-1,5-diyl, 1-oxabutane-1,4-diyl or 3-oxapentane-1,5-diyl.

$X^4$ preferably represents nitro, cyano, carboxyl, carbamoyl, formyl, sulphamoyl, hydroxyl, amino, fluorine, chlorine, bromine, methyl, ethyl, n- or i-propyl, n-, i-, s- or t-butyl, trifluoromethyl, methoxy, ethoxy, n- or i-propoxy, difluoromethoxy or trifluoromethoxy.

$X^5$ preferably represents nitro, cyano, carboxyl, carbamoyl, formyl, sulphamoyl, hydroxyl, amino, fluorine, chlorine, bromine, methyl, ethyl, n- or i-propyl, n-, i-, s- or t-butyl, trifluoromethyl, methoxy, ethoxy, n- or i-propoxy, difluoromethoxy or trifluoromethoxy.

Examples of the compounds of the formula (IIa) which are very particularly preferred as herbicide safeners according to the invention are listed in the table below.

TABLE

Examples of the compounds of the formula (IIa)

| Example No. | (Positions) $(X^1)_m$ | $A^1$ | $R^{14}$ |
|---|---|---|---|
| IIa-1 | (2) Cl, (4) Cl | (pyrazoline with H3C, CO-OCH3) | OCH3 |
| IIa-2 | (2) Cl, (4) Cl | (pyrazoline with H3C, CO-OC2H5) | OCH3 |
| IIa-3 | (2) Cl, (4) Cl | (pyrazoline with H3C, CO-OCH3) | OC2H5 |
| IIa-4 | (2) Cl, (4) Cl | (pyrazoline with H3C, CO-OC2H5) | OC2H5 |
| IIa-5 | (2) Cl | (phenyl-pyrazole) | OCH3 |
| IIa-6 | (2) Cl, (4) Cl | (phenyl-pyrazole) | OCH3 |
| IIa-7 | (2) F | (phenyl-pyrazole) | OCH3 |
| IIa-8 | (2) F | (chlorophenyl-pyrazole) | OCH3 |

TABLE-continued

Examples of the compounds of the formula (IIa)

(IIa)

$(X^1)_m$ — phenyl(4,2,3-positions)—$A^1$—C(=O)—$R^{14}$

| Example No. | (Positions) $(X^1)_m$ | $A^1$ | $R^{14}$ |
|---|---|---|---|
| IIa-9 | (2) Cl, (4) Cl | 1-methyl-3-methyl-5-(trichloromethyl)-1,2,4-triazol-yl | $OC_2H_5$ |
| IIa-10 | (2) Cl, (4) $CF_3$ | 1-methyl-3-methyl-5-phenyl-1,2,4-triazol-yl | $OCH_3$ |
| IIa-11 | (2) Cl | 1-methyl-3-methyl-5-(2-fluorophenyl)pyrazol-yl | $OCH_3$ |
| IIa-12 | — | 5-methyl-3-methyl-5-phenyl-isoxazolin-yl | $OC_2H_5$ |
| IIa-13 | (2) Cl, (4) Cl | 1-methyl-3-methyl-5-methyl-pyrazol-yl | $OC_2H_5$ |
| IIa-14 | (2) Cl, (4) Cl | 1-methyl-3-methyl-5-isopropyl-pyrazol-yl | $OC_2H_5$ |
| IIa-15 | (2) Cl, (4) Cl | 1-methyl-3-methyl-5-tert-butyl-pyrazol-yl | $OC_2H_5$ |
| IIa-16 | (2) Cl, (4) Cl | 3-methyl-5-ethyl-isoxazolin-yl | $OC_2H_5$ |
| IIa-17 | (2) Cl, (4) Cl | 3-methyl-5-methyl-isoxazolin-yl | $OC_2H_5$ |
| IIa-18 | — | 5-methyl-3-methyl-5-phenyl-isoxazolin-yl | OH |

Examples of the compounds of the formula (IIb) which are very particularly preferred as herbicide safeners according to the invention are listed in the table below.

TABLE

Examples of the compounds of the formula (IIb)

(IIb)

quinolin-8-yl-O-$A^2$-C(=O)-$R^{15}$ with $X^3$ at position 4 and $X^2$ at position 5

| Example No. | (Position) $X^2$ | (Position) $X^3$ | $A^2$ | $R^{15}$ |
|---|---|---|---|---|
| IIb-1 | (5) Cl | — | $CH_2$ | OH |
| IIb-2 | (5) Cl | — | $CH_2$ | $OCH_3$ |
| IIb-3 | (5) Cl | — | $CH_2$ | $OC_2H_5$ |
| IIb-4 | (5) Cl | — | $CH_2$ | $OC_3H_7$-n |
| IIb-5 | (5) Cl | — | $CH_2$ | $OC_3H_7$-i |
| IIb-6 | (5) Cl | — | $CH_2$ | $OC_4H_9$-n |
| IIb-7 | (5) Cl | — | $CH_2$ | $OCH(CH_3)C_5H_{11}$-n |
| IIb-8 | (5) Cl | (2) F | $CH_2$ | OH |
| IIb-9 | (5) Cl | (2) Cl | $CH_2$ | OH |
| IIb-10 | (5) Cl | — | $CH_2$ | $OCH_2CH{=}CH_2$ |
| IIb-11 | (5) Cl | — | $CH_2$ | $OC_4H_9$-i |
| IIb-12 | (5) Cl | — | $CH_2$ | $OCH_2CH(CH_2OCH_2CH{=}CH_2)OCH_3$ (methoxy-methoxy-allyl ether group) |
| IIb-13 | (5) Cl | — | $CH_2$-CH(allyl)-O-C(=O)-CH(CH_3)_2 | $OCH_2CH{=}CH_2$ |

TABLE-continued

Examples of the compounds of the formula (IIb)

(IIb)

| Example No. | (Position) $X^2$ | (Position) $X^3$ | $A^2$ | $R^{15}$ |
|---|---|---|---|---|
| IIb-14 | (5) Cl | — | (CH with C$_2$H$_5$, O-C(=O)-) | OC$_2$H$_5$ |
| IIb-15 | (5) Cl | — | (CH with CH$_3$, O-C(=O)-) | OCH$_3$ |

Examples of the compounds of the formula (IIc) which are very particularly preferred as herbicide safeners according to the invention are listed in the table below.

TABLE

Examples of the compounds of the formula (IIc)

(IIc)

| Example No. | $R^{16}$ | $N(R^{17}, R^{18})$ |
|---|---|---|
| IIc-1 | CHCl$_2$ | N(CH$_2$CH=CH$_2$)$_2$ |
| IIc-2 | CHCl$_2$ | 2,2-dimethyl-oxazolidinyl |
| IIc-3 | CHCl$_2$ | 2,2,5-trimethyl-oxazolidinyl |
| IIc-4 | CHCl$_2$ | 1-oxa-4-azaspiro[4.5]decyl |
| IIc-5 | CHCl$_2$ | 2,2-dimethyl-5-phenyl-oxazolidinyl |
| IIc-6 | CHCl$_2$ | 3-methyl-3,4-dihydro-2H-1,4-benzoxazinyl |
| IIc-7 | CHCl$_2$ | 2,2-dimethyl-5-(furan-2-yl)-oxazolidinyl |

Examples of the compounds of the formula (IId) which are very particularly preferred as herbicide safeners according to the invention are listed in the table below.

TABLE

Examples of the compounds of the formula (IId)

(IId)

| Example No. | $R^{22}$ | $R^{23}$ | $R^{24}$ | (Positions) $(X^4)_t$ | (Positions) $(X^5)_v$ |
|---|---|---|---|---|---|
| IId-1 | H | H | CH$_3$ | (2) OCH$_3$ | — |
| IId-2 | H | H | C$_2$H$_5$ | (2) OCH$_3$ | — |
| IId-3 | H | H | C$_3$H$_7$-n | (2) OCH$_3$ | — |
| IId-4 | H | H | C$_3$H$_7$-i | (2) OCH$_3$ | — |
| IId-5 | H | H | cyclopropyl | (2) OCH$_3$ | — |
| IId-6 | H | H | CH$_3$ | (2) OCH$_3$ (5) CH$_3$ | — |

Examples of the compounds of the formula (IId)

(IId)

| Example No. | $R^{22}$ | $R^{23}$ | $R^{24}$ | (Positions) $(X^4)_t$ | (Positions) $(X^5)_v$ |
|---|---|---|---|---|---|
| IId-7 | H | H | $C_2H_5$ | (2) $OCH_3$ (5) $CH_3$ | — |
| IId-8 | H | H | $C_3H_7$-n | (2) $OCH_3$ (5) $CH_3$ | — |
| IId-9 | H | H | $C_3H_7$-i | (2) $OCH_3$ (5) $CH_3$ | — |
| IId-10 | H | H |  | (2) $OCH_3$ (5) $CH_3$ | — |
| IId-11 | H | H | $OCH_3$ | (2) $OCH_3$ (5) $CH_3$ | — |
| IId-12 | H | H | $OC_2H_5$ | (2) $OCH_3$ (5) $CH_3$ | — |
| IId-13 | H | H | $OC_3H_7$-i | (2) $OCH_3$ (5) $CH_3$ | — |
| IId-14 | H | H | $SCH_3$ | (2) $OCH_3$ (5) $CH_3$ | — |
| IId-15 | H | H | $SC_2H_5$ | (2) $OCH_3$ (5) $CH_3$ | — |
| IId-16 | H | H | $SC_3H_7$-i | (2) $OCH_3$ (5) $CH_3$ | — |
| IId-17 | H | H | $NHCH_3$ | (2) $OCH_3$ (5) $CH_3$ | — |
| IId-18 | H | H | $NHC_2H_5$ | (2) $OCH_3$ (5) $CH_3$ | — |
| IId-19 | H | H | $NHC_3H_7$-i | (2) $OCH_3$ (5) $CH_3$ | — |
| IId-20 | H | H |  | (2) $OCH_3$ (5) $CH_3$ | — |
| IId-21 | H | H | $NHCH_3$ | (2) $OCH_3$ | — |
| IId-22 | H | H | $NHC_3H_7$-i | (2) $OCH_3$ | — |
| IId-23 | H | H | $N(CH_3)_2$ | (2) $OCH_3$ | — |
| IId-24 | H | H | $N(CH_3)_2$ | (3) $CH_3$ (4) $CH_3$ | — |
| IId-25 | H | H | $CH_2$—O—$CH_3$ | (2) $OCH_3$ | — |

Examples of the compounds of the formula (IIe) which are very particularly preferred as herbicide safeners according to the invention are listed in the table below.

Examples of the compounds of the formula (IIe)

(IIe)

| Example No. | $R^{22}$ | $R^{25}$ | $R^{26}$ | (Positions) $(X^4)_t$ | (Positions) $(X^5)_v$ |
|---|---|---|---|---|---|
| IIe-1 | H | H | $CH_3$ | (2) $OCH_3$ | — |
| IIe-2 | H | H | $C_2H_5$ | (2) $OCH_3$ | — |
| IIe-3 | H | H | $C_3H_7$-n | (2) $OCH_3$ | — |
| IIe-4 | H | H | $C_3H_7$-i | (2) $OCH_3$ | — |
| IIe-5 | H | H |  | (2) $OCH_3$ | — |
| IIe-6 | H | $CH_3$ | $CH_3$ | (2) $OCH_3$ | — |
| IIe-7 | H | H | $CH_3$ | (2) $OCH_3$ (5) $CH_3$ | — |
| IIe-8 | H | H | $C_2H_5$ | (2) $OCH_3$ (5) $CH_3$ | — |
| IIe-9 | H | H | $C_3H_7$-n | (2) $OCH_3$ (5) $CH_3$ | — |
| IIe-10 | H | H | $C_3H_7$-i | (2) $OCH_3$ (5) $CH_3$ | — |
| IIe-11 | H | H |  | (2) $OCH_3$ (5) $CH_3$ | — |
| IIe-12 | H | $CH_3$ | $CH_3$ | (2) $OCH_3$ (5) $CH_3$ | — |

Most preferred as crop plant compatibility-improving compound [component (b')] are cloquintocet-mexyl, fenchlorazole-ethyl, isoxadifen-ethyl, mefenpyr-diethyl, furilazole, fenclorim, cumyluron, dymron, dimepiperate and the compounds IIe-5 and IIe-11, and particular emphasis is given to cloquintocet-mexyl and mefenpyr-diethyl.

The compounds of the general formula (IIa) to be used as safeners according to the invention are known and/or can be prepared by processes known per se (cf. WO-A-91/07874, WO-A-95/07897).

The compounds of the general formula (IIb) to be used as safeners according to the invention are known and/or can be prepared by processes known per se (cf. EP-A-191736).

The compounds of the general formula (IIc) to be used as safeners according to the invention are known and/or can be prepared by processes known per se (cf. DE-A-2218097, DE-A-2350547).

The compounds of the general formula (IId) to be used as safeners according to the invention are known and/or can be prepared by processes known per se (cf. DE-A-19621522/ U.S. Pat. No. 6,235,680).

The compounds of the general formula (IIe) to be used as safeners according to the invention are known and can be prepared by processes known per se (cf. WO-A-99/66795/ U.S. Pat. No. 6,251,827).

Examples of the selective herbicidal combinations according to the invention comprising in each case one active compound of the formula (I) and in each case one of the safeners defined above are listed in the table below.

TABLE

Examples of combinations according to the invention

| Active compounds of the formula (I) | Safeners |
|---|---|
| I-1-a | cloquintocet-mexyl |
| I-1-a | fenchlorazole-ethyl |
| I-1-a | isoxadifen-ethyl |
| I-1-a | mefenpyr-diethyl |
| I-1-a | furilazole |
| I-1-a | fenclorim |
| I-1-a | cumyluron |
| I-1-a | daimuron/dymron |
| I-1-a | dimepiperate |
| I-1-a | IIe-11 |
| I-1-a | IIe-5 |
| I-1-b | cloquintocet-mexyl |
| I-1-b | fenchlorazole-ethyl |
| I-1-b | isoxadifen-ethyl |
| I-1-b | mefenpyr-diethyl |
| I-1-b | furilazole |
| I-1-b | fenclorim |
| I-1-b | cumyluron |
| I-1-b | daimuron/dymron |
| I-1-b | dimepiperate |
| I-1-b | IIe-11 |
| I-1-b | IIe-5 |
| I-1-c | cloquintocet-mexyl |
| I-1-c | fenchlorazole-ethyl |
| I-1-c | isoxadifen-ethyl |
| I-1-c | mefenpyr-diethyl |
| I-1-c | furilazole |
| I-1-c | fenclorim |
| I-1-c | cumyluron |
| I-1-c | daimuron/dymron |
| I-1-c | dimepiperate |
| I-1-c | IIe-5 |
| I-1-c | IIe-11 |
| I-1-d | cloquintocet-mexyl |
| I-1-d | fenchlorazole-ethyl |
| I-1-d | isoxadifen-ethyl |
| I-1-d | mefenpyr-diethyl |
| I-1-d | furilazole |
| I-1-d | fenclorim |
| I-1-d | cumyluron |
| I-1-d | daimuron/dymron |
| I-1-d | dimepiperate |
| I-1-d | IIe-11 |
| I-1-d | IIe-5 |
| I-1-e | cloquintocet-mexyl |
| I-1-e | fenchlorazole-ethyl |
| I-1-e | isoxadifen-ethyl |
| I-1-e | mefenpyr-diethyl |
| I-1-e | furilazole |
| I-1-e | fenclorim |
| I-1-e | cumyluron |
| I-1-e | daimuron/dymron |
| I-1-e | dimepiperate |
| I-1-e | IIe-5 |
| I-1-e | IIe-11 |
| I-1-f | cloquintocet-mexyl |
| I-1-f | fenchlorazole-ethyl |
| I-1-f | isoxadifen-ethyl |
| I-1-f | mefenpyr-diethyl |
| I-1-f | furilazole |
| I-1-f | fenclorim |
| I-1-f | cumyluron |
| I-1-f | daimuron/dymron |
| I-1-f | dimepiperate |
| I-1-f | IIe-5 |
| I-1-f | IIe-11 |
| I-1-g | cloquintocet-mexyl |
| I-1-g | fenchlorazole-ethyl |
| I-1-g | isoxadifen-ethyl |
| I-1-g | mefenpyr-diethyl |
| I-1-g | furilazole |
| I-1-g | fenclorim |
| I-1-g | cumyluron |
| I-1-g | daimuron/dymron |
| I-1-g | dimepiperate |
| I-1-g | IIe-5 |
| I-1-g | IIe-11 |
| I-2-a | cloquintocet-mexyl |
| I-2-a | fenchlorazole-ethyl |
| I-2-a | isoxadifen-ethyl |
| I-2-a | mefenpyr-diethyl |
| I-2-a | furilazole |
| I-2-a | fenclorim |
| I-2-a | cumyluron |
| I-2-a | daimuron/dymron |
| I-2-a | dimepiperate |
| I-2-a | IIe-5 |
| I-2-a | IIe-11 |
| I-2-b | cloquintocet-mexyl |
| I-2-b | fenchlorazole-ethyl |
| I-2-b | isoxadifen-ethyl |
| I-2-b | mefenpyr-diethyl |
| I-2-b | furilazole |
| I-2-b | fenclorim |
| I-2-b | cumyluron |
| I-2-b | daimuron/dymron |
| I-2-b | dimepiperate |
| I-2-b | IIe-5 |
| I-2-b | IIe-11 |
| I-2-c | cloquintocet-mexyl |
| I-2-c | fenchlorazole-ethyl |
| I-2-c | isoxadifen-ethyl |
| I-2-c | mefenpyr-diethyl |
| I-2-c | furilazole |
| I-2-c | fenclorim |
| I-2-c | cumyluron |
| I-2-c | daimuron/dymron |
| I-2-c | dimepiperate |
| I-2-c | IIe-5 |
| I-2-c | IIe-11 |
| I-2-d | cloquintocet-mexyl |
| I-2-d | fenchlorazole-ethyl |
| I-2-d | isoxadifen-ethyl |
| I-2-d | mefenpyr-diethyl |
| I-2-d | furilazole |
| I-2-d | fenclorim |
| I-2-d | cumyluron |
| I-2-d | daimuron/dymron |
| I-2-d | dimepiperate |
| I-2-d | IIe-5 |
| I-2-d | IIe-11 |
| I-2-e | cloquintocet-mexyl |
| I-2-e | fenchlorazole-ethyl |
| I-2-e | isoxadifen-ethyl |
| I-2-e | mefenpyr-diethyl |
| I-2-e | furilazole |
| I-2-e | fenclorim |
| I-2-e | cumyluron |
| I-2-e | daimuron/dymron |
| I-2-e | dimepiperate |
| I-2-e | IIe-5 |
| I-2-e | IIe-11 |
| I-2-f | cloquintocet-mexyl |
| I-2-f | fenchlorazole-ethyl |
| I-2-f | isoxadifen-ethyl |
| I-2-f | mefenpyr-diethyl |
| I-2-f | furilazole |
| I-2-f | fenclorim |
| I-2-f | cumyluron |
| I-2-f | daimuron/dymron |
| I-2-f | dimepiperate |
| I-2-f | IIe-5 |
| I-2-f | IIe-11 |
| I-2-g | cloquintocet-mexyl |
| I-2-g | fenchlorazole-ethyl |
| I-2-g | isoxadifen-ethyl |
| I-2-g | mefenpyr-diethyl |
| I-2-g | furilazole |
| I-2-g | fenclorim |
| I-2-g | cumyluron |

TABLE-continued

Examples of combinations according to the invention

| Active compounds of the formula (I) | Safeners |
|---|---|
| I-2-g | daimuron/dymron |
| I-2-g | dimepiperate |
| I-2-g | IIe-5 |
| I-2-g | IIe-11 |

Surprisingly, it has now been found that the active compound combinations defined above of compounds of the general formula (I) and safeners (antidotes) from the group (b') set out above combine very good useful plant tolerance with a particularly high herbicidal activity and can be used in various crops, in particular in cereals (especially wheat), but also in soya, potatoes, maize and rice, for the selective control of weeds.

In this context it is to be considered surprising that, from a multiplicity of known safeners or antidotes capable of antagonizing the damaging effect of a herbicide on the crop plants, it is specifically the compounds of group (b') set out above which are suitable for compensating—almost completely—the damaging effect of oxaspirocyclic spiro-substituted tetramic and tetronic acid derivatives on the crop plants, without at the same time having any critical adverse effect on the herbicidal activity against the weeds.

Emphasis may be given here to the particularly advantageous effect of the particularly preferred and most preferred combination partners from group (b'), in particular with regard to the gentle treatment of cereal plants, such as wheat, barley and rye, for example, but also maize and rice, as crop plants.

In the literature it has already been described how the action of various active compounds can be boosted by addition of ammonium salts. The salts in question, however, are detersive salts (e.g. WO 95/017817) or salts which have relatively long alkyl substituents and/or aryl substituents and which have a permeabilizing action or which increase the active compound's solubility (e.g. EP-A 0 453 086, EP-A 0 664 081, FR-A 2 600 494, U.S. Pat. No. 4,844,734, U.S. Pat. No. 5,462,912, U.S. Pat. No. 5,538,937, U.S. Ser. No. 03/0, 224,939, U.S. Ser. No. 05/0,009,880, U.S. Ser. No. 05/0,096, 386). Moreover, the prior art describes the action only for particular active compounds and/or particular applications of the corresponding compositions. In other cases, in turn, the salts in question are those of sulphonic acids, where the acids themselves have a paralytic action on insects (U.S. Pat. No. 2,842,476). A boost to action by ammonium sulphate, for example, is described by way of example for the herbicides glyphosate and phosphinothricin and for phenyl-substituted cyclic ketoenols (U.S. Pat. No. 6,645,914, EP-A2 0 036 106, WO 07/068427). A corresponding boost to action in the case of insecticides has already been described in WO 07/068428.

The use of ammonium sulphate as a formulating assistant has also been described for certain active compounds and applications (WO 92/16108), but its purpose therein is to stabilize the formulation, not to boost the action.

It has now been found, entirely surprisingly, that the action of insecticides and/or acaricides and/or herbicides from the class of the oxaspirocyclic spiro-substituted tetramic and tetronic acid derivatives can be boosted significantly through the addition of ammonium salts or phosphonium salts to the application solution or through the incorporation of these salts into a formulation comprising oxaspiroxylic spiro-substituted tetramic and tetronic acid derivatives. The present invention therefore provides for the use of ammonium salts or phosphonium salts for boosting the action of crop protection compositions which comprise as their active compound herbicidal and/or insecticidal and/or acaricidal oxaspirocyclic spiro-substituted tetramic and tetronic acid derivatives. The invention likewise provides compositions which comprise herbicidal and/or acaricidal and/or insecticidal oxaspirocyclic spiro-substituted tetramic and tetronic acid derivatives and action-boosting ammonium salts or phosphonium salts, including not only formulated active compounds but also ready-to-use compositions (spray liquors). The invention further provides, finally, for the use of these compositions for controlling insect pests and/or spider mites and/or unwanted plant growth.

The compounds of the formula (I) possess a broad insecticidal and/or acaricidal and/or herbicidal activity, but individually the activity and/or plant tolerance leaves something to be desired.

The active compounds can be used in the compositions of the invention in a broad concentration range. The concentration of the active compounds in the formulation is typically 0.1%-50% by weight.

Ammonium salts and phosphonium salts which inventively boost the activity of crop protection compositions comprising fatty acid biosynthesis inhibitors are defined by formula (III')

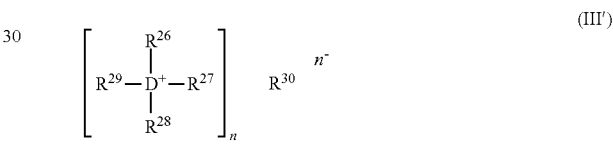

in which
D represents nitrogen or phosphorus,
D preferably represents nitrogen,
$R^{26}$, $R^{27}$, $R^{28}$ and $R^{29}$ independently of one another represent hydrogen or in each case optionally substituted $C_1$-$C_8$-alkyl or mono- or polyunsaturated, optionally substituted $C_1$-$C_8$-alkylene, the substituents being selectable from halogen, nitro and cyano,
$R^{26}$, $R^{27}$, $R^{28}$ and $R^{29}$ independently of one another preferably represent hydrogen or in each case optionally substituted $C_1$-$C_4$-alkyl, the substituents being selectable from halogen, nitro and cyano,
$R^{26}$, $R^{27}$, $R^{28}$ and $R^{29}$ independently of one another particularly preferably represent hydrogen, methyl, ethyl, n-propyl, isopropyl, n-butyl, isobutyl, sec-butyl or tert-butyl,
$R^{26}$, $R^{27}$, $R^{28}$ and $R^{29}$ very particularly preferably represent hydrogen,
n represents 1, 2, 3 or 4,
n preferably represents 1 or 2,
$R^{30}$ represents an organic or inorganic anion,
$R^{30}$ preferably represents hydrogencarbonate, tetraborate, fluoride, bromide, iodide, chloride, monohydrogenphosphate, dihydrogenphosphate, hydrogensulphate, tartrate, sulphate, nitrate, thiosulphate, thiocyanate, formate, lactate, acetate, propionate, butyrate, pentanoate or oxalate,
$R^{30}$ particularly preferably represents lactate, sulphate, nitrate, thiosulphate, thiocyanate, oxalate or formate.
$R^{30}$ very particularly preferably represents sulphate.
Inventively emphasized combinations of active compound, salt and penetrant are listed in the table below. "Penetrant as per test" means here that any compound that acts as a penetrant in the cuticle penetration test (Baur et al., 1997, *Pesticide Science* 51, 131-152) is suitable.

The ammonium salts and phosphonium salts of the formula (III') can be used in a broad concentration range to boost the activity of crop protection compositions comprising ketoenols. In general the ammonium salts or phosphonium salts are used in the ready-to-use crop protection composition in a concentration of 0.5 to 80 mmol/l, preferably 0.75 to 37.5 mmol/l, more preferably 1.5 to 25 mmol/l. In the case of a formulated product the ammonium salt and/or phosphonium salt concentration in the formulation is chosen such that it is within these stated general, preferred or particularly preferred ranges after the formulation has been diluted to the desired active-compound concentration. The concentration of the salt in the formulation is typically 1%-50% by weight.

In one preferred embodiment of the invention the activity is boosted by adding to the crop protection compositions not only an ammonium salt and/or phosphonium salt but also, additionally, a penetrant. It is considered entirely surprising that even in these cases an even greater boost to activity is observed. The present invention therefore likewise provides for the use of a combination of penetrant and ammonium salts and/or phosphonium salts to boost the activity of crop protection compositions which comprise insecticidal, oxaspirocyclic spiro-substituted tetramic and tetronic acid derivatives as active compound. The invention likewise provides compositions which comprise herbicidal and/or acaricidal and/or insecticidal oxaspirocyclic spiro-substituted tetramic and tetronic acid derivatives, penetrants and ammonium salts and/or phosphonium salts, including specifically not only formulated active compounds but also ready-to-use compositions (spray liquors). The invention additionally provides, finally, for the use of these compositions for controlling insect pests.

Suitable penetrants in the present context include all those substances which are typically used to enhance the penetration of active agrochemical compounds into plants. Penetrants are defined in this context by their ability to penetrate from the aqueous spray liquor and/or from the spray coating into the cuticle of the plant and thereby to increase the mobility of active compounds in the cuticle. The method described in the literature (Baur et al., 1997, *Pesticide Science* 51, 131-152) can be used in order to determine this property.

Examples of suitable penetrants include alkanol alkoxylates. Penetrants of the invention are alkanol alkoxylates of the formula (IV')

R—O-(-AO)$_v$—R'     (IV')

in which
R is linear or branched alkyl having 4 to 20 carbon atoms,
R' is hydrogen, methyl, ethyl, n-propyl, isopropyl, n-butyl, isobutyl, tert-butyl, n-pentyl or n-hexyl,
AO is an ethylene oxide radical, a propylene oxide radical, a butylene oxide radical or is mixtures of ethylene oxide and propylene oxide radicals or butylene oxide radicals, and
v is a number from 2 to 30.

One preferred group of penetrants are alkanol alkoxylates of the formula

R—O-(-EO—)$_n$—R'     (IV'-a)

in which
R is as defined above,
R' is as defined above,
EO is —CH$_2$—CH$_2$—O—, and
n is a number from 2 to 20.

A further preferred group of penetrants are alkanol alkoxylates of the formula

R—O-(-EO—)$_p$—(—PO—)$_q$—R'     (IV'-b)

in which
R is as defined above,
R' is as defined above,
EO is —CH$_2$—CH$_2$—O—,
PO is

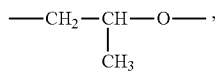

p is a number from 1 to 10, and
q is a number from 1 to 10.

A further preferred group of penetrants are alkanol alkoxylates of the formula

R—O—(—PO—)$_r$-(EO—)$_s$—R'     (IV'-c)

in which
R is as defined above,
R' is as defined above,
EO is —CH$_2$—CH$_2$—O—,
PO is

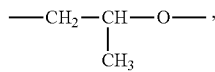

r is a number from 1 to 10, and
s is a number from 1 to 10.

A further preferred group of penetrants are alkanol alkoxylates of the formula

R—O-(-EO—)$_p$—(—BO—)$_q$—R'     (IV'-d)

in which
R and R' are as defined above,
EO is CH$_2$—CH$_2$—O—,
BO is

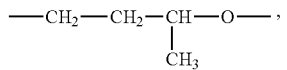

p is a number from 1 to 10 and
q is a number from 1 to 10.

A further preferred group of penetrants are alkanol alkoxylates of the formula

R—O—(—BO—)$_r$-(-EO—)$_s$—R'     (IV'-e)

in which
R and R' are as defined above,
BO is

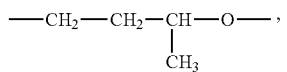

EO is CH$_2$—CH$_2$—O—,
r is a number from 1 to 10 and
s is a number from 1 to 10.

A further preferred group of penetrants are alkanol alkoxylates of the formula

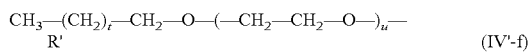 (IV'-f)

in which
R' is as defined above,
t is a number from 8 to 13,
u is a number from 6 to 17.
In the formulae indicated above,
R is preferably butyl, isobutyl, n-pentyl, isopentyl, neopentyl, n-hexyl, isohexyl, n-octyl, isooctyl, 2-ethylhexyl, nonyl, isononyl, decyl, n-dodecyl, isododecyl, lauryl, myristyl, isotridecyl, trimethylnonyl, palmityl, stearyl or eicosyl.

As an example of an alkanol alkoxylate of the formula (IV'-c) mention may be made of 2-ethylhexyl alkoxylate of the formula

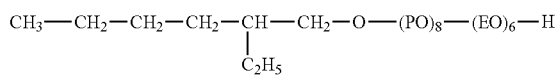 (IV'-c-1)

in which
EO is —CH$_2$—CH$_2$—O—,
PO is

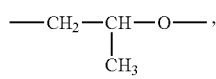

and
the numbers 8 and 6 represent average values.

As an example of an alkanol alkoxylate of the formula (IV'-d) mention may be made of the formula

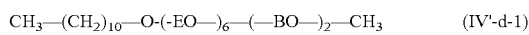 (IV'-d-1)

in which
EO is CH$_2$—CH$_2$—O—,
BO is

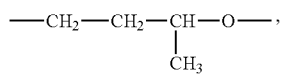

and
the numbers 10, 6 and 2 represent average values.

Particularly preferred alkanol alkoxylates of the formula (IV'-f) are compounds of this formula in which
t is a number from 9 to 12 and
u is a number from 7 to 9.

Mention may be made with very particular preference of alkanol alkoxylate of the formula (IV'-f-1)

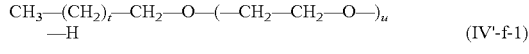 (IV'-f-1)

in which
t stands for the average value 10.5 and
u stands for the average value 8.4.

A general definition of the alkanol alkoxylates is given by the formulae above. These substances are mixtures of compounds of the stated type with different chain lengths. The indices therefore have average values which may also deviate from whole numbers.

The alkanol alkoxylates of the formulae stated are known and in some cases are available commercially or can be prepared by known methods (cf. WO 98/35 553, WO 00/35 278 and EP-A 0 681 865).

Suitable penetrants also include, for example, substances which promote the availability of the compounds of the formula (I) in the spray coating. These include, for example, mineral or vegetable oils. Suitable oils are all mineral or vegetable oils—modified or otherwise—which can typically be used in agrochemical compositions. Mention may be made by way of example of sunflower oil, rapeseed oil, olive oil, castor oil, colza oil, maize seed oil, cotton seed oil and soybean oil, or the esters of said oils. Preference is given to rapeseed oil, sunflower oil and their methyl or ethyl esters.

The concentration of penetrant in the compositions of the invention can be varied within a wide range. In the case of a formulated crop protection composition it is in general 1% to 95%, preferably 1% to 55%, more preferably 15%-40% by weight. In the ready-to-use compositions (spray liquors) the concentrations are generally between 0.1 and 10 g/l, preferably between 0.5 and 5 g/l.

Crop protection compositions of the invention may also comprise further components, examples being surfactants and/or dispersing assistants or emulsifiers.

Suitable nonionic surfactants and/or dispersing assistants include all substances of this type that can typically be used in agrochemical compositions. Preferably mention may be made of polyethylene oxide-polypropylene oxide block copolymers, polyethylene glycol ethers of linear alcohols, reaction products of fatty acids with ethylene oxide and/or propylene oxide, and also polyvinyl alcohol, polyvinylpyrrolidone, copolymers of polyvinyl alcohol and polyvinylpyrrolidone, and copolymers of (meth)acrylic acid and (meth)acrylic esters, and additionally alkyl ethoxylates and alkylaryl ethoxylates, which optionally may be phosphated and optionally may be neutralized with bases, mention being made, by way of example, of sorbitol ethoxylates, and, as well, polyoxyalkylenamine derivatives.

Suitable anionic surfactants include all substances of this type that can typically be used in agrochemical compositions. Preference is given to alkali metal salts and alkaline earth metal salts of alkylsulphonic acids or alkylarylsulphonic acids.

A further preferred group of anionic surfactants and/or dispersing assistants are the following salts that are of low solubility in plant oil: salts of polystyrenesulphonic acids, salts of polyvinylsulphonic acids, salts of naphthalenesulphonic acid-formaldehyde condensation products, salts of condensation products of naphthalenesulphonic acid, phenolsulphonic acid and formaldehyde, and salts of lignosulphonic acid.

Suitable additives which may be included in the formulations of the invention are emulsifiers, foam inhibitors, preservatives, antioxidants, colorants and inert filling materials.

Preferred emulsifiers are ethoxylated nonylphenols, reaction products of alkylphenols with ethylene oxide and/or propylene oxide, ethoxylated arylalkylphenols, and also ethoxylated and propoxylated arylalkylphenols, and also sulphated or phosphated arylalkyl ethoxylates and/or arylalkyl ethoxypropoxylates, mention being made by way of example of sorbitan derivatives, such as polyethylene oxide-sorbitan fatty acid esters, and sorbitan fatty acid esters.

Using, for example, according to process (A) ethyl N-[(4-chloro-2,6-dimethyl)phenylacetyl]-1-amino-4,4'-propylenyloxycyclohexanecarboxylate as starting material, the course of the process according to the invention can be represented by the reaction scheme below:

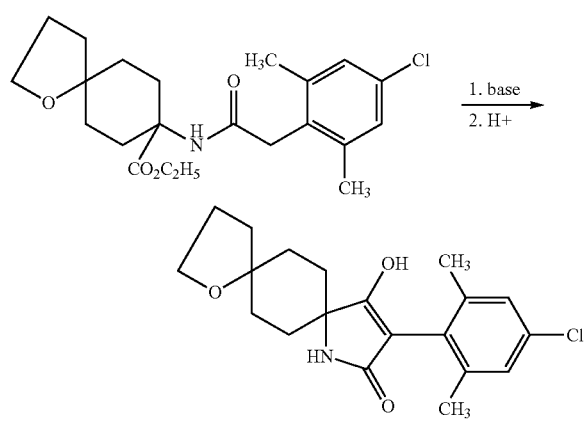

Using, for example, according to process (B) ethyl O-[(2-chloro-6-methyl)phenylacetyl]-1-hydroxy-4,4'-propyleny-loxycyclohexanecarboxylate, the course of the process according to the invention can be represented by the reaction scheme below:

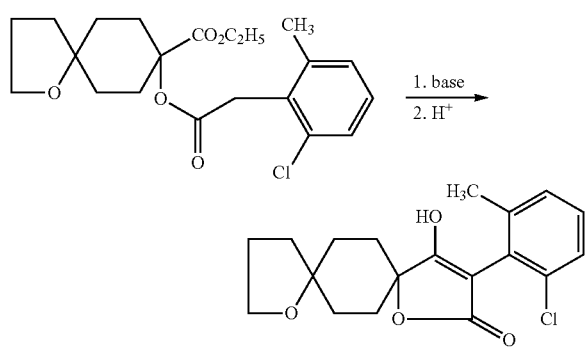

Using, for example, according to process (Cα) 8,8'-propylenoxy-3-[(4-chloro-2,6-dimethyl)-phenyl]-1-azaspiro[4,5]decane-2,4-dione and pivaloyl chloride as starting materials, the course of the process according to the invention can be represented by the reaction scheme below:

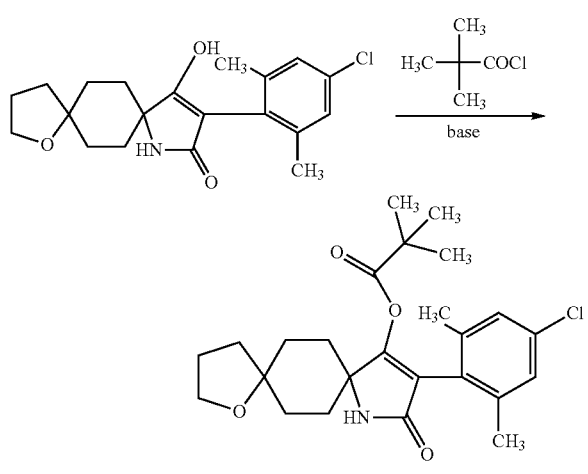

Using, for example, according to process (C) (variant β) 8,8'-propylenoxy-3-[(2,4-dichloro)-phenyl]-1-oxaspiro-[4,5]-decane-2,4-dione and acetic anhydride as starting materials, the course of the process according to the invention can be represented by the reaction scheme below:

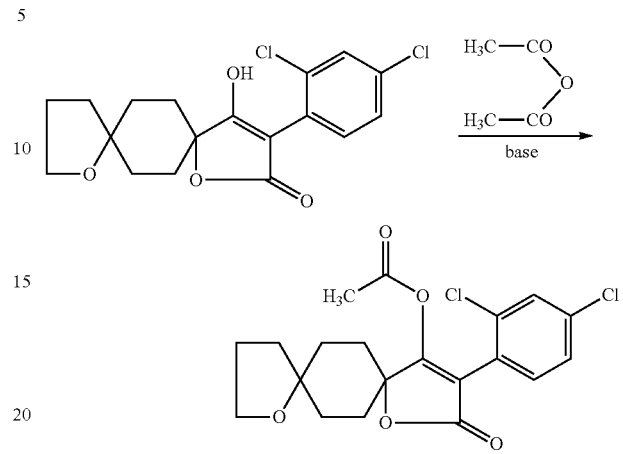

Using, for example, according to process (D) 8,8'-propylenoxy-3-[(2,4-dichloro-6-methyl)phenyl]-1-azaspiro[4,5]decane-2,4-dione and ethyl chloroformate as starting materials, the course of the process according to the invention can be represented by the reaction scheme below:

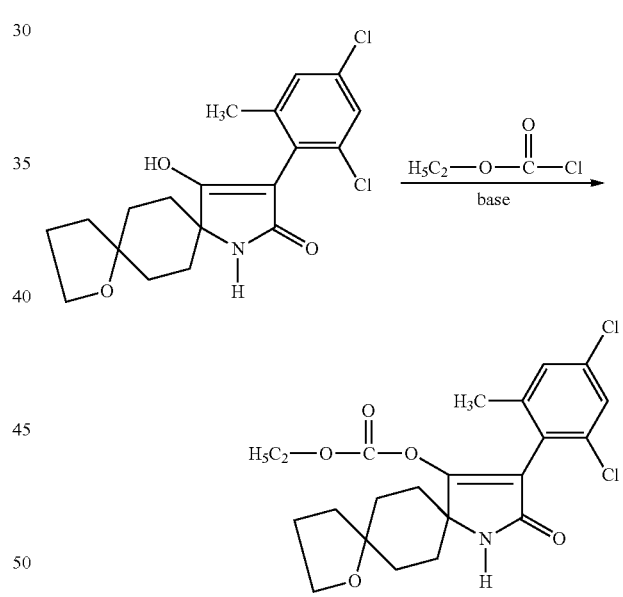

Using, for example, according to process (E) 8,8'-propylenoxy-3-[(2,4,6-trimethyl)phenyl]-1-oxa-spiro[4,5]decane-2,4-dione and methyl chloromonothioformate as starting materials, the course of the reaction can be represented as follows:

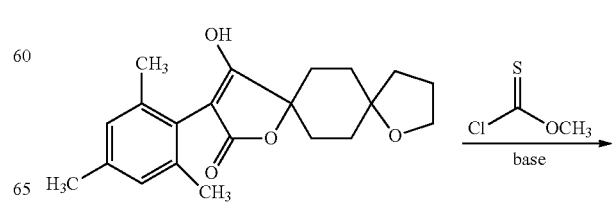

-continued

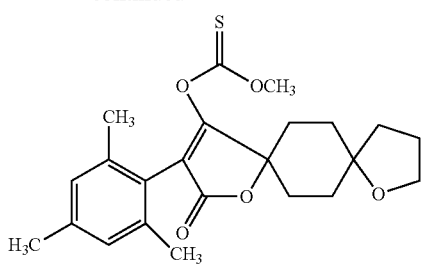

Using, for example, according to process (F) 8,8'-propylenoxy-3-[(2,4,6-trimethyl)phenyl]-1-azaspiro[4,5]decane-2,4-dione and methanesulphonyl chloride as starting materials, the course of the reaction can be represented by the reaction scheme below:

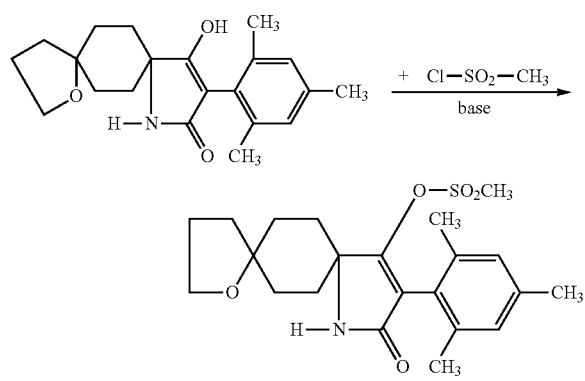

Using, for example, according to process (G) 8,8'-propylenoxy-3-[(2,4-dichloro-6-methyl)-phenyl]-1-oxaspiro[4,5]decane-2,4-dione and 2,2,2-trifluoroethyl methanethiophosphonyl chloride as starting materials, the course of the reaction can be represented by the reaction scheme below:

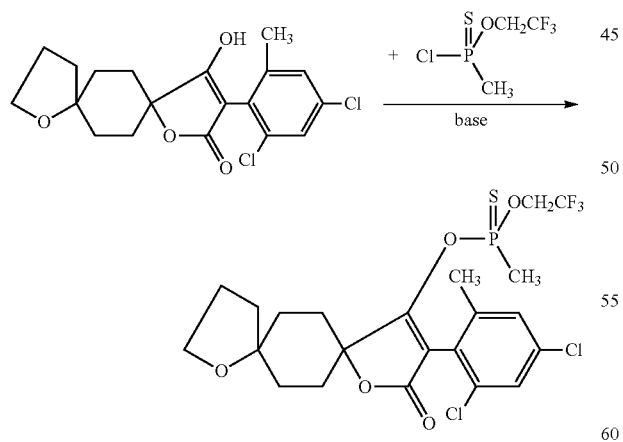

Using, for example, according to process (H) 8,8'-propylenoxy-3-[(2,3,4,6-tetramethylphenyl]-1-azaspiro[4,5]decane-2,4-dione and NaOH as components, the course of the process according to the invention can be represented by the reaction scheme below:

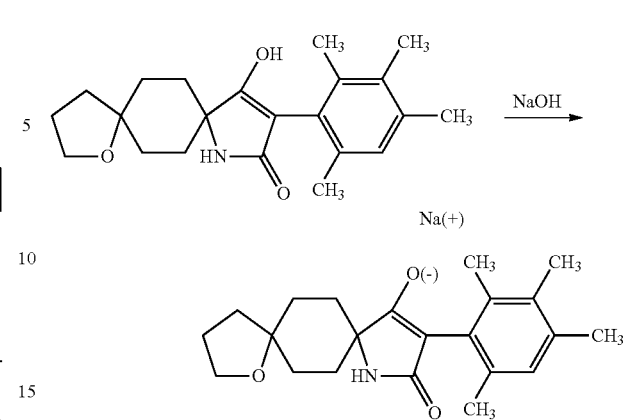

Using, for example, according to process (I) (variant α) 8,8'-propylenoxy-3-[(2,4,5-trimethyl)-phenyl]-1-oxaspiro[4,5]decane-2,4-dione and ethyl isocyanate as starting materials, the course of the reaction can be represented by the reaction scheme below:

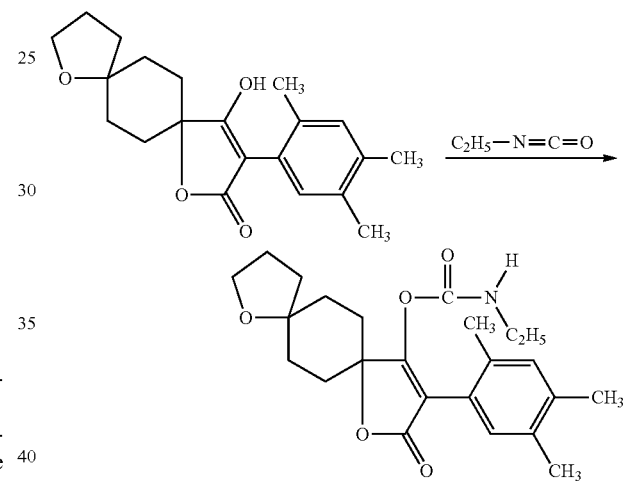

Using, for example, according to process (I) (variant β) 8,8'-propylenoxy-3-[(2-4,6-trimethyl)-phenyl]-1-azaspiro[4,5]decane-2,4-dione and dimethylcarbamoyl chloride as starting materials, the course of the reaction can be represented by the scheme below:

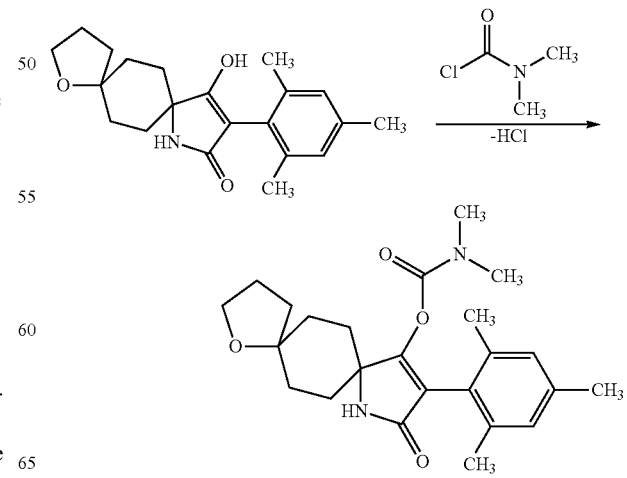

Using, for example, according to process (Jβ) 8,8'-propylenoxy-3-[(4-bromo-2,6-dimethyl-phenyl)]-1-azaspiro[4,5]decane-2,4-dione and 4-chlorophenylboronic acid as starting materials, the course of the reaction can be represented by the scheme below:

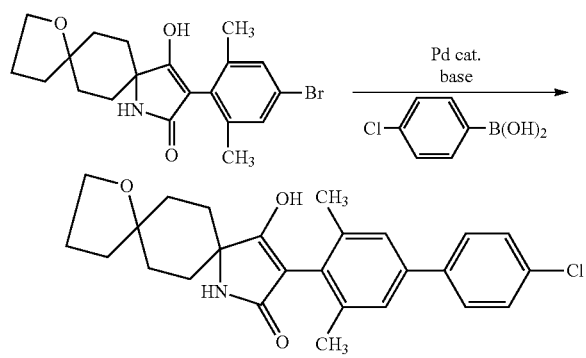

The compounds, required as starting materials in the process (A) according to the invention, of the formula (II)

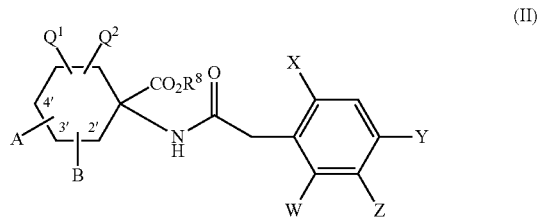

(II)

in which

A, B, $Q^1$, $Q^2$, W, X, Y, Z and $R^8$ have the meanings given above are novel.

The acylamino acid esters of the formula (II) are obtained, for example, when amino acid derivatives of the formula (XVI)

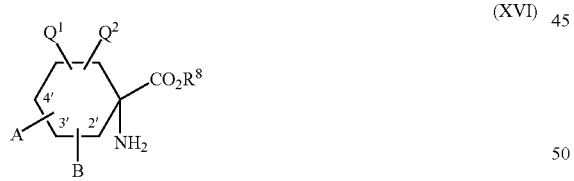

(XVI)

in which

A, B, $Q^1$ and $Q^2$ and $R^8$ have the meaning given above are acylated with substituted phenylacetic acid derivatives of the formula (XVII)

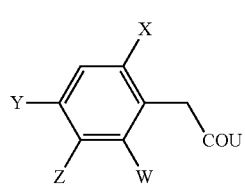

(XVII)

in which

W, X, Y and Z have the meanings given above and

U represents a leaving group introduced by reagents for activating carboxylic acids, such as carbonyldiimidazole, carbodiimides (such as, for example, dicyclohexylcarbodiimide), phosphorylating agents (such as, for example, $POCl_3$, BOP-Cl), halogenating agents, such as, for example, thionyl chloride, oxalyl chloride, phosgene or chloroformic esters (Chem. Reviews 52, 237-416 (1953); Bhattacharya, Indian J. Chem. 6, 341-5, 1968)

or when acylamino acids of the formula (XVIII)

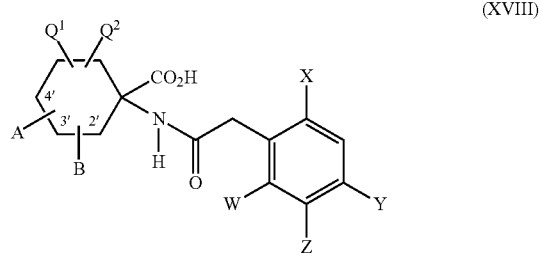

(XVIII)

in which

A, B, $Q^1$, $Q^2$, W, X, Y and Z have the meanings given above are esterified (Chem. Ind. (London) 1568 (1968)).

The compounds of the formula (XVIII)

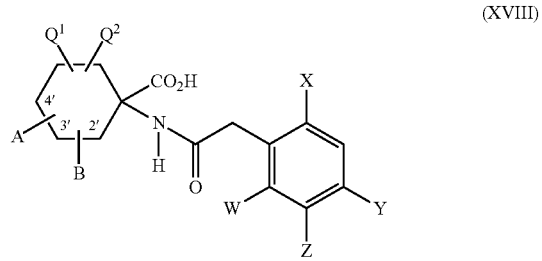

(XVIII)

in which

A, B, $Q^1$, $Q^2$, W, X, Y and Z have the meanings given above, are novel.

The compounds of the formula (XVIII) are obtained, for example, when 1-aminocyclohexane-carboxylic acids of the formula (XIX)

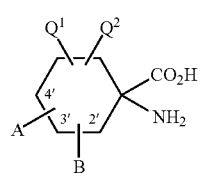

(XIX)

in which

A, B, $Q^1$ and $Q^2$ have the meanings given above are acylated with substituted phenylacetic acid derivatives of the formula (XVII)

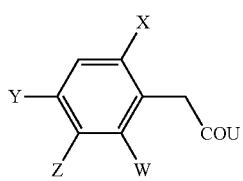
(XVII)

in which

U, W, X, Y and Z have the meanings given above, for example according to Schotten-Baumann (Organikum, VEB Deutscher Verlag der Wissen-schaften, Berlin 1977, p. 505).

Some of the compounds of the formula (XVII) are known, and/or they can be prepared by the known processes in the laid-open publications cited at the outset.

The compounds of the formulae (XVI) and (XIX) are novel and can be prepared by known processes (see, for example, Compagnon, Ann. Chim. (Paris) [14] 5, pp. 11-22, 23-27 (1970), L. Munday, J. Chem. Soc. 4372 (1961); J. T. Eward, C. Jitrangeri, Can. J. Chem. 53, 3339 (1975)).

The novel 1-amino-cyclohexanecarboxylic acids (XIX) can generally be obtained by the Bucherer Bergs synthesis or by the Strecker synthesis, where they are obtained in different isomeric forms. For the sake of simplicity, hereinbelow the isomers in which the oxygen atom in the 4-position and the amino group are positioned equatorial/axial or axial/equatorial are referred to as β. For the sake of simplicity, hereinbelow the isomers in which the amino group and the oxygen atom in the 4-position are equatorial/equatorial or axial/axial are referred to as α.

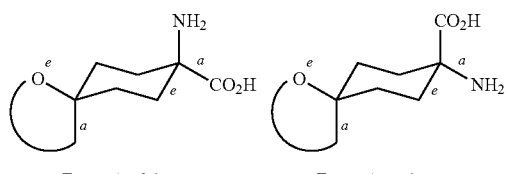

Example: β isomer      Example: α isomer (L. Munday, J. Chem. Soc. 4372 (1961)).

The compounds of the formula (XIX) can be obtained from compounds of the formula (XXIII)

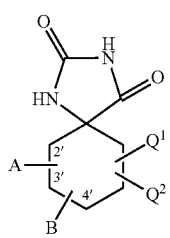
(XXIII)

in which A, B, $Q^1$ and $Q^2$ have the meanings given above.

The compounds of the formula (XXIII) are novel and can be prepared by methods known from the literature (for example Bucherer-Bergs reaction, see also the Examples).

Furthermore, the starting materials, used in the above process (A) of the formula (II)

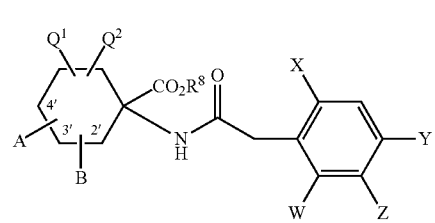
(II)

in which

A, B, $Q^1$, $Q^2$, W, X, Y, Z and $R^8$ have the meanings given above can be prepared by reacting 1-aminocyclohexanecarbonitriles of the formula (XX)

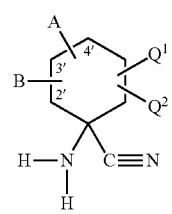
(XX)

in which

A, B, $Q^1$ and $Q^2$ have the meanings given above, with substituted phenylacetic acid derivatives of the formula (XVII)

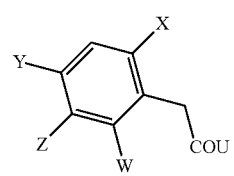
(XVII)

in which

U, W, X, Y and Z have the meanings given above to give compounds of the formula (XXI)

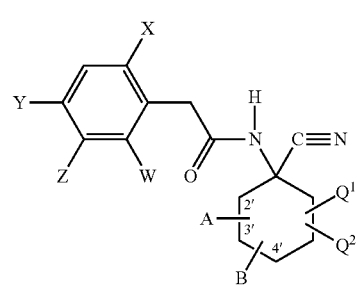
(XXI)

in which

A, B, $Q^1$, $Q^2$, W, X, Y and Z have the meanings given above, and then subjecting these to an acidic alcoholysis.

The compounds of the formula (XXI) are likewise novel. Some of the compounds of the formula (XX) are novel, and they can be prepared as described, for example, in EP-A-595 130.

The compounds, required as starting materials in the process (B) according to the invention of the formula (III)

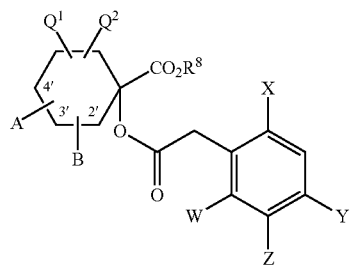
(III)

in which
A, B, $Q^1$, $Q^2$, W, X, Y, Z and $R^8$ have the meanings given above
are novel.

They can be prepared in a simple manner by methods known in principle.

The compounds of the formula (III) are obtained, for example, when
1-hydroxycyclohexanecarboxylic esters of the formula (XXII)

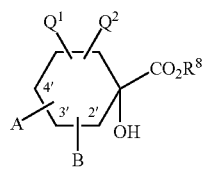
(XXII)

in which
A, B, $Q^1$, $Q^2$ and $R^8$ have the meanings given above
are acylated with substituted phenylacetic acid derivatives of the formula (XVII)

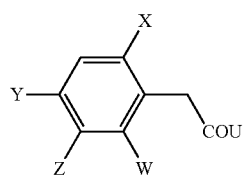
(XVII)

in which
U, W, X, Y and Z have the meanings given above
(Chem. Reviews 52, 237-416 (1953)).

The 1-hydroxy-3-alkoxycyclohexylcarboxylic esters of the formula (XXII) are novel. They are obtained, for example, when substituted 1-hydroxy-4,4'-alkylidenyloxycyclohexanecarbonitriles are reacted in the presence of acids, for example according to Pinner with alcohols. The cyanohydrin is obtained, for example, by reaction of substituted 4,4'-alkylidenyloxycyclohexan-1-ones with hydrocyanic acid (see WO 99/16748).

The acid halides of the formula (IV), carboxylic anhydrides of the formula (V), chloroformic esters or chloroformic thioesters of the formula (VI), chloromonothioformic esters or chlorodithioformic esters of the formula (VII), sulphonyl chlorides of the formula (VIII), phosphorus compounds of the formula (IX) and metal hydroxides, metal alkoxides or amines of the formulae (X) and (XI) and isocyanates of the formula (XII) and carbamoyl chlorides of the formula (XIII) and boronic acids of the formula (XV) furthermore required as starting materials for carrying out the processes (C), (D), (E), (F), (G), (H), (I) and (J) according to the invention are generally known compounds of organic or inorganic chemistry.

In addition, the compounds of the formulae (XVII), (I-1-a') to (I-2-g') and (I-1-a'') to (I-2-g'') are furthermore known from the patent applications cited at the outset, and/or they can be prepared by the methods given in these publications.

The process (A) is characterized in that compounds of the formula (II) in which A, B, $Q^1$, $Q^2$, W, X, Y, Z and $R^8$ are as defined above are subjected to an intramolecular condensation in the presence of a diluent and in the presence of a base.

Suitable for use as diluents in the process (A) according to the invention are all organic solvents which are inert toward the reactants. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulphoxide, sulpholane, dimethylformamide and N-methylpyrrolidone, and also alcohols, such as methanol, ethanol, propanol, isopropanol, butanol, isobutanol and tert-butanol.

Suitable bases (deprotonating agents) for carrying out the process (A) according to the invention are all customary proton acceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be used in the presence of phase-transfer catalysts, such as, for example, triethylbenzylammonium chloride, tetrabutylammonium bromide, Adogen 464 (=methyl-trialkyl($C_8$-$C_{10}$)ammonium chloride) or TDA 1 (=tris(methoxyethoxyethyl)amine). It is furthermore possible to use alkali metals, such as sodium or potassium. It is also possible to employ alkali metal and alkaline earth metal amides and hydrides, such as sodium amide, sodium hydride and calcium hydride, and additionally also alkali metal alkoxides, such as sodium methoxide, sodium ethoxide and potassium tert-butoxide.

When carrying out the process (A) according to the invention, the reaction temperatures can be varied within a relatively wide range. In general, the process is carried out at temperatures between 75° C. and 200° C., preferably between −50° C. and 150° C. The process (A) according to the invention is generally carried out under atmospheric pressure.

When carrying out the process (A) according to the invention, the reaction components of the formula (II) and the deprotonating bases are generally employed in approximately doubly equimolar amounts. However, it is also possible to use a relatively large excess (up to 3 mol) of one or the other component.

The process (B) is characterized in that compounds of the formula (III), in which A, B, $Q^1$, $Q^2$, W, X, Y, Z and $R^8$ are as defined above are subjected to an intramolecular condensation in the presence of a diluent and in the presence of a base.

Suitable for use as diluents in the process (B) according to the invention are all organic solvents which are inert toward the reactants. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulphoxide, sulpholane, dimethylformamide and N-methylpyrrolidone. Alcohols, such as methanol, ethanol, propanol, isopropanol, butanol, isobutanol and tert-butanol can also be used.

Suitable bases (deprotonating agents) for carrying out the process (B) according to the invention are all customary proton acceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be used in the presence of phase-transfer catalysts, such as, for example, triethylbenzylammonium chloride, tetrabutylammonium bromide, Adogen 464 (=methyltrialkyl($C_8$-$C_{10}$)ammonium chloride) or TDA 1 (=tris(methoxyethoxyethyl)amine). It is furthermore possible to use alkali metals, such as sodium or potassium. It is also possible to employ alkali metal and alkaline earth metal amides and hydrides, such as sodium amide, sodium hydride and calcium hydride, and additionally also alkali metal alkoxides, such as sodium methoxide, sodium ethoxide and potassium tert-butoxide.

When carrying out the process (B) according to the invention, the reaction temperature can be varied within a relatively wide range. In general, the process is carried out at temperatures between 75° C. and 200° C., preferably between −50° C. and 150° C.

The process (B) according to the invention is generally carried out under atmospheric pressure.

When carrying out the process (B) according to the invention, the reaction components of the formula (II) and the deprotonating bases are generally employed in approximately equimolar amounts. However, it is also possible to use a relatively large excess (up to 3 mol) of one or the other component.

The process ($C_\alpha$) is characterized in that compounds of the formulae (I-1-a) to (I-2-a) are in each case reacted with carbonyl halides of the formula (IV), if appropriate in the presence of a diluent and if appropriate in the presence of an acid binder.

Suitable diluents for use in the process ($C_\alpha$) according to the invention are all solvents which are inert toward the acid halides. Preference is given to using hydrocarbons, such as benzine, benzene, toluene, xylene and tetralin, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, and also strongly polar solvents, such as dimethyl formamide, dimethyl sulphoxide and sulpholane. The hydrolytic stability of the acid halide permitting, the reaction can also be carried out in the presence of water.

Suitable acid binders for the reaction according to the process ($C_\alpha$) according to the invention are all customary acid acceptors. Preference is given to using tertiary amines, such as triethylamine, pyridine, diazabicyclooctane (DABCO), diazabicycloundecene (DBU), diazabicyclononene (DBN), Hünig base and N,N-dimethylaniline, furthermore alkaline earth metal oxides, such as magnesium oxide and calcium oxide, moreover alkali metal and alkaline earth metal carbonates, such as sodium carbonate, potassium carbonate and calcium carbonate, and also alkali metal hydroxides, such as sodium hydroxide and potassium hydroxide.

The reaction temperatures in the process ($C_\alpha$) according to the invention may be varied within a relatively wide range. In general, the process is carried out at temperatures between −20° C. and +150° C., preferably between 0° C. and 100° C.

When carrying out the process ($C_\alpha$) according to the invention, the starting materials of the formulae (I-1-a) to (I-2-a) and the carbonyl halide of the formula (IV) are generally each employed in approximately equivalent amounts. However, it is also possible to use a relatively large excess (up to 5 mol) of the carbonyl halide. Work-up is carried out by customary methods.

The process ($C_\beta$) is characterized in that compounds of the formulae (I-1-a) to (I-2-a) are in each case reacted with carboxylic anhydrides of the formula (V), if appropriate in the presence of a diluent and if appropriate in the presence of an acid binder.

Suitable for use as diluents in the process ($C_\beta$) according to the invention are, preferably, those diluents which are also preferred when acid halides are used. Besides, it is also possible for excess carboxylic anhydride to act simultaneously as diluent.

Suitable acid binders for process ($C_\beta$), which are added, if appropriate, are preferably those acid binders which are also preferred when acid halides are used.

The reaction temperature in the process ($C_\beta$) according to the invention can be varied within a relatively wide range. In general, the process is carried out at temperatures between −20° C. and +150° C., preferably between 0° C. and 100° C.

When carrying out the process ($C_\beta$) according to the invention, the starting materials of the formulae (I-1-a) to (I-2-a) and the carboxylic anhydride of the formula (V) are generally each employed in approximately equivalent amounts. However, it is also possible to use a relatively large excess (up to 5 mol) of the carboxylic anhydride. Work-up is carried out by customary methods.

In general, diluent and excess carboxylic anhydride and the carboxylic acid formed are removed by distillation or by washing with an organic solvent or with water.

The process (D) is characterized in that compounds of the formulae (I-1-a) to (I-2-a) are in each case reacted with chloroformic esters or chloroformic thioesters of the formula (VI), if appropriate in the presence of a diluent and if appropriate in the presence of an acid binder.

Suitable acid binders for the reaction according to process (D) according to the invention are all customary acid acceptors. Preference is given to using tertiary amines, such as triethylamine, pyridine, DABCO, DBU, DBA, Hünig base and N,N-dimethylaniline, furthermore alkaline earth metal oxides, such as magnesium oxide and calcium oxide, moreover alkali metal and alkaline earth metal carbonates, such as sodium carbonate, potassium carbonate and calcium carbonate, and also alkali metal hydroxides, such as sodium hydroxide and potassium hydroxide.

Suitable diluents for use in the process (D) according to the invention are all solvents which are inert toward the chloroformic esters or chloroformic thioesters. Preference is given to using hydrocarbons, such as benzine, benzene, toluene, xylene and tetralin, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, moreover nitriles such as acetonitrile and also strongly polar solvents, such as dimethyl formamide, dimethyl sulphoxide and sulpholane.

When carrying out the process (D) according to the invention, the reaction temperature can be varied within a relatively wide range. Reaction temperatures are generally between −20° C. and +100° C., preferably between 0° C. and 50° C.

The process (D) according to the invention is generally carried out under atmospheric pressure.

When carrying out the process (D) according to the invention, the starting materials of the formulae (I-1-a) to (I-2-a) and the appropriate chloroformic ester or chloroformic thioester of the formula (VI) are generally each employed in approximately equivalent amounts. However, it is also possible to use a relatively large excess (up to 2 mol) of one component or the other. Work-up is carried out by customary methods. In general, precipitated salts are removed and the reaction mixture that remains is concentrated by removing the diluent under reduced pressure.

The process (E) according to the invention is characterized in that compounds of the formulae (I-1-a) to (I-2-a) are in each case reacted with compounds of the formula (VII) in the presence of a diluent and, if appropriate, in the presence of an acid binder.

In preparation process (E), about 1 mol of chloromonothioformic ester or chlorodithioformic ester of the formula (VII) is reacted per mole of the starting material of the formulae (I-1-a) to (I-2-a) at from 0 to 120° C., preferably from 20 to 60° C.

Suitable diluents, which are added, if appropriate, are all inert polar organic solvents, such as ethers, amides, sulphones, sulphoxides, and also halogenated alkanes.

Preference is given to using dimethyl sulphoxide, tetrahydrofuran, dimethylformamide, ethyl acetate or methylene chloride.

If, in a preferred embodiment, the enolate salt of the compounds (I-1-a) to (I-2-a) is prepared by addition of strong deprotonating agents, such as, for example, sodium hydride or potassium tert-butoxide, the further addition of acid binders may be dispensed with.

Bases suitable for use in the process (E) are all customary proton acceptors. Preference is given to using alkali metal hydrides, alkali metal alkoxides, alkali metal or alkaline earth metal carbonates or bicarbonates or nitrogen bases. Mention may be made, for example, of sodium hydride, sodium methoxide, sodium ethoxide, calcium hydroxide, potassium carbonate, sodium bicarbonate, triethylamine, dibenzylamine, diisopropylamine, pyridine, quinoline, diazabicyclooctane (DABCO), diazabicyclononene (DBN) and diazabicycloundecene (DBU).

The reaction can be carried out at atmospheric pressure or under elevated pressure and is preferably carried out at atmospheric pressure. Work-up is carried out by customary methods.

The process (F) according to the invention is characterized in that compounds of the formulae (I-1-a) to (I-2-a) are in each case reacted with sulphonyl chlorides of the formula (VIII), if appropriate in the presence of a diluent and if appropriate in the presence of an acid binder.

In preparation process (F), about 1 mol of sulphonyl chloride of the formula (VIII) is reacted per mole of starting material of the formula (I-1-a to I-2-a), at from −20 to 150° C., preferably from 0 to 70° C.

The process (F) is preferably carried out in the presence of a diluent.

Suitable diluents are all inert polar organic solvents, such as ethers, amides, ketones, carboxylic esters, nitriles, sulphones, sulphoxides or halogenated hydrocarbons, such as methylene chloride.

Preference is given to using dimethyl sulphoxide, tetrahydrofuran, dimethylformamide, ethyl acetate, methylene chloride.

If, in a preferred embodiment, the enolate salt of the compounds (I-1-a) to (I-2-a) is prepared by addition of strong deprotonating agents (such as, for example, sodium hydride or potassium tert-butoxide), the further addition of acid binders may be dispensed with.

If acid binders are used, customary inorganic or organic bases are suitable, by way of example sodium hydroxide, sodium carbonate, potassium carbonate, pyridine, triethylamine.

The reaction can be carried out at atmospheric pressure or under elevated pressure and is preferably carried out at atmospheric pressure. Work-up is carried out by customary methods.

The process (G) according to the invention is characterized in that compounds of the formulae (I-1-a) to (I-2-a) are in each case reacted with phosphorus compounds of the formula (IX), if appropriate in the presence of a diluent and if appropriate in the presence of an acid binder.

In preparation process (G), to obtain compounds of the formulae (I-1-e) to (I-2-e) 1 to 2, preferably 1 to 1.3, mol of the phosphorus compound of the formula (XX) are employed per mole of the compounds (I-1-a) to (I-2-a), at temperatures between −40° C. and 150° C., preferably between −10 and 110° C.

The process (G) is preferably carried out in the presence of a diluent.

Suitable diluents are all inert polar organic solvents, such as ethers, carboxylic esters, halogenated hydrocarbons, ketones, amides, nitriles, sulphones, sulphoxides, etc.

Preference is given to using acetonitrile, dimethyl sulphoxide, tetrahydrofuran, dimethylformamide, methylene chloride.

Suitable acid binders, which are added, if appropriate, are customary inorganic or organic bases, such as hydroxides, carbonates or amines. Sodium hydroxide, sodium carbonate, potassium carbonate, pyridine, triethylamine may be mentioned by way of example.

The reaction can be carried out at atmospheric pressure or under elevated pressure and is preferably carried out at atmospheric pressure. Work-up is carried out by customary methods of organic chemistry. The end products obtained are preferably purified by crystallization, chromatographic purification or by so-called "incipient distillation", i.e. removal of the volatile components under reduced pressure.

The process (H) is characterized in that compounds of the formulae (I-1-a) to (I-2-a) are reacted in each case with metal hydroxides or metal alkoxides of the formula (X) or amines of the formula (XI), if appropriate in the presence of a diluent.

Suitable for use as diluents in the process (H) according to the invention are, preferably, ethers, such as tetrahydrofuran, dioxane, diethyl ether, or else alcohols, such as methanol, ethanol, isopropanol, but also water. The process (H) according to the invention is generally carried out under atmospheric pressure. The reaction temperatures are generally between −20° C. and 100° C., preferably between 0° C. and 50° C.

The process (I) according to the invention is characterized in that compounds of the formulae (I-1-a) to (I-2-a) are in each case reacted with (I-α) compounds of the formula (XII), if appropriate in the presence of a diluent and if appropriate in the presence of a catalyst, or (I-α) with compounds of the formula (XIII), if appropriate in the presence of a diluent and if appropriate in the presence of an acid binder.

In preparation process (I-α), about 1 mol of isocyanate of the formula (XII) is employed per mole of starting material of the formulae (I-1-a) to (I-2-a), at from 0 to 100° C., preferably from 20 to 50° C.

The process (I-α) is preferably carried out in the presence of a diluent.

Suitable diluents are all inert organic solvents, such as aromatic hydrocarbons, halogenated hydrocarbons, ethers, amides, nitriles, sulphones or sulphoxides.

If appropriate, catalysts may be added to accelerate the reaction. Suitable for use as catalysts are, very advantageously, organotin compounds, such as, for example, dibutyltin dilaurate.

The reaction is preferably carried out at atmospheric pressure.

In preparation process (I-β), about 1 mol of carbamoyl chloride of the formula (XIII) is employed per mole of starting material of the formulae (I-1-a) to (I-2-a) at from 0 to 150° C., preferably from 20 to 70° C.

Suitable diluents, which are added, if appropriate, are all inert polar organic solvents, such as ethers, carboxylic esters, nitriles, ketones, amides, sulphones, sulphoxides or halogenated hydrocarbons.

Preference is given to using dimethyl sulphoxide, tetrahydrofuran, dimethylformamide or methylene chloride.

If, in a preferred embodiment, the enolate salt of the compound (I-1-a) to (I-2-a) is prepared by addition of strong deprotonating agents (such as, for example, sodium hydride or potassium tert-butoxide), the further addition of acid binders may be dispensed with.

If acid binders are used, customary inorganic or organic bases are suitable, by way of example sodium hydroxide, sodium carbonate, potassium carbonate, triethylamine or pyridine.

The reaction may be carried out at atmospheric pressure or under elevated pressure and is preferably carried out at atmospheric pressure. Work-up is carried out by customary methods.

Suitable catalysts for carrying out the process (Jα) and (Jβ) according to the invention are palladium(0) complexes. Preference is given, for example, to tetrakis(triphenylphosphine) palladium. If appropriatiate, it is also possible to use palladium(II) compounds, for example $PdCl_2$, $Pd(OAC)_2$. If palladium(II) compounds are used, phosphines, such as, for example, tricyclohexylphosphine, are generally employed as complex formers.

Suitable acid acceptors for carrying out the processes (Jα) and (Jβ) according to the invention are inorganic or organic bases. These preferably include alkaline earth metal or alkali metal hydroxides, acetates, carbonates or bicarbonates, such as, for example, sodium hydroxide, potassium hydroxide, barium hydroxide or ammonium hydroxide, sodium acetate, potassium acetate, calcium acetate or ammonium acetate, sodium carbonate, potassium carbonate, caesium carbonate or ammonium carbonate, sodium bicarbonate or potassium bicarbonate, alkali metal fluorides, such as, for example, caesium fluoride, alkali metal phosphates, such as, for example, potassium dihydrogen phosphate, potassium phosphate and also tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

Suitable diluents for carrying out the processes (Jα) and (Jβ) according to the invention are water, organic solvents and any mixtures thereof. The following may be mentioned by way of example: aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, methylene chloride, chloroform, carbon tetrachloride, dichloroethane, trichloroethane or tetrachloroethylene; ethers, such as diethyl ether, diisoproypl ether, methyl t-butyl ether, methyl t-amyl ether, dioxane, tetrahydrofuran, 1,2-dimethoxyethane, 1,2-diethoxyethane, diethylene glycol dimethyl ether or anisole; alcohols, such as methanol, ethanol, n- or isopropanol, n-, iso-, sec- or tert-butanol, ethanediol, propane-1,2-diol, ethoxyethanol, methoxyethanol, diethylene glycol monomethyl ether, diethylene glycol monomethyl ether; water.

In the processes (Jα) and (Jβ) according to the invention, the reaction temperature can be varied within a relatively wide range. In general, the process is carried out at temperatures between 0° C. and +140° C., preferably between 50° C. and +100° C.

When carrying out the processes (Jα) and (Jβ) according to the invention, the boronic acids of the formulae (XVα) and (XVβ) in which Y and Z have the meaning given above and the compounds of the formulae (I-1-a') to (I-2-g') in which A, B, D, G, $Q^1$, $Q^2$, W, X, Y, and Z' have the meanings given above or the compounds of the formulae (I-1-a") to (I-2-g") in which A, B, D, G, $Q^1$, $Q^2$, W, X, Z and Y' have the meaning given above are employed in a molar ratio of from 1:1 to 3:1, preferably from 1:1 to 2:1. In general, from 0.005 to 0.5 mol, preferably from 0.01 mol to 0.1 mol, of catalyst are employed per mole of the compounds of the formulae (I-1-a') to (I-2-g') or (I-1-a") to (I-2-g"). The base is generally employed in excess. Work-up is carried out by customary methods.

The active compounds of the invention, in combination with good plant tolerance and favourable toxicity to warm-blooded animals and being tolerated well by the environment, are suitable for protecting plants and plant organs, for increasing the harvest yields, for improving the quality of the harvested material and for controlling animal pests, in particular insects, arachnids, helminths, nematodes and molluscs, which are encountered in agriculture, in horticulture, in animal husbandry, in forests, in gardens and leisure facilities, in the protection of stored products and of materials, and in the hygiene sector. They may be preferably employed as plant protection agents. They are active against normally sensitive and resistant species and against all or some stages of development. The abovementioned pests include:

From the order of the Anoplura (Phthiraptera), for example, *Damalinia* spp., *Haematopinus* spp., *Linognathus* spp., *Pediculus* spp., *Trichodectes* spp.

From the class of the Arachnida, for example, *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici*.

From the class of the Bivalva, for example, *Dreissena* spp.

From the order of the Chilopoda, for example, *Geophilus* spp., *Scutigera* spp.

From the order of the Coleoptera, for example, *Acanthoscelides obtectus, Adoretus* spp., *Agelastica alni, Agriotes* spp., *Amphimallon solstitialis, Anobium punctatum, Anoplophora* spp., *Anthonomus* spp., *Anthrenus* spp., *Apogonia* spp.,

*Atomaria* spp., *Attagenus* spp., *Bruchidius obtectus*, *Bruchus* spp., *Ceuthorhynchus* spp., *Cleonus mendicus*, *Conoderus* spp., *Cosmopolites* spp., *Costelytra zealandica*, *Curculio* spp., *Cryptorhynchus lapathi*, *Dermestes* spp., *Diabrotica* spp., *Epilachna* spp., *Faustinus cubae*, *Gibbium psylloides*, *Heteronychus arator*, *Hylamorpha elegans*, *Hylotrupes bajulus*, *Hypera postica*, *Hypothenemus* spp., *Lachnosterna consanguinea*, *Leptinotarsa decemlineata*, *Lissorhoptrus oryzophilus*, *Lixus* spp., *Lyctus* spp., *Meligethes aeneus*, *Melolontha melolontha*, *Migdolus* spp., *Monochamus* spp., *Naupactus xanthographus*, *Niptus hololeucus*, *Oryctes rhinoceros*, *Oryzaephilus surinamensis*, *Otiorrhynchus sulcatus*, *Oxycetonia jucunda*, *Phaedon cochleariae*, *Phyllophaga* spp., *Popillia japonica*, *Premnotrypes* spp., *Psylliodes chrysocephala*, *Ptinus* spp., *Rhizobius ventralis*, *Rhizopertha dominica*, *Sitophilus* spp., *Sphenophorus* spp., *Sternechus* spp., *Symphyletes* spp., *Tenebrio molitor*, *Tribolium* spp., *Trogoderma* spp., *Tychius* spp., *Xylotrechus* spp., *Zabrus* spp.

From the order of the Collembola, for example, *Onychiurus armatus*.

From the order of the Dermaptera, for example, *Forficula auricularia*.

From the order of the Diplopoda, for example, *Blaniulus guttulatus*.

From the order of the Diptera, for example, *Aedes* spp., *Anopheles* spp., *Bibio hortulanus*, *Calliphora erythrocephala*, *Ceratitis capitata*, *Chrysomyia* spp., *Cochliomyia* spp., *Cordylobia anthropophaga*, *Culex* spp., *Cuterebra* spp., *Dacus oleae*, *Dermatobia hominis*, *Drosophila* spp., *Fannia* spp., *Gastrophilus* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit*, *Pegomyia hyoscyami*, *Phorbia* spp., *Stomoxys* spp., *Tabanus* spp., *Tannia* spp., *Tipula paludosa*, *Wohlfahrtia* spp.

From the class of the Gastropoda, for example, *Arion* spp., *Biomphalaria* spp., *Bulinus* spp., *Deroceras* spp., *Galba* spp., *Lymnaea* spp., *Oncomelania* spp., *Succinea* spp.

From the class of the helminths, for example, *Ancylostoma duodenale*, *Ancylostoma ceylanicum*, *Acylostoma braziliensis*, *Ancylostoma* spp., *Ascaris lubricoides*, *Ascaris* spp., *Brugia malayi*, *Brugia timori*, *Bunostomum* spp., *Chabertia* spp., *Clonorchis* spp., *Cooperia* spp., *Dicrocoelium* spp., *Dictyocaulus filaria*, *Diphyllobothrium latum*, *Dracunculus medinensis*, *Echinococcus granulosus*, *Echinococcus multilocularis*, *Enterobius vermicularis*, *Faciola* spp., *Haemonchus* spp., *Heterakis* spp., *Hymenolepis nana*, *Hyostrongulus* spp., *Loa Loa*, *Nematodirus* spp., *Oesophagostomum* spp., *Opisthorchis* spp., *Onchocerca volvulus*, *Ostertagia* spp., *Paragonimus* spp., *Schistosomen* spp., *Strongyloides fuelleborni*, *Strongyloides stercoralis*, *Stronyloides* spp., *Taenia saginata*, *Taenia solium*, *Trichinella spiralis*, *Trichinella nativa*, *Trichinella britovi*, *Trichinella nelsoni*, *Trichinella pseudopsiralis*, *Trichostrongulus* spp., *Trichuris trichuria*, *Wuchereria bancrofti*.

It is furthermore possible to control protozoa, such as Eimeria.

From the order of the Heteroptera, for example, *Anasa tristis*, *Antestiopsis* spp., *Blissus* spp., *Calocoris* spp., *Campylomma livida*, *Cavelerius* spp., *Cimex* spp., *Creontiades dilutus*, *Dasynus piperis*, *Dichelops furcatus*, *Diconocoris hewetti*, *Dysdercus* spp., *Euschistus* spp., *Eurygaster* spp., *Heliopeltis* spp., *Horcias nobilellus*, *Leptocorisa* spp., *Leptoglossus phyllopus*, *Lygus* spp., *Macropes excavatus*, *Miridae*, *Nezara* spp., *Oebalus* spp., *Pentomidae*, *Piesma quadrata*, *Piezodorus* spp., *Psallus seriatus*, *Pseudacysta persea*, *Rhodnius* spp., *Sahlbergella singularis*, *Scotinophora* spp., *Stephanitis nashi*, *Tibraca* spp., *Triatoma* spp.

From the order of the Homoptera, for example, *Acyrthosipon* spp., *Aeneolamia* spp., *Agonoscena* spp., *Aleurodes* spp., *Aleurolobus barodensis*, *Aleurothrixus* spp., *Amraca* spp., *Anuraphis cardui*, *Aonidiella* spp., *Aphanostigma piri*, *Aphis* spp., *Arboridia apicalis*, *Aspidiella* spp., *Aspidiotus* spp., *Atanus* spp., *Aulacorthum solani*, *Bemisia* spp., *Brachycaudus helichrysii*, *Brachycolus* spp., *Brevicoryne brassicae*, *Calligypona marginata*, *Carneocephala fulgida*, *Ceratovacuna lanigera*, *Cercopidae*, *Ceroplastes* spp., *Chaetosiphon fragaefolii*, *Chionaspis tegalensis*, *Chlorita onukii*, *Chromaphis juglandicola*, *Chrysomphalus ficus*, *Cicadulina mbila*, *Coccomytilus halli*, *Coccus* spp., *Cryptomyzus ribis*, *Dalbulus* spp., *Dialeurodes* spp., *Diaphorina* spp., *Diaspis* spp., *Doralis* spp., *Drosicha* spp., *Dysaphis* spp., *Dysmicoccus* spp., *Empoasca* spp., *Eriosoma* spp., *Erythroneura* spp., *Euscelis bilobatus*, *Geococcus coffeae*, *Homalodisca coagulata*, *Hyalopterus arundinis*, *Icerya* spp., *Idiocerus* spp., *Idioscopus* spp., *Laodelphax striatellus*, *Lecanium* spp., *Lepidosaphes* spp., *Lipaphis erysimi*, *Macrosiphum* spp., *Mahanarva fimbriolata*, *Melanaphis sacchari*, *Metcalfiella* spp., *Metopolophium dirhodum*, *Monellia costalis*, *Monelliopsis pecanis*, *Myzus* spp., *Nasonovia ribisnigri*, *Nephotettix* spp., *Nilaparvata lugens*, *Oncometopia* spp., *Orthezia praelonga*, *Parabemisia myricae*, *Paratrioza* spp., *Parlatoria* spp., *Pemphigus* spp., *Peregrinus maidis*, *Phenacoccus* spp., *Phloeomyzus passerinii*, *Phorodon humuli*, *Phylloxera* spp., *Pinnaspis aspidistrae*, *Planococcus* spp., *Protopulvinaria pyriformis*, *Pseudaulacaspis pentagona*, *Pseudococcus* spp., *Psylla* spp., *Pteromalus* spp., *Pyrilla* spp., *Quadraspidiotus* spp., *Quesada gigas*, *Rastrococcus* spp., *Rhopalosiphum* spp., *Saissetia* spp., *Scaphoides titanus*, *Schizaphis graminum*, *Selenaspidus articulatus*, *Sogata* spp., *Sogatella furcifera*, *Sogatodes* spp., *Stictocephala festina*, *Tenalaphara malayensis*, *Tinocallis caryaefoliae*, *Tomaspis* spp., *Toxoptera* spp., *Trialeurodes vaporariorum*, *Trioza* spp., *Typhlocyba* spp., *Unaspis* spp., *Viteus vitifolii*.

From the order of the Hymenoptera, for example, *Diprion* spp., *Hoplocampa* spp., *Lasius* spp., *Monomorium pharaonis*, *Vespa* spp.

From the order of the Isopoda, for example, *Armadillidium vulgare*, *Oniscus asellus*, *Porcellio scaber*.

From the order of the Isoptera, for example, *Reticulitermes* spp., *Odontotermes* spp.

From the order of the Lepidoptera, for example, *Acronicta major*, *Aedia leucomelas*, *Agrotis* spp., *Alabama argillacea*, *Anticarsia* spp., *Barathra brassicae*, *Bucculatrix thurberiella*, *Bupalus piniarius*, *Cacoecia podana*, *Capua reticulana*, *Carpocapsa pomonella*, *Cheimatobia brumata*, *Chilo* spp., *Choristoneura fumiferana*, *Clysia ambiguella*, *Cnaphalocerus* spp., *Earias insulana*, *Ephestia kuehniella*, *Euproctis chrysorrhoea*, *Euxoa* spp., *Feltia* spp., *Galleria mellonella*, *Helicoverpa* spp., *Heliothis* spp., *Hofmannophila pseudospretella*, *Homona magnanima*, *Hyponomeuta padella*, *Laphygma* spp., *Lithocolletis blancardella*, *Lithophane antennata*, *Loxagrotis albicosta*, *Lymantria* spp., *Malacosoma neustria*, *Mamestra brassicae*, *Mocis repanda*, *Mythimna separata*, *Oria* spp., *Oulema oryzae*, *Panolis flammea*, *Pectinophora gossypiella*, *Phyllocnistis citrella*, *Pieris* spp., *Plutella xylostella*, *Prodenia* spp., *Pseudaletia* spp., *Pseudoplusia includens*, *Pyrausta nubilalis*, *Spodoptera* spp., *Thermesia gemmatalis*, *Tinea pellionella*, *Tineola bisselliella*, *Tortrix viridana*, *Trichoplusia* spp.

From the order of the Orthoptera, for example, *Acheta domesticus*, *Blatta orientalis*, *Blattella germanica*, *Gryllotalpa* spp., *Leucophaea maderae*, *Locusta* spp., *Melanoplus* spp., *Periplaneta americana*, *Schistocerca gregaria*.

From the order of the Siphonaptera, for example, *Ceratophyllus* spp., *Xenopsylla cheopis*.

From the order of the Symphyla, for example, *Scutigerella immaculata*.

From the order of the Thysanoptera, for example, *Baliothrips biformis*, *Enneothrips flavens*, *Frankliniella* spp., *Heliothrips* spp., *Hercinothrips femoralis*, *Kakothrips* spp., *Rhipiphorothrips cruentatus*, *Scirtothrips* spp., *Taeniothrips cardamoni*, *Thrips* spp.

From the order of the Thysanura, for example, *Lepisma saccharina*.

The phytoparasitic nematodes include, for example, *Anguina* spp., *Aphelenchoides* spp., *Belonoaimus* spp., *Bursaphelenchus* spp., *Ditylenchus dipsaci*, *Globodera* spp., *Heliocotylenchus* spp., *Heterodera* spp., *Longidorus* spp., *Meloidogyne* spp., *Pratylenchus* spp., *Radopholus similis*, *Rotylenchus* spp., *Trichodorus* spp., *Tylenchorhynchus* spp., *Tylenchulus* spp., *Tylenchulus semipenetrans*, *Xiphinema* spp.

If appropriate, the compounds according to the invention can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (Mycoplasma-like organisms) and RLO (Rickettsia-like organisms). If appropriate, they can also be employed as intermediates or precursors for the synthesis of other active compounds.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and genetic engineering methods or by combinations of these methods, including the transgenic plants and including the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offshoots and seeds.

Treatment according to the invention of the plants and plant parts with the active compounds is carried out directly or by allowing the compounds to act on the surroundings, habitat or storage space by the customary treatment methods, for example by immersion, spraying, evaporation, fogging, scattering, painting on, injection and, in the case of propagation material, in particular in the case of seeds, also by applying one or more coats.

The active compounds can be converted to the customary formulations, such as solutions, emulsions, wettable powders, water- and oil-based suspensions, powders, dusts, pastes, soluble powders, soluble granules, granules for broadcasting, suspension-emulsion concentrates, natural materials impregnated with active compound, synthetic materials impregnated with active compound, fertilizers and microencapsulations in polymeric substances.

These formulations are produced in a known manner, for example by mixing the active compounds with extenders, that is liquid solvents and/or solid carriers, optionally with the use of surfactants, that is emulsifiers and/or dispersants and/or foam-formers. The formulations are prepared either in suitable plants or else before or during the application.

Suitable for use as auxiliaries are substances which are suitable for imparting to the composition itself and/or to preparations derived therefrom (for example spray liquors, seed dressings) particular properties such as certain technical properties and/or also particular biological properties. Typical suitable auxiliaries are: extenders, solvents and carriers.

Suitable extenders are, for example, water, polar and non-polar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethyl sulphoxide, and also water.

Suitable solid carriers are:

for example, ammonium salts and ground natural minerals such as kaolins, clays, talc, chalk, quartz, attapulgite, montmorillonite or diatomaceous earth, and ground synthetic minerals, such as finely divided silica, alumina and silicates; suitable solid carriers for granules are: for example, crushed and fractionated natural rocks such as calcite, marble, pumice, sepiolite and dolomite, and also synthetic granules of inorganic and organic meals, and granules of organic material such as paper, sawdust, coconut shells, maize cobs and tobacco stalks; suitable emulsifiers and/or foam-formers are: for example, nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersants are nonionic and/or ionic substances, for example from the classes of the alcohol-POE- and/or -POP-ethers, acid and/or POP-POE esters, alkyl aryl and/or POP-POE ethers, fat- and/or POP-POE adducts, POE- and/or POP-polyol derivatives, POE- and/or POP-sorbitan- or -sugar adducts, alkyl or aryl sulphates, alkyl- or arylsulphonates and alkyl or aryl phosphates or the corresponding PO-ether adducts. Furthermore, suitable oligo- or polymers, for example those derived from vinylic monomers, from acrylic acid, from EO and/or PO alone or in combination with, for example, (poly)alcohols or (poly)amines. It is also possible to employ lignin and its sulphonic acid derivatives, unmodified and modified celluloses, aromatic and/or aliphatic sulphonic acids and their adducts with formaldehyde.

Tackifiers such as carboxymethylcellulose and natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Other possible additives are perfumes, mineral or vegetable, optionally modified oils, waxes and nutrients (including trace nutrients), such as salts of iron, manganese, boron, copper, cobalt, molybdenum and zinc.

Stabilizers, such as low-temperature stabilizers, preservatives, antioxidants, light stabilizers or other agents which improve chemical and/or physical stability may also be present.

The formulations generally comprise between 0.01 and 98% by weight of active compound, preferably between 0.5 and 90%.

The active compound according to the invention can be used in its commercially available formulations and in the use forms, prepared from these formulations, as a mixture with other active compounds, such as insecticides, attractants, sterilizing agents, bactericides, acaricides, nematicides, fungicides, growth-regulating substances, herbicides, safeners, fertilizers or semiochemicals. A mixture with other known active compounds, such as herbicides, fertilizers, growth regulators, safeners, semiochemicals, or else with agents for improving the plant properties, is also possible.

When used as insecticides, the active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

When used as insecticides, the active compounds according to the invention can furthermore be present in their commercially available formulations and in the use forms, prepared from these formulations, as a mixture with inhibitors which reduce degradation of the active compound after use in the environment of the plant, on the surface of parts of plants or in plant tissues.

The active compound content of the use forms prepared from the commercially available formulations can vary within wide limits. The active compound concentration of the use forms can be from 0.00000001 to 95% by weight of active compound, preferably between 0.00001 and 1% by weight.

The compounds are employed in a customary manner appropriate for the use forms.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (Genetically Modified Organisms), and parts thereof are treated. The terms "parts", "parts of plants" and "plant parts" have been explained above.

Particularly preferably, plants of the plant cultivars which are in each case commercially available or in use are treated according to the invention. Plant cultivars are to be understood as meaning plants having novel properties ("traits") which have been obtained by conventional breeding, by mutagenesis or by recombinant DNA techniques. These can be cultivars, bio- or genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products are possible, which exceed the effects which were actually to be expected.

The transgenic plants or plant cultivars (obtained by genetic engineering) which are preferably to be treated according to the invention include all plants which, by virtue of the genetic modification, received genetic material which imparted particularly advantageous, useful traits to these plants. Examples of such traits are better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products. Further and particularly emphasized examples of such traits are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, sugar beet, tomatoes, peas and other vegetable varieties, cotton, tobacco, oilseed rape and also fruit plants (with the fruits apples, pears, citrus fruits and grapes), and particular emphasis is given to maize, soya beans, potatoes, cotton, tobacco and oilseed rape. Traits that are emphasized are in particular increased defence of the plants against insects, arachnids, nematodes and slugs and snails by virtue of toxins formed in the plants, in particular those formed in the plants by the genetic material from Bacillus thuringiensis (for example by the genes CryIA(a), CryIA(b), CryIA(c), CryIIA, CryIIIA, CryIIIB2, Cry9c, Cry2Ab, Cry3Bb and CryIF and also combinations thereof) (referred to hereinbelow as "Bt plants"). Traits that are also particularly emphasized are the increased defence of the plants against fungi, bacteria and viruses by systemic acquired resistance (SAR), systemin, phytoalexins, elicitors and resistance genes and correspondingly expressed proteins and toxins. Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these genetic traits or genetic traits still to be developed, which plant cultivars will be developed and/or marketed in the future.

The plants listed can be treated according to the invention in a particularly advantageous manner with the compounds of the general formula I and/or the active compound mixtures according to the invention. The preferred ranges stated above for the active compounds or mixtures also apply to the treatment of these plants. Particular emphasis is given to the treatment of plants with the compounds or mixtures specifically mentioned in the present text.

The active compounds according to the invention act not only against plant, hygiene and stored product pests, but also in the veterinary medicine sector against animal parasites (ecto- and endoparasites), such as hard ticks, soft ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp., *Solenopotes* spp.

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp.

From the order of the Siphonapterida, for example, *Pulex* spp., *Ctenocephalides* spp., *Xenopsylla* spp., *Ceratophyllus* spp.

From the order of the Heteropterida, for example, *Cimex* spp., *Triatoma* spp., *Rhodnius* spp., *Panstrongylus* spp.

From the order of the Blattarida, for example, *Blatta orientalis, Periplaneta americana, Blattela germanica, Supella* spp.

From the subclass of the Acari (Acarina) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp., *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

The active compounds of the formula (I) according to the invention are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice. By controlling these arthropods, cases of death and reduction in productivity (for meat, milk, wool, hides, eggs, honey etc.) should be diminished, so that more economic and easier animal husbandry is possible by use of the active compounds according to the invention.

The active compounds according to the invention are used in the veterinary sector and in animal husbandry in a known manner by enteral administration in the form of, for example, tablets, capsules, potions, drenches, granules, pastes, boluses, the feed-through process and suppositories, by parenteral administration, such as, for example, by injection (intramuscular, subcutaneous, intravenous, intraperitoneal and the like), implants, by nasal administration, by dermal use in the form, for example, of dipping or bathing, spraying, pouring on and spotting on, washing and powdering, and also with the aid of moulded articles containing the active compound, such as collars, ear marks, tail marks, limb bands, halters, marking devices and the like.

When used for cattle, poultry, pets and the like, the active compounds of the formula (I) can be used as formulations (for example powders, emulsions, free-flowing compositions), which comprise the active compounds in an amount of 1 to 80% by weight, directly or after 100 to 10 000-fold dilution, or they can be used as a chemical bath.

It has furthermore been found that the compounds according to the invention also have a strong insecticidal action against insects which destroy industrial materials.

The following insects may be mentioned as examples and as preferred—but without any limitation:

Beetles, such as *Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec. *Tryptodendron* spec. *Apate monachus, Bostrychus capucins, Heterobostrychus brunneus, Sinoxylon* spec. *Dinoderus minutus;*

Hymenopterons, such as *Sirex juvencus, Urocerus gigas, Urocerus gigas taignus, Urocerus augur;*

Termites, such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus;*

Bristletails, such as *Lepisma saccharina.*

Industrial materials in the present connection are to be understood as meaning non-living materials, such as, preferably, plastics, adhesives, sizes, papers and cardboards, leather, wood and processed wood products and coating compositions.

The ready-to-use compositions may, if appropriate, comprise further insecticides and, if appropriate, one or more fungicides.

With respect to possible additional additives, reference may be made to the insecticides and fungicides mentioned above.

The compounds according to the invention can likewise be employed for protecting objects which come into contact with saltwater or brackish water, such as hulls, screens, nets, buildings, moorings and signalling systems, against fouling.

Furthermore, the compounds according to the invention, alone or in combinations with other active compounds, may be employed as antifouling agents.

In domestic, hygiene and stored-product protection, the active compounds are also suitable for controlling animal pests, in particular insects, arachnids and mites, which are found in enclosed spaces such as, for example, dwellings, factory halls, offices, vehicle cabins and the like. They can be employed alone or in combination with other active compounds and auxiliaries in domestic insecticide products for controlling these pests. They are active against sensitive and resistant species and against all developmental stages. These pests include:

From the order of the Scorpionidea, for example, *Buthus occitanus*.

From the order of the Acarina, for example, *Argas persicus, Argas reflexus, Bryobia* ssp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae*.

From the order of the Araneae, for example, Aviculariidae, Araneidae.

From the order of the Opiliones, for example, *Pseudoscorpiones chelifer, Pseudoscorpiones cheiridium, Opiliones phalangium*.

From the order of the Isopoda, for example, *Oniscus asellus, Porcellio scaber*.

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus*.

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa*.

From the order of the Saltatoria, for example, *Acheta domesticus*.

From the order of the Dermaptera, for example, *Forficula auricularia*.

From the order of the Isoptera, for example, *Kalotermes* spp., *Reticulitermes* spp.

From the order of the Psocoptera, for example, *Lepinatus* spp., *Liposcelis* spp.

From the order of the Coleoptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum*.

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa*.

From the order of the Lepidoptera, for example, *Achroia grisella, Galleria mellonella, Plodia interpunctella, Tinea cloacella, Tinea pellionella, Tineola bisselliella*.

From the order of the Siphonaptera, for example, *Ctenocephalides canis, Ctenocephalides felis, Pulex irritans, Tunga penetrans, Xenopsylla cheopis*.

From the order of the Hymenoptera, for example, *Camponotus herculeanus, Lasius fuliginosus, Lasius niger, Lasius umbratus, Monomorium pharaonis, Paravespula* spp., *Tetramorium caespitum*.

From the order of the Anoplura, for example, *Pediculus humanus capitis, Pediculus humanus corporis, Pemphigus* spp., *Phylloera vastatrix, Phthirus pubis*.

From the order of the Heteroptera, for example, *Cimex hemipterus, Cimex lectularius, Rhodinus prolixus, Triatoma infestans*.

In the field of household insecticides, they are used alone or in combination with other suitable active compounds, such as phosphoric esters, carbamates, pyrethroids, neonicotinoids, growth regulators or active compounds from other known classes of insecticides.

They are used in aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive, evaporation systems, moth papers, moth bags and moth gels, as granules or dusts, in baits for spreading or in bait stations.

The active compounds according to the invention can also be used as defoliants, desiccants, haulm killers and, in particular, as weed killers. Weeds in the broadest sense are understood as meaning all plants which grow at locations where they are undesired. Whether the substances according to the invention act as nonselective or selective herbicides depends essentially on the application rate.

The active compounds according to the invention can be used for example in the following plants:

Dicotyledonous weeds of the genera: *Abutilon, Amaranthus, Ambrosia, Anoda, Anthemis, Aphanes, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium*.

Dicotyledonous crops of the genera: *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia*.

Monocotyledonous weeds of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum*.

Monocotyledonous crops of the genera: *Allium, Ananas, Asparagus, Avena, Hordeum, Oryza, Panicum, Saccharum, Secale, Sorghum, Triticale, Triticum, Zea*.

However, the use of the active compounds according to the invention is in no way restricted to these genera, but extends in the same manner to other plants.

Depending on the concentration, the active compounds according to the invention are suitable for the nonselective weed control on, for example, industrial terrains and railway tracks and on paths and locations with and without trees. Likewise the active compounds according to the invention can be employed for controlling weeds in perennial crops, for example forests, ornamental tree plantings, orchards, vineyards, citrus groves, nut orchards, banana plantations, coffee plantations, tea plantations, rubber plantations, oil palm plantations, cocoa plantations, soft fruit plantings and hop fields, on lawns, turf and pastureland, and for the selective control of weeds in annual crops.

The active compounds according to the invention have strong herbicidal activity and a broad activity spectrum when used on the soil and on aerial plant parts. To a certain extent, they are also suitable for the selective control of monocotyledonous and dicotyledonous weeds in monocotyledonous and dicotyledonous crops, both pre- and post-emergence.

At certain concentrations or application rates, the active compounds according to the invention can also be employed for controlling animal pests and fungal or bacterial plant diseases. If appropriate, they can also be used as intermediates or precursors for the synthesis of other active compounds.

The active compounds can be converted into the customary formulations, such as solutions, emulsions, wettable powders, suspensions, powders, dusting agents, pastes, soluble powders, granules, suspoemulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surfactants, that is emulsifiers and/or dispersants and/or foam-formers.

If the extender used is water, it is also possible to use, for example, organic solvents as auxiliary solvents. Suitable liquid solvents are essentially: aromatics, such as xylene, toluene or alkyl-naphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol, and also their ethers and esters, ketones, such as acetone, methyl ethyl ketone, methyl isobutyl ketone or cyclohexanone, strongly polar solvents, such as dimethylformamide and dimethyl sulphoxide, and also water.

Suitable solid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and silicates, suitable solid carriers for granules are: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks; suitable emulsifiers and/or foam-formers are: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: for example lignosulphite waste liquors and methylcellulose.

Tackifiers such as carboxymethylcellulose and natural and synthetic polymers in the form of powders, granules or latices, such as gum arabic, polyvinyl alcohol and polyvinyl acetate, and also natural phospholipids, such as cephalins and lecithins, and synthetic phospholipids, can be used in the formulations. Other possible additives are mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 percent by weight of active compound, preferably between 0.5 and 90%.

The active compounds according to the invention, as such or in their formulations, can also be used for weed control purposes as a mixture with known herbicides and/or with substances which improve crop plant tolerance ("safeners"), ready mixes or tank mixes being possible. Mixtures with herbicide products which contain one or more known herbicides and a safener are hence also possible.

A mixture with other known active compounds, such as fungicides, insectides, insecticides, acaricides, nematicides, bird repellents, plant nutrients and soil conditioners, is also possible.

The active compounds can be applied as such, in the form of their formulations or the use forms prepared therefrom by further dilution, such as ready-to-use solutions, suspensions, emulsions, powders, pastes and granules. They are applied in the customary manner, for example by pouring, spraying, atomizing, spreading.

The active compounds according to the invention can be applied both before and after plant emergence. They can also be incorporated into the soil prior to planting.

The application rate of active compound can vary within a substantial range. Essentially, it depends on the nature of the desired effect. In general, the application rates are between 1 g and 10 kg of active compound per hectare of soil area, preferably between 5 g and 5 kg per ha.

The advantageous effect of the compatibility with crop plants of the active compound combinations according to the invention is particularly pronounced at certain concentration ratios. However, the weight ratios of the active compounds in the active compound combinations can be varied within relatively wide ranges. In general, salts from 0.001 to 1000 parts by weight, preferably from 0.01 to 100 parts by weight, particularly preferably 0.05 to 20 parts by weight, of one of the compounds which improves crop plant compatibility (antidotes/safeners) mentioned above under (b') are present per part by weight of active compound of the formula (I).

The active compounds according to the invention are generally applied in the form of finished formulations. However, the active compounds contained in the active compound combinations can, as individual formulations, also be mixed during use, i.e. be applied in the form of tank mixes.

For certain applications, in particular by the post-emergence method, it may furthermore be advantageous to include, as further additives in the formulations, mineral or vegetable oils which are tolerated by plants (for example the commercial preparation "Rako Binol"), or ammonium salts, such as, for example, ammonium sulphate or ammonium thiocyanate.

The novel active compounds can be used as such, in the form of their formulations or the use forms prepared therefrom by further dilution, such as ready-to-use solutions, suspensions, emulsions, powders, pastes and granules. Application is in the customary manner, for example by pouring, spraying, atomizing, dusting or scattering.

The application rates of the active compounds according to the invention can be varied within a certain range; they depend, inter alia, on the weather and on soil factors. In general, the application rates are between 0.001 and 5 kg per ha, preferably between 0.005 and 2 kg per ha, particularly preferably between 0.01 and 0.5 kg per ha.

The active compounds according to the invention can be applied before and after emergence of the plants, that is to say by the pre-emergence and post-emergence method.

Depending on their properties, the safeners to be used according to the invention can be used for pretreating the seed of the crop plant (seed dressing) or can be introduced into the seed furrows prior to sowing or be used separately prior to the herbicide or together with the herbicide, before or after emergence of the plants.

Examples of plants which may be mentioned are important crop plants, such as cereals (wheat, barley, rice), maize, soybeans, potatoes, cotton, oilseed rape, beet, sugar cane and also fruit plants (with the fruits apples, pears, citrus fruits and grapevines), greater emphasis being given to cereals, maize, soybeans, potatoes, cotton and oilseed rape.

The term "active compounds" always also includes the active compound combinations mentioned here.

Preparation and use of the active compounds according to the invention is illustrated by the examples below.

PREPARATION EXAMPLES

Example I-1-a-1, I-1-a-2

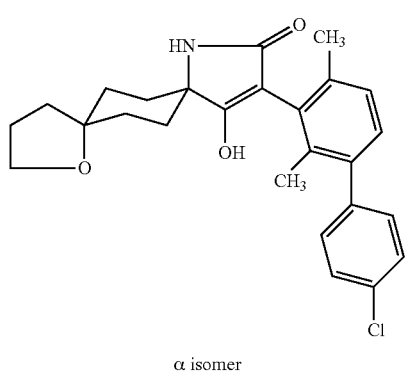

α isomer

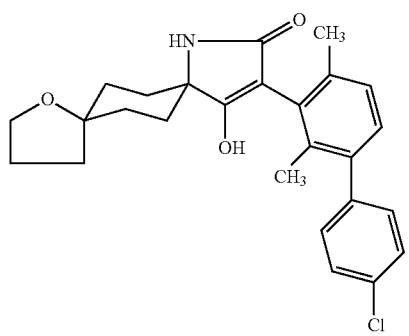

β isomer 0.95 g (8.5 mmol) of potassium tert-butoxide is initially charged to 3 ml of N,N-dimethylacetamide (DMA). At 60° C., 1.6 g (3.4 mmol) of the compound according to Example II-1 are added dropwise, and the stirring is continued for 1.5 h. The reaction mixture is poured into ice-water, acidified with dilute hydrochloric acid and filtered off with suction. The residue is pre-purified by medium-pressure chromatography on silica gel using a cyclohexane/ethyl acetate gradient (50%-80%). Further purification by HPLC (Kromasil 100 C18) using acetonitrile/water/formic acid 43:56:1 gives 0.16 g (10.7% of theory) of the compound I-1-a-1 of m.p. 311° C. and 0.08 g (5.4% of theory) of the compound I-1-a-2 of m.p. 307° C.

Example I-1-a-46

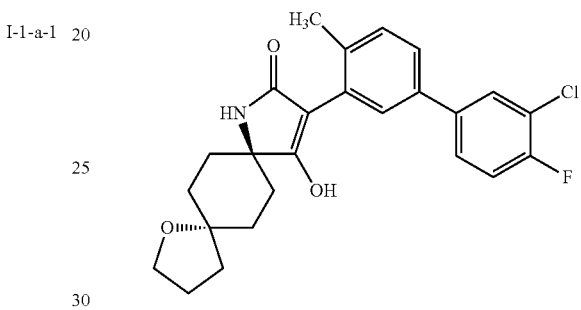

0.588 g (1.5 mmol) of the compound according to Ex. I-1-a-28, 0.314 g (1.8 mmol) of 3-chloro-4-fluorophenylboronic acid and 0.8 g (7.5 mmol) of sodium carbonate are initially charged in 15 ml of water, 37 mg (0.15 mmol) of palladium(II) nitrate dihydrate are added and the mixture is stirred in a preheated oil bath at 130° C. overnight. After cooling, the mixture is acidified with dil. hydrochloric acid and filtered off with suction. The aqueous phase is extracted with methylene chloride and the organic phase is dried over sodium sulphate, filtered and concentrated. Both fractions are purified together by MPLC on a reversed-phase cartridge using cyclohexane+0-40% acetone (gradient).

Yield: 0.25 g (=37% of theory) m.p. 259° C.

Analogously to Examples (I-1-a-1), (I-1-a-2), (I-1-a-46) and in accordance with the general statements on the preparation, the following compounds of the formula (I-1-a) are obtained

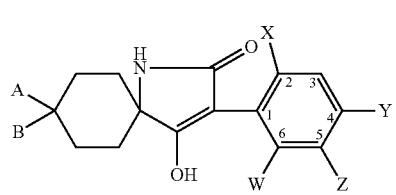

(I-1-a)

| Ex. No. | W | X | Y | Z | A | B | m.p. °C. | Isomer |
|---|---|---|---|---|---|---|---|---|
| I-1-a-3 | CH$_3$ | CH$_3$ | CH$_3$ | H | —O—(CH$_2$)$_3$— | | 314 | α:β about 19:1 |
| I-1-a-4 | CH$_3$ | CH$_3$ | CH$_3$ | H | —O—(CH$_2$)$_3$— | | 281 | α:β about 3:7 |
| I-1-a-5 | CH$_3$ | CH$_3$ | Cl | H | —O—(CH$_2$)$_3$— | | 316 | α |
| I-1-a-6 | CH$_3$ | CH$_3$ | Cl | H | —O—(CH$_2$)$_3$— | | 289 | α:β about 2:3 |

-continued

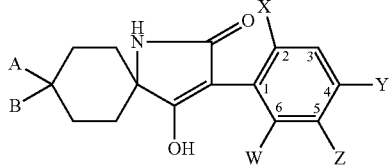

(I-1-a)

| Ex. No. | W | X | Y | Z | A—B | m.p. °C. | Isomer |
|---|---|---|---|---|---|---|---|
| I-1-a-7 | CH₃ | CH₃ | Br | H | —O—(CH₂)₃— | 300 | α |
| I-1-a-8 | CH₃ | CH₃ | Br | H | —O—(CH₂)₃— | 273 | α:β about 3:7 |
| I-1-a-9 | C₂H₅ | Br | CH₃ | H | —O—(CH₂)₃— | 266 | α |
| I-1-a-10 | C₂H₅ | Br | CH₃ | H | —O—(CH₂)₃— | 261 | α:β about 5:4 |
| I-1-a-11 | C₂H₅ | OCH₃ | Cl | H | —O—(CH₂)₃— | 226 | mixture α + β |
| I-1-a-12 | C₂H₅ | OC₂H₅ | Cl | H | —O—(CH₂)₃— | 159 | α:β about 1:6 |
| I-1-a-13 | Cl | OCH₃ | CH₃ | H | —O—(CH₂)₃— | 216 | mixture |
| I-1-a-14 | CH₃ | CH₃ | H | Br | —O—(CH₂)₃— | 280 | α:β about 1:4 |
| I-1-a-15 | CH₃ | CH₃ | H | Br | —O—(CH₂)₃— | 286 | α |
| I-1-a-16 | H | CH₃ | Cl | CH₃ | —O—(CH₂)₃— | 270 | β |
| I-1-a-17 | H | CH₃ | Cl | CH₃ | —O—(CH₂)₃— | 265 | α |
| I-1-a-18 | H | CH₃ | CH₃ | CH₃ | —O—(CH₂)₃— | 134 | α:β 3:7 |
| I-1-a-19 | H | CH₃ | CH₃ | CH₃ | —O—(CH₂)₃— | 271 | α |
| I-1-a-20 | Br | Br | OCF₃ | H | —O—(CH₂)₃— | oil | β |
| I-1-a-21 | Br | Br | OCF₃ | H | —O—(CH₂)₃— | 275 | α |
| I-1-a-22 | CH₃ | CH₃ | ▷— | H | —O—(CH₂)₃— | 274 | α:β about 7:3 |
| I-1-a-23 | CH₃ | CH₃ | ▷— | H | —O—(CH₂)₃— | 269 | α:β about 1:10 |
| I-1-a-24 | CH₃ | CH₃ | I | H | —O—(CH₂)₃— | 267 | α:β about 2:1 |
| I-1-a-25 | CH₃ | CH₃ | I | H | —O—(CH₂)₃— | 282 | α |
| I-1-a-26 | H | Cl | F | H | —O—(CH₂)₃— | 269 | mixture |
| I-1-a-27 | H | Cl | CH₃ | H | —O—(CH₂)₃— | 281 | mixture |
| I-1-a-28 | H | CH₃ | H | Br | —O—(CH₂)₃— | oil | α + β about 7:2 |
| I-1-a-29 | H | CH₃ | H | Br | —O—(CH₂)₃— | 261 | β |
| I-1-a-30 | H | Br | H | CH₃ | —O—(CH₂)₃— | 236 | mixture |
| I-1-a-31 | H | CH₃ | H | CH₃ | —O—(CH₂)₃— | 220 | α + β about 1:1 |
| I-1-a-32 | H | CH₃ | H | CH₃ | —O—(CH₂)₃— | 234 | α |
| I-1-a-33 | H | Cl | H | H | —O—(CH₂)₃— | 248 | mixture |
| I-1-a-34 | H | CH₃ | H | H | —O—(CH₂)₃— | 237 | α:β about 1:2 |
| I-1-a-35 | H | CH₃ | H | H | —O—(CH₂)₃— | 267 | α |
| I-1-a-36 | H | CH₃ | CH₃ | H | —O—(CH₂)₃— | 244 | α:β about 2:1 |
| I-1-a-37 | H | CH₃ | F | H | —O—(CH₂)₃— | 265 | α:β about 1:1 |
| I-1-a-38 | H | CH₃ | F | H | —O—(CH₂)₃— | 283 | α |
| I-1-a-39 | H | CH₃ | Cl | H | —O—(CH₂)₃— | 276 | α:β about 1:1 |
| I-1-a-40 | CH₃ | OCH₃ | Cl | H | —O—(CH₂)₃— | 271 | β |
| I-1-a-41 | CH₃ | OCH₃ | Cl | H | —O—(CH₂)₃— | 268 | α |
| I-1-a-42 | C₂H₅ | OC₂H₅ | Cl | H | —O—(CH₂)₃— | 237 | α |
| I-1-a-43 | H | CH₃ | H | 4-F—Ph | —O—(CH₂)₃— | 225 | α |
| I-1-a-44 | H | CH₃ | H | 4-F—Ph | —O—(CH₂)₃— | 247 | β |
| I-1-a-45 | H | CH₃ | H | 3,4-F₂—Ph | —O—(CH₂)₃— | 256 | α:β about 9:1 |
| I-1-a-46 | H | CH₃ | H | 3-Cl,4-F—Ph | —O—(CH₂)₃— | 259 | α |
| I-1-a-47 | CH₃ | Cl | CH₃ | H | —O—(CH₂)₃— | 316-318 | β |
| I-1-a-48 | CH₃ | C₂H₅ | CH₃ | H | —O—(CH₂)₃— | 301-304 | β |
| I-1-a-49 | C₂H₅ | Br | CH₃ | H | —O—(CH₂)₃— | 300-302 | α |
| I-1-a-50 | C₂H₅ | Br | CH₃ | H | —O—(CH₂)₃— | 288-290 | β |
| I-1-a-51 | C₂H₅ | C₂H₅ | CH₃ | H | —O—(CH₂)₃— | 220-223 | α |
| I-1-a-52 | C₂H₅ | C₂H₅ | CH₃ | H | —O—(CH₂)₃— | 307-310 | β |
| I-1-a-53 | CH₃ | C₂H₅ | CH₃ | H | —O—(CH₂)₃— | 248-250 | α |

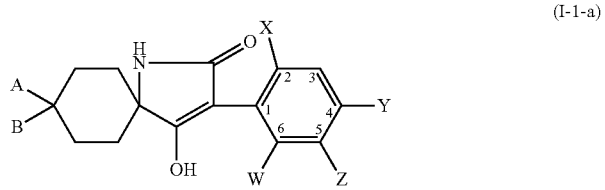

(I-1-a)

| Ex. No. | W | X | Y | Z | A | B | m.p. ° C. | Isomer |
|---|---|---|---|---|---|---|---|---|
| I-1-a-54 | C₂H₅ | ▷ | CH₃ | H | —O—(CH₂)₃— | | 215-219 | α |
| I-1-a-55 | C₂H₅ | ▷ | CH₃ | H | —O—(CH₂)₃— | | 293-295 | β |
| I-1-a-56 | H | C₂H₅ | CH₃ | H | —O—(CH₂)₃— | | 202-206 | α |
| I-1-a-57 | H | C₂H₅ | CH₃ | H | —O—(CH₂)₃— | | 259-263 | β |
| I-1-a-58 | CH₃ | Cl | CH₃ | H | —O—(CH₂)₃— | | 291-294 | α |

Example I-1-b-1

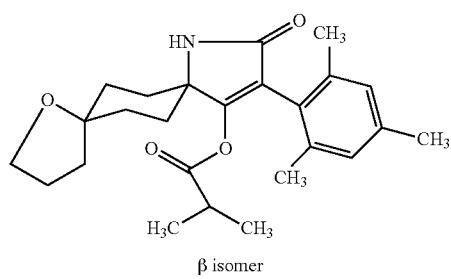 [SMILES: Cc1cc(C)c(C2=C(OC(=O)C(C)C)C3(CCC4(CCCO4)CC3)NC2=O)c(C)c1]

β isomer 0.512 g (1.5 mmol) of the compound according to Example (I-1-a-4) is initially charged in 15 ml of ethyl acetate (EA), and 0.21 ml (1.5 mmol) of triethylamine and 10 mg of 4-N,N-dimethylaminopyridine are added. Under reflux, 0.16 ml (1.5 mmol) of isobutyryl chloride in 1.5 ml of EA is added dropwise, and the mixture is stirred for another 2 h. After cooling, the mixture is concentrated and the residue is chromatographed by MPLC on silica gel using cyclohexane/acetone 7:3. This gives 0.46 g (70% of theory) of melting point 211° C.

Analogously to Example (I-1-b-1) and in accordance with the general statements on the preparation, the following compounds of the formula (I-1-b) are obtained (I-1-b)

| Ex. No. | W | X | Y | Z | A | B | R¹ | m.p. ° C. | Isomer |
|---|---|---|---|---|---|---|---|---|---|
| I-1-b-2 | CH₃ | CH₃ | Cl | H | —O—(CH₂)₃— | | i-C₃H₇ | 241 | α:β about 1:1 |
| I-1-b-3 | CH₃ | CH₃ | CH₃ | H | —O—(CH₂)₃— | | i-C₃H₇ | 236 | α |
| I-1-b-4 | CH₃ | CH₃ | CH₃ | H | —O—(CH₂)₃— | | ▷ | 235 | α |
| I-1-b-5 | CH₃ | CH₃ | CH₃ | H | —O—(CH₂)₃— | | ▷ | 236 | β |
| I-1-b-6 | CH₃ | CH₃ | CH₃ | H | —O—(CH₂)₃— | | CH₃O—CH₂— | 206 | α |
| I-1-b-7 | CH₃ | CH₃ | CH₃ | H | —O—(CH₂)₃— | | CH₃O—CH₂— | decomp. | β |

Example I-1-c-1

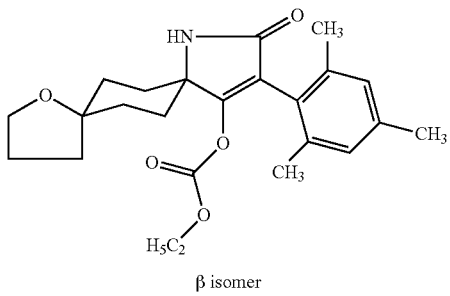

β isomer 350 mg of the compound according to Example (I-1-a-4) are initially charged in 10 ml of dichloromethane, and 0.14 ml of triethylamine is added. At room temperature, 0.1 ml of ethyl chloroformate in 1 ml of dichloromethane is added dropwise, and stirring is continued for 2 h. The solvent is evaporated and the residue is chromatographed by MPLC on silica gel using cyclohexane/acetone 7:3. The fraction obtained is concentrated and taken up in methanol, and the product is precipitated with water and filtered off with suction. Yield: 0.11 g (25% of theory) of melting point 197° C.

Analogously to Example (I-1-c-1) and in accordance with the general statements on the preparation, the following compounds of the formula (I-1-c) are obtained:

Example II-1

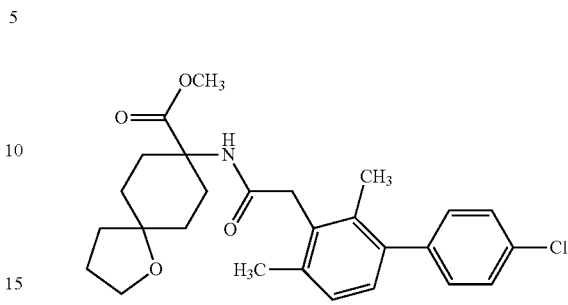

2.75 g of the compound according to Example (XVI-1) are initially charged in 20 ml of ethyl acetate, 11 ml of aqueous sodium hydroxide solution are added at 0° C. and 2.75 g of 2,6-dimethyl-3-(4-chlorophenyl)phenylacetyl chloride, dissolved in 10 ml of ethyl acetate, and the remaining aqueous sodium hydroxide solution (10 ml) are then added simultaneously with vigorous stirring. After the reaction has ended, (I-1-c)

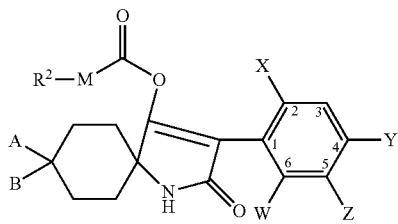

| Ex. No. | W | X | Y | Z | A | B | M | $R^2$ | m.p. °C. | Isomer |
|---|---|---|---|---|---|---|---|---|---|---|
| I-1-c-2 | $CH_3$ | $CH_3$ | Cl | H | —O—$(CH_2)_3$— | | O | $C_2H_5$ | 227 | α |
| I-1-c-3 | $CH_3$ | $CH_3$ | Cl | H | —O—$(CH_2)_3$— | | O | $C_2H_5$ | 208 | α:β about 87:12 |
| I-1-c-4 | $CH_3$ | $CH_3$ | Cl | H | —O—$(CH_2)_3$— | | O | $C_2H_5$ | * | β |
| I-1-c-5 | $CH_3$ | $CH_3$ | Br | H | —O—$(CH_2)_3$— | | O | $C_2H_5$ | 216 | β |
| I-1-c-6 | $CH_3$ | $CH_3$ | Br | H | —O—$(CH_2)_3$— | | O | $C_2H_5$ | decomp. | α |
| I-1-c-7 | $CH_3$ | $CH_3$ | $CH_3$ | H | —O—$(CH_2)_3$— | | O | $C_2H_5$ | 220 | α |
| I-1-c-8 | $CH_3$ | $CH_3$ | $CH_3$ | H | —O—$(CH_2)_3$— | | O | Ph—$CH_2$— | 199 | α |
| I-1-c-9 | $CH_3$ | $CH_3$ | $CH_3$ | H | —O—$(CH_2)_3$— | | O | Ph—$CH_2$— | 215 | β |
| I-1-c-10 | $C_2H_5$ | Br | $CH_3$ | H | —O—$(CH_2)_3$— | | O | $C_2H_5$ | 175-177 | β |
| I-1-c-11 | $C_2H_5$ | $C_2H_5$ | $CH_3$ | H | —O—$(CH_2)_3$— | | O | $C_2H_5$ | 190-193 | β |
| I-1-c-12 | $CH_3$ | $C_2H_5$ | $CH_3$ | H | —O—$(CH_2)_3$— | | O | $C_2H_5$ | 187-189 | β |
| I-1-c-13 | $C_2H_5$ | ▷ | $CH_3$ | H | —O—$(CH_2)_3$— | | O | $C_2H_5$ | 206-207 | β |
| I-1-c-14 | H | $C_2H_5$ | $CH_3$ | H | —O—$(CH_2)_3$— | | O | $C_2H_5$ | 172-174 | β |
| I-1-c-15 | $CH_3$ | Cl | $CH_3$ | H | —O—$(CH_2)_3$— | | O | $C_2H_5$ | 217-219 | β |
| I-1-c-16 | $CH_3$ | $C_2H_5$ | Br | H | —O—$(CH_2)_3$— | | O | $C_2H_5$ | 183-185 | β |
| I-1-c-17 | $C_2H_5$ | $C_2H_5$ | $CH_3$ | H | —O—$(CH_2)_3$— | | O | $C_2H_5$ | 199-201 | α |
| I-1-c-18 | $CH_3$ | $C_2H_5$ | $CH_3$ | H | —O—$(CH_2)_3$— | | O | $C_2H_5$ | 189-191 | α |
| I-1-c-19 | $C_2H_5$ | ▷ | $CH_3$ | H | —O—$(CH_2)_3$— | | O | $C_2H_5$ | 218-221 | α |
| I-1-c-20 | H | $C_2H_5$ | $CH_3$ | H | —O—$(CH_2)_3$— | | O | $C_2H_5$ | 211-213 | α |
| I-1-c-21 | $CH_3$ | Cl | $CH_3$ | H | —O—$(CH_2)_3$— | | O | $C_2H_5$ | 213-215 | α |

* $^1$H-NMR (400 MHz, $CD_3CN$): δ = 1.01 (t, 3H, $CO_2CH_2CH_3$), 2.11 (s, 6H, 2 × Ar—$CH_3$), 3.73 (cm, 2H, O—$CH_2$), 3.97-4.03 (q, 2H, $CO_2CH_2CH_3$) ppm the phases are separated, the aqueous phase is extracted with ethyl acetate and the combined organic phases are dried over sodium sulphate, filtered and concentrated.

MPLC: cyclohexane+30-50% ethyl acetate

Yield: 2 g (40% of theory), m.p. 172.8° C.

Analogously to Example (II-1) and in accordance with the general statements on the preparation, the following compounds of the formula (II) are obtained

(II)

| Ex. No. | W | X | Y | Z | A | B | R$^8$ | m.p. °C. | Isomer |
|---|---|---|---|---|---|---|---|---|---|
| II-2 | CH$_3$ | CH$_3$ | CH$_3$ | H | —O—(CH$_2$)$_3$— | | CH$_3$ | 157 | mixture |
| II-3 | CH$_3$ | CH$_3$ | Cl | H | —O—(CH$_2$)$_3$— | | CH$_3$ | 181 | mixture |
| II-4 | CH$_3$ | CH$_3$ | Br | H | —O—(CH$_2$)$_3$— | | CH$_3$ | 194 | mixture |
| II-5 | C$_2$H$_5$ | Br | CH$_3$ | H | —O—(CH$_2$)$_3$— | | CH$_3$ | 146 | mixture |
| II-6 | C$_2$H$_5$ | OCH$_3$ | Cl | H | —O—(CH$_2$)$_3$— | | CH$_3$ | 142 | mixture |
| II-7 | H | CH$_3$ | Cl | H | —O—(CH$_2$)$_3$— | | CH$_3$ | 149 | α:β about 1:1 |
| II-8 | H | Br | H | CH$_3$ | —O—(CH$_2$)$_3$— | | CH$_3$ | 151 | α:β about 1:1 |
| II-9 | H | Cl | CH$_3$ | H | —O—(CH$_2$)$_3$— | | CH$_3$ | 112 | α:β about 1:1 |
| II-10 | H | CH$_3$ | F | H | —O—(CH$_2$)$_3$— | | CH$_3$ | 160 | α:β about 1:1 |
| II-11 | H | CH$_3$ | CH$_3$ | H | —O—(CH$_2$)$_3$— | | CH$_3$ | 115 | α:β about 1:1 |
| II-12 | H | CH$_3$ | H | H | —O—(CH$_2$)$_3$— | | CH$_3$ | 141 | α:β about 1:1 |
| II-13 | H | Cl | H | H | —O—(CH$_2$)$_3$— | | CH$_3$ | 150 | α:β about 1:1 |
| II-14 | H | CH$_3$ | H | CH$_3$ | —O—(CH$_2$)$_3$— | | CH$_3$ | 160 | α:β about 1:1 |
| II-15 | H | CH$_3$ | H | Br | —O—(CH$_2$)$_3$— | | CH$_3$ | 148 | α:β about 1:1 |
| II-16 | H | Cl | F | H | —O—(CH$_2$)$_3$— | | CH$_3$ | 145 | α:β about 1:1 |
| II-17 | CH$_3$ | CH$_3$ | I | H | —O—(CH$_2$)$_3$— | | CH$_3$ | 211 | α:β about 1:1 |
| II-18 | CH$_3$ |  | CH$_3$ | H | —O—(CH$_2$)$_3$— | | CH$_3$ | 188 | α:β about 1:1 |
| II-19 | Br | Br | OCF$_3$ | H | —O—(CH$_2$)$_3$— | | CH$_3$ | 186 | α:β about 1:1 |
| II-20 | H | CH$_3$ | CH$_3$ | CH$_3$ | —O—(CH$_2$)$_3$— | | CH$_3$ | oil | α:β about 1:1 |
| II-21 | H | CH$_3$ | Cl | CH$_3$ | —O—(CH$_2$)$_3$— | | CH$_3$ | 161 | α:β about 1:1 |
| II-22 | CH$_3$ | CH$_3$ | H | Br | —O—(CH$_2$)$_3$— | | CH$_3$ | 177 | α:β about 1:1 |
| II-23 | Cl | OCH$_3$ | CH$_3$ | H | —O—(CH$_2$)$_3$— | | CH$_3$ | 162 | α:β about 1:1 |
| II-24 | CH$_3$ | OCH$_3$ | Cl | H | —O—(CH$_2$)$_3$— | | CH$_3$ | 170 | α:β about 1:1 |
| II-25 | C$_2$H$_5$ | OC$_2$H$_5$ | Cl | H | —O—(CH$_2$)$_3$— | | CH$_3$ | 166 | α:β about 1:1 |
| II-26 | CH$_3$ | Cl | CH$_3$ | H | —O—(CH$_2$)$_3$— | | CH$_3$ | 156-158 | mixture |
| II-27 | H | C$_2$H$_5$ | H | H | —O—(CH$_2$)$_3$— | | CH$_3$ | 98-100 | mixture |
| II-28 | C$_2$H$_5$ |  | CH$_3$ | H | —O—(CH$_2$)$_3$— | | CH$_3$ | 154-156 | mixture |
| II-29 | CH$_3$ | C$_2$H$_5$ | CH$_3$ | H | —O—(CH$_2$)$_3$— | | CH$_3$ | 131-135 | mixture |
| II-30 | C$_2$H$_5$ | C$_2$H$_5$ | CH$_3$ | H | —O—(CH$_2$)$_3$— | | CH$_3$ | 136-138 | mixture |
| II-31 | CH$_3$ | C$_2$H$_5$ | Br | H | —O—(CH$_2$)$_3$— | | CH$_3$ | 160-162 | mixture |

Example I-2-a-1

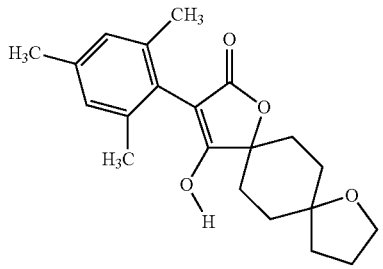 [SMILES: Cc1cc(C)c(C2=C(O)C3(CCC4(CCCO4)CC3)OC2=O)c(C)c1]

280 mg (0.72 mmol) of the compound according to Example III-1 are dissolved in 5 ml of DMF, 121 mg (1.08 mmol) of potassium tert-butoxide are added and the mixture is stirred at room temperature for 8 h. The mixture is concentrated using a rotary evaporator, the residue is partitioned between water and MTB ether, the aqueous phase is acidified with hydrochloric acid and the product is extracted with dichloromethane. The org. phase is dried and concentrated.

Yield 250 mg (quant.) as an about 1:1 cis/trans isomer mixture

NMR (400 MHz CDCl$_3$): δ=1.5-2.4 (m, 12H), 2.2 (s, 6H), 2.3 (s, 3H), 3.85 (m, 2H), 6.9 (s, 2H) ppm.

Analogously to Example (I-2-a-1) and in accordance with the general statements on the preparation, the following compounds of the formula (I-2-a) are obtained. Isolation of the isomers was carried out by

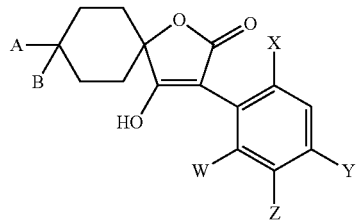

(I-2-a)

| Ex. No | W | X | Y | Z | A—B | log P* | Isomer |
|---|---|---|---|---|---|---|---|
| I-2-a-2 | H | CH$_3$ | H | CH$_3$ | —O—(CH$_2$)$_3$— | 2.73 | α |
| I-2-a-3 | H | CH$_3$ | H | CH$_3$ | —O—(CH$_2$)$_3$— | 2.29 | β |
| I-2-a-4 | CH$_3$ | CH$_3$ | CH$_3$ | H | —O—(CH$_2$)$_3$— | 2.52 | β |
| I-2-a-5 | CH$_3$ | CH$_3$ | CH$_3$ | H | —O—(CH$_2$)$_3$— | 3.00 | α |
| I-2-a-6 | CH$_3$ | C$_2$H$_5$ | Br | H | —O—(CH$_2$)$_3$— | 3.44 | α |
| I-2-a-7 | CH$_3$ | C$_2$H$_5$ | Br | H | —O—(CH$_2$)$_3$— | 2.94 | β |
| I-2-a-8 | C$_2$H$_5$ | C$_2$H$_5$ | Cl | H | —O—(CH$_2$)$_3$— | 3.09 | β |
| I-2-a-9 | C$_2$H$_5$ | C$_2$H$_5$ | Cl | H | —O—(CH$_2$)$_3$— | 3.62 | α |
| I-2-a-10 | CH$_3$ | OCH$_3$ | CH$_3$ | H | —O—(CH$_2$)$_3$— | 2.28 | β |
| I-2-a-11 | CH$_3$ | OCH$_3$ | CH$_3$ | H | —O—(CH$_2$)$_3$— | 2.66 | α |
| I-2-a-12 | H | CH$_3$ | H | 3,4-Cl$_2$—Ph | —O—(CH$_2$)$_3$— | 3.74 | β |
| I-2-a-13 | H | CH$_3$ | H | 3,4-Cl$_2$—Ph | —O—(CH$_2$)$_3$— | 4.24 | α |
| I-2-a-14 | CH$_3$ | C$_2$H$_5$ | CH$_3$ | H | —O—(CH$_2$)$_3$— | 2.73 | β |
| I-2-a-15 | CH$_3$ | C$_2$H$_5$ | CH$_3$ | H | —O—(CH$_2$)$_3$— | 3.21 | α |
| I-2-a-16 | C$_2$H$_5$ | C$_2$H$_5$ | CH$_3$ | H | —O—(CH$_2$)$_3$— | 2.99 | β |
| I-2-a-17 | C$_2$H$_5$ | C$_2$H$_5$ | CH$_3$ | H | —O—(CH$_2$)$_3$— | 3.47 | α |
| I-2-a-18 | CH$_3$ | CH$_3$ | H | 4-Cl—Ph | —O—(CH$_2$)$_3$— | 3.52 | β |
| I-2-a-19 | CH$_3$ | CH$_3$ | H | 4-Cl—Ph | —O—(CH$_2$)$_3$— | 4.06 | α |
| I-2-a-20 | H | Cl | H | 4-Cl—Ph | —O—(CH$_2$)$_3$— | 3.25 | β |
| I-2-a-21 | H | Cl | H | 4-Cl—Ph | —O—(CH$_2$)$_3$— | 3.79 | α |
| I-2-a-22 | H | CH$_3$ | H | 4-F—Ph | —O—(CH$_2$)$_3$— | 3.0 | β |
| I-2-a-23 | H | CH$_3$ | H | 4-F—Ph | —O—(CH$_2$)$_3$— | 3.5 | α |
| I-2-a-24 | H | CH$_3$ | H | 4-Cl—Ph | —O—(CH$_2$)$_3$— | 3.32 | β |
| I-2-a-25 | H | CH$_3$ | H | 4-Cl—Ph | —O—(CH$_2$)$_3$— | 3.87 | α |
| I-2-a-26 | H | CH$_3$ | CH$_3$ | 4-Cl—Ph | —O—(CH$_2$)$_3$— | 4.15 | α |
| I-2-a-27 | H | CH$_3$ | CH$_3$ | 4-Cl—Ph | —O—(CH$_2$)$_3$— | 3.60 | β |
| I-2-a-28 | C$_2$H$_5$ | Br | CH$_3$ | H | —O—(CH$_2$)$_3$— | 2.73 | α |
| I-2-a-29 | C$_2$H$_5$ | CH$_3$ | Br | H | —O—(CH$_2$)$_3$— | 3.22 | α |
| I-2-a-30 | H | CH$_3$ | Br | CH$_3$ | —O—(CH$_2$)$_3$— | 3.28 | α |
| I-2-a-31 | H | CH$_3$ | Br | CH$_3$ | —O—(CH$_2$)$_3$— | 2.77 | β |
| I-2-a-32 | CH$_3$ | Br | CH$_3$ | H | —O—(CH$_2$)$_3$— | 2.48 | β |
| I-2-a-33 | CH$_3$ | Br | CH$_3$ | H | —O—(CH$_2$)$_3$— | 2.95 | α |
| I-2-a-34 | CH$_3$ | OCH$_3$ | H | H | —O—(CH$_2$)$_3$— | 2.05 | β |
| I-2-a-35 | CH$_3$ | OCH$_3$ | H | H | —O—(CH$_2$)$_3$— | 2.42 | α |
| I-2-a-36 | C$_2$H$_5$ | Cl | Br | H | —O—(CH$_2$)$_3$— | 2.77 | β |
| I-2-a-37 | C$_2$H$_5$ | Cl | Br | H | —O—(CH$_2$)$_3$— | 3.40 | α |
| I-2-a-38 | Cl | Br | C$_2$H$_5$ | H | —O—(CH$_2$)$_3$— | 2.79 | β |
| I-2-a-39 | Cl | Br | C$_2$H$_5$ | H | —O—(CH$_2$)$_3$— | 3.26 | α |
| I-2-a-40 | H | Cl | Cl | CH$_3$ | —O—(CH$_2$)$_3$— | 2.60 | β |
| I-2-a-41 | H | Cl | Cl | CH$_3$ | —O—(CH$_2$)$_3$— | 3.14 | α |
| I-2-a-42 | CH$_3$ | CH$_3$ | CH$_3$ | 4-Cl—Ph | —O—(CH$_2$)$_3$— | 3.79 | β |
| I-2-a-43 | CH$_3$ | CH$_3$ | CH$_3$ | 4-Cl—Ph | —O—(CH$_2$)$_3$— | 4.32 | α |
| I-2-a-44 | CH$_3$ | C$_2$H$_5$ | Cl | H | —O—(CH$_2$)$_3$— | 2.82 | β |
| I-2-a-45 | CH$_3$ | C$_2$H$_5$ | Cl | H | —O—(CH$_2$)$_3$— | 3.34 | α |
| I-2-a-46 | CH$_3$ | CH$_3$ | H | 4-F—Ph | —O—(CH$_2$)$_3$— | 3.69 | α |
| I-2-a-47 | CH$_3$ | CH$_3$ | H | 4-F—Ph | —O—(CH$_2$)$_3$— | 3.20 | β |

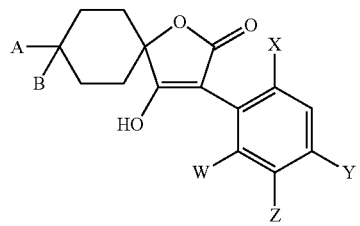

(I-2-a)

| Ex. No | W | X | Y | Z | A | B | log P* | Isomer |
|---|---|---|---|---|---|---|---|---|
| I-2-a-48 | H | $CH_3$ | $CH_3$ | $CH_3$ | —O—$(CH_2)_3$— | | 2.99 | α |
| I-2-a-49 | H | $CH_3$ | $CH_3$ | $CH_3$ | —O—$(CH_2)_3$— | | 2.54 | β |
| I-2-a-50 | H | Cl | H | 4-F—Ph | —O—$(CH_2)_3$— | | 2.91 | β |
| I-2-a-51 | H | Cl | H | 4-F—Ph | —O—$(CH_2)_3$— | | 3.42 | α |

Example I-2-b-1

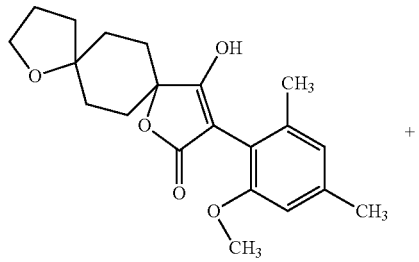

+

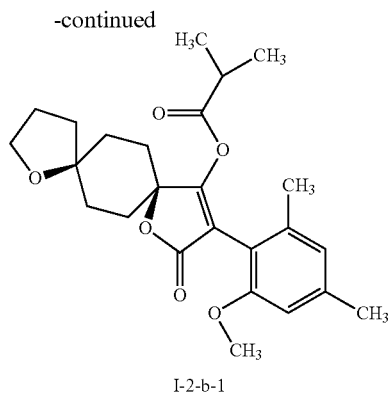

I-2-b-1

204 mg (0.569) mmol of a cis/trans mixture of the compounds (I-2-a-10) and (I-2-a-11) are dissolved in 10 ml of dichloromethane, 69 mg (0.683 mmol) of triethylamine are added and 73 mg (0.683 mmol) of isobutyryl chloride are added dropwise at room temperature. After 16 h of stirring at room temperature, the mixture is concentrated and purified by chromatography on silica gel (dichloromethane/acetone 100:10).

Yield: 51 mg of the cis isomer (I-2-b-1) (21% of theory)
log P: 4.12

Analogously to Example (I-2-b-1) and in accordance with the general statements on the preparation, the following compounds of the formula (I-2-b) are obtained:

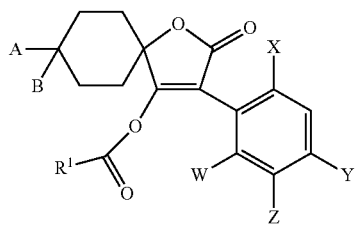

(I-2-b)

| Ex. No. | W | X | Y | Z | A | B | $R^1$ | log P* | Isomer |
|---|---|---|---|---|---|---|---|---|---|
| I-2-b-2 | $CH_3$ | $OCH_3$ | $CH_3$ | H | —O—$(CH_2)_3$— | | i-$C_3H_7$ | 4.60 | α |
| I-2-b-3 | H | $CH_3$ | $CH_3$ | 4-Cl—Ph | —O—$(CH_2)_3$— | | i-$C_3H_7$ | 5.64 | β |

-continued

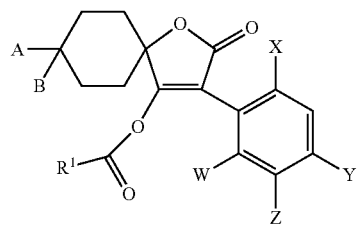
(I-2-b)

| Ex. No. | W | X | Y | Z | A | B | R¹ | log P* | Isomer |
|---|---|---|---|---|---|---|---|---|---|
| I-2-b-4 | H | $CH_3$ | $CH_3$ | 4-Cl—Ph | —O—$(CH_2)_3$— | | i-$C_3H_7$ | 6.24 | α |
| I-2-b-5 | H | $CH_3$ | H | $CH_3$ | —O—$(CH_2)_3$— | | i-$C_3H_7$ | 4.22 | β |
| I-2-b-6 | H | $CH_3$ | H | $CH_3$ | —O—$(CH_2)_3$— | | i-$C_3H_7$ | 4.78 | α |
| I-2-b-7 | $CH_3$ | $CH_3$ | $CH_3$ | H | —O—$(CH_2)_3$— | | i-$C_3H_7$ | 4.52 | β |
| I-2-b-8 | $CH_3$ | $CH_3$ | $CH_3$ | H | —O—$(CH_2)_3$— | | i-$C_3H_7$ | 5.12 | α |
| I-2-b-9 | H | $CH_3$ | H | 4-F—Ph | —O—$(CH_2)_3$— | | i-$C_3H_7$ | 4.83 | β |
| I-2-b-10 | H | $CH_3$ | H | 4-F—Ph | —O—$(CH_2)_3$— | | i-$C_3H_7$ | 5.38 | α |
| 1-2-b-11 | H | $CH_3$ | H | 4-Cl—Ph | —O—$(CH_2)_3$— | | i-$C_3H_7$ | 5.86 | α |
| I-2-b-12 | H | Cl | H | 4-Cl—Ph | —O—$(CH_2)_3$— | | i-$C_3H_7$ | 5.26 | β |
| I-2-b-13 | H | $CH_3$ | H | 4-Cl—Ph | —O—$(CH_2)_3$— | | i-$C_3H_7$ | 5.29 | β |
| I-2-b-14 | $CH_3$ | $CH_3$ | $CH_3$ | H | —O—$(CH_2)_3$— | | t-$C_4H_9$ | 4.96 | β |
| I-2-b-15 | $CH_3$ | $CH_3$ | H | 4-Cl—Ph | —O—$(CH_2)_3$— | | i-$C_3H_9$ | 5.63 | β |
| I-2-b-16 | $CH_3$ | $CH_3$ | H | 4-Cl—Ph | —O—$(CH_2)_3$— | | t-$C_4H_9$ | 6.09 | β |
| I-2-b-17 | $CH_3$ | $CH_3$ | $CH_3$ | H | —O—$(CH_2)_3$— | | t-$C_4H_9$ | 5.58 | α |
| I-2-b-18 | $CH_3$ | $OCH_3$ | H | H | —O—$(CH_2)_3$— | | i-$C_3H_7$ | 3.75 | β |
| I-2-b-19 | $CH_3$ | $OCH_3$ | H | H | —O—$(CH_2)_3$— | | t-$C_4H_9$ | 4.16 | β |
| I-2-b-20 | $CH_3$ | $OCH_3$ | H | H | —O—$(CH_2)_3$— | | i-$C_3H_7$ | 4.25 | α |
| I-2-b-21 | $CH_3$ | $OCH_3$ | $CH_3$ | H | —O—$(CH_2)_3$— | | t-$C_4H_9$ | 4.50 | β |
| I-2-b-22 | $C_2H_5$ | $C_2H_5$ | $CH_3$ | H | —O—$(CH_2)_3$— | | i-$C_3H_7$ | 5.17 | β |
| I-2-b-23 | $C_2H_5$ | $C_2H_5$ | $CH_3$ | H | —O—$(CH_2)_3$— | | t-$C_4H_9$ | 5.62 | β |
| I-2-b-24 | $C_2H_5$ | $C_2H_5$ | $CH_3$ | H | —O—$(CH_2)_3$— | | i-$C_3H_7$ | 5.79 | α |
| I-2-b-25 | $C_2H_5$ | $C_2H_5$ | $CH_3$ | H | —O—$(CH_2)_3$— | | t-$C_4H_9$ | 6.25 | α |

Example I-2-c-1

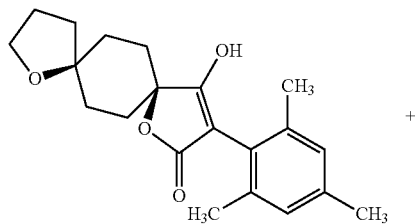

+

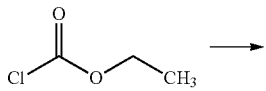

→

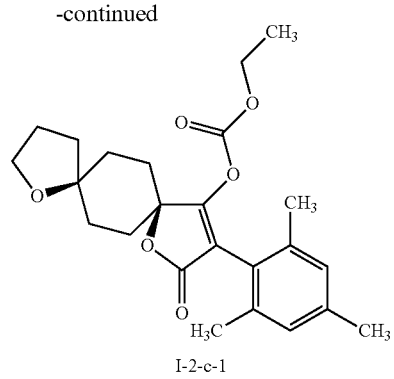

I-2-c-1

100 mg (0.292 mmol) of the compound according to Example (I-2-a-4) are dissolved in 5 ml of dichloromethane, 35 mg (0.350 mmol) of triethylamine are added and 38 mg (0.350 mmol) of ethyl chloroformate are added dropwise at room temperature. After 16 h of stirring at room temperature, the mixture is concentrated and purified by prep. HPLC on RP-18 silica gel (acetonitrile/water).

Yield: 64 mg (I-2-c-1) (53% of theory)

log P: 4.09

Analogously to Example (I-2-c-1) and in accordance with the general statements on the preparation, the following compounds of the formula (I-2-c) are obtained:

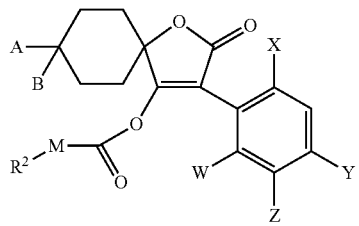

(I-2-c)

| Ex. No. | W | X | Y | Z | A | B | M | R² | log P* | Isomer |
|---|---|---|---|---|---|---|---|---|---|---|
| I-2-c-2 | CH₃ | CH₃ | CH₃ | H | —O—(CH₂)₃— | | O | C₂H₅ | 4.69 | α |
| I-2-c-3 | C₂H₅ | C₂H₅ | CH₃ | H | —O—(CH₂)₃— | | O | C₂H₅ | 4.68 | β |
| I-2-c-4 | C₂H₅ | C₂H₅ | CH₃ | H | —O—(CH₂)₃— | | O | C₂H₅ | 5.28 | α |

Example III-1

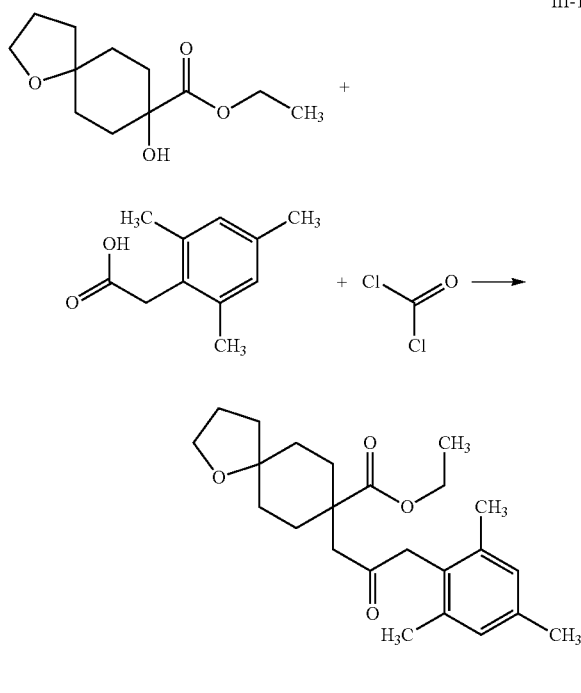

III-1

178 mg (1.0 mmol) of 2,4,6-trimethylphenylacetic acid are initially charged in 10 ml of toluene, 238 mg (2.0 mmol) of thionyl chloride and 1 drop of DMF are added, the mixture is stirred at 90° C. for 1 h, cooled and concentrated using a rotary evaporator, the residue is dissolved in 5 ml of toluene, 228 mg (1.0 mmol) of the hydroxy ester according to Ex, XXII-1 are added and the mixture is stirred at 90° C. for 8 h, cooled and concentrated using a rotary evaporator. The crude product is purified by partitioning between 5% strength aqueous sodium hydroxide solution and MTB ether. The org. phase is dried and concentrated.

Yield: 280 mg of an oil (72% of theory)

DMF=N,N-dimethylformamide

The oil is used without further purification for the synthesis of Ex. I-2-a-1.

Example XVI-1

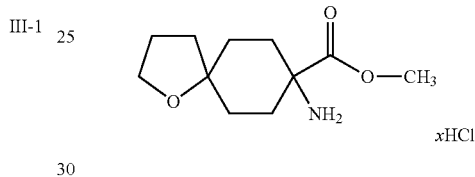

Under argon, 35 g of the compound according to Ex. XIX-1 are initially charged in 880 ml of methanol at from 0 to 5° C. 15.2 ml of thionyl chloride are added dropwise and the mixture is stirred at 0° C. for 30 minutes and at 40° C. for 8 h until a clear solution is formed. The solution is then cooled to 5° C. and the precipitate is filtered off with suction. The solution is concentrated using a rotary evaporator.

Yield: 31 g (84% of theory)

¹H-NMR (400 MHz, d₆-DMSO): δ=1.52-1.68 (m, 5H, C$\underline{H}_2$), 1.81-2.00 (m, 6H, C$\underline{H}_2$), 2.07-2.14 (m, 1H, C$\underline{H}_2$), 3.68-3.72 (m, 2H, OC$\underline{H}_2$), 3.74 (s, 3H, OC$\underline{H}_3$) ppm.

Example XIX-1

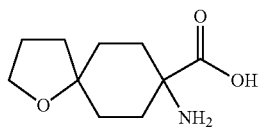

Under argon, 33.3 g of the compound according to Example XXIII-1 are suspended in 167 ml of 30% strength KOH, and the mixture is stirred at reflux overnight.

The mixture is concentrated to about 25% of its volume using a rotary evaporator; at 0-10° C., the pH is adjusted to 2 using concentrated HCl. The solution is concentrated using a rotary evaporator and dried. The residue is directly employed for the esterification to give XVI-1.

Example XXIII-1

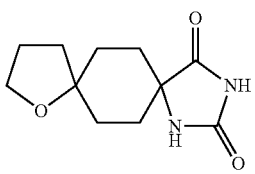 [SMILES: O=C1NC(=O)C2(CCC3(CCCO3)CC2)N1]

Ammonium carbonate (65 g) and sodium cyanide (8.7 g) are initially charged in 290 ml of water. Starting at room temperature, 25 g of 1-oxaspiro-[4,5]-decan-8-one (known from DE 3241933 A1, U.S. Pat. No. 4,438,130 A, WO 92/06094, WO 94/11374) are added dropwise, and the reaction mixture is stirred at from 55° C. to 60° C. for four hours, concentrated to 50 ml, then stirred at from 0° to 5° C. for two hours and filtered off with suction at about −2° C., and the residue is washed with a little ice-water and dried.

Yield: 33.3 g (91% of theory), $^1$H-NMR (400 MHz, $d_6$-DMSO): δ=1.36-1.39 (dm, 1H, CH$_2$), 1.58-1.72 (m, 8H, CH$_2$), 1.81-1.87 (m, 2H, CH$_2$), 1.88-2.02 (m, 1H, CH$_2$), 3.69-3.72 (t, 2H, OCH$_2$), 8.04, 8.19 (2s, 1H, NH—C), 10.31 (s, 1H, CO—NH—CO) ppm.

Synthesis of ethyl 8-hydroxy-1-oxaspiro[4,5]decane-8-carboxylate (XXII-1)

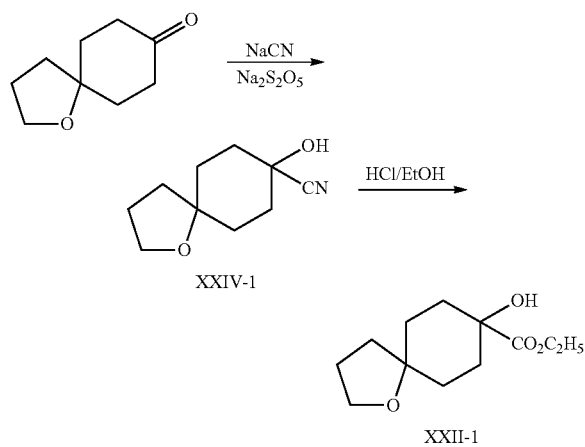

Example XXIV-1

35 g (713 mmol) of sodium cyanide are dissolved in 400 ml of water, 100 g (648 mmol) of 1-oxa-spiro-[4,5]-decan-8-one are added dropwise at 20-28° C. over a period of 30 min, followed by a solution of 80 g Na$_2$S$_2$O$_5$ (421 mmol), and the mixture is stirred at room temperature overnight.

For work-up, the mixture is extracted 3 times with in each case 300 ml of toluene and the org. phase is concentrated using a rotary evaporator.

Yield: 107 g of the cyanohydrin (91% of theory) (XXIV-1)

Example XXII-1

107 g (236 mmol) of the cyanohydrin (XXIV) from step 1 are dissolved in 400 ml of ethanol, hydrogen chloride is introduced at −20° C. over a period of 5 hours (the mixture slowly warms to −5° C.) and the mixture is stirred at room temperature overnight.

For work-up, the solvent is distilled off under reduced pressure at at most 45° C., 400 ml of ice-water are added and the mixture is stirred for 3 hours. The mixture is extracted 3 times with in each case 300 ml of dichloromethane and the org. phase is washed with sodium bicarbonate solution, concentrated using a rotary evaporator and disilled under high vacuum (b.p. 116° C. at 0.08 mbar).

Yield: 55.7 g of the hydroxy ester (41% of theory) (XXII-1)

Preparation of 1-oxaspiro-[4,5]-decan-8-one (E)

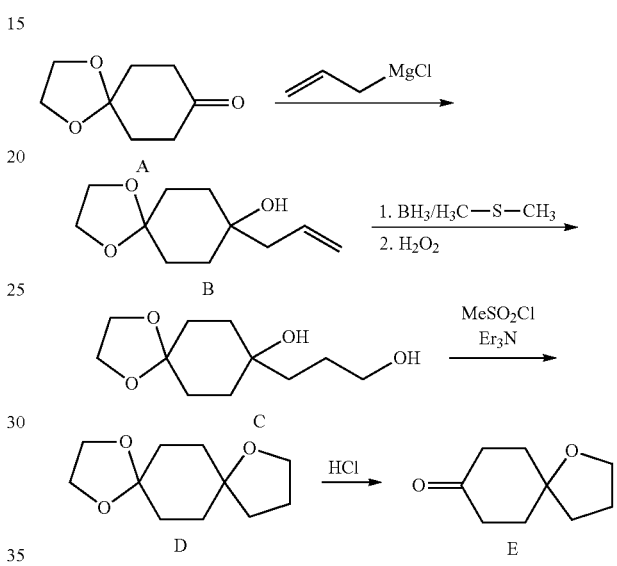

Preparation of B:

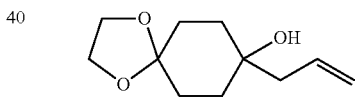

At room temperature, 1.8 ml (3.6 mol) of allylmagnesium chloride (2M in THF) are initially charged. A solution of 467 g (3 mol) of 1,4-cyclohexanedione monoethylene ketal in 3000 ml of THF is added dropwise. After the addition, the reaction mixture is briefly heated under reflux and then cooled to 0° C. About 300 ml of water are carefully added dropwise, Celite is then added and the mixture is stirred for one hour. The reaction mixture is then filtered through Celite on a nutscht filter, and the filtrate is concentrated using a rotary evaporator. For purification, the product is distilled under oilpump vacuum without cooling the bridge. The head temperature was 81-83° C.

Yield: 485 g (=81% of theory)
Preparation of C:

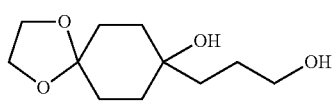 [SMILES: OCCCC1(O)CCC2(CC1)OCCO2]

At 0° C., 225.4 g (2.94 mol) of borane/dimethyl sulphide complex are added dropwise to a solution of 485.1 g (2.45 mol) of the compound B in 3675 ml of THF. The reaction mixture is then stirred at room temperature overnight. At 0° C., 1225 ml of water, 980 ml of 3M NaOH and 980 ml of hydrogen peroxide (30% strength in water) are then successively added dropwise to the reaction mixture. The aqueous phase is extracted three times with methyl tert-butyl ether (MTBE), and the combined organic phases are dried over sodium sulphate. The drying agent is separated off, the solvent is then removed and the product is reacted without further purification.

Yield: 275 g (=52% of theory)

Preparation of D:

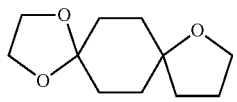 [SMILES: C1COC2(C1)CCC1(CC2)OCCO1]

At 0° C., a solution of 274.3 g (1.27 mol) of the compound C and 294.6 g (2.92 mol) of triethylamine in 3175 ml of dichloromethane is initially charged. 160 g (1.4 mol) of methanesulphonyl chloride in 1270 ml of dichloromethane are slowly added dropwise to the solution. After the addition has ended, the mixture is stirred overnight. The organic phase is washed once with water, once with potassium carbonate solution and once with dilute HCl and then dried over sodium sulphate. The drying agent is separated off, the solvent is then removed and the product is, for purification, distilled under oilpump vacuum at a head temperature of 68-72° C.

Yield: 101 g (=40% of theory)

Preparation of E:

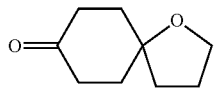

At 80° C., 101 g (0.51 mol) of compound D in 408 ml of THF are stirred in 428 ml of dilute HCl (326 ml of water and 102 ml of concentrated HCl) overnight. The progess of the reaction is monitored, and once no more starting material is detected, the solvent of the reaction mixture is distilled off and the mixture is then extracted three times with chloroform. The combined organic phases are dried over sodium sulphate. The drying agent is separated off, the solvent is then removed and the product is, for purification, distilled under oilpump vacuum at a head temperature of 56-58° C.

Yield: 56 g (=71% of theory)

Determination of the logP Values

The logP values given in the table were determined in accordance with EEC Directive 79/831 Annex V.A8 by HPLC (high performance liquid chromatography) on a reverse-phase column (C 18). Temperature: 55° C.

Mobile phases for the determination in the acidic range (pH 3.4):

Mobile phase A: acetonitrile+1 ml of formic acid/liter.
Mobile phase B: water+0.9 ml of formic acid/liter.

Gradient: from 10% mobile phase A/90% mobile phase B to 95% mobile phase A/5% mobile phase B over 4.25 min.

Calibration was carried out using unbranched alkan-2-ones (having 3 to 16 carbon atoms) with known logP values (determination of the logP values by the retention times using linear interpolation between two successive alkanones). The lambda max values were determined in the maxima of the chromatographic signals using the UV spectra from 200 nm to 400 nm.

USE EXAMPLES

Example 1

1. Herbicidal Pre-Emergence Action

Seeds of monocotyledonous and dicotyledonous weed and crop plants are placed in sandy loam in wood fibre pots and covered with soil. The test compounds, formulated in the form of wettable powders (WP) or emulsion concentrates (EC), are then, as an aqueous suspension or emulsion with a water application rate of 600 l/ha (converted), with 0.2% of wetting agent added, applied at various dosages to the surface of the covering soil. After the treatment, the pots are placed in a greenhouse and kep under good growth conditions for the test plants. The visual assessment of the damage to the test plants is carried out after a trial period of 3 weeks by comparison with untreated controls (herbicidal activity in percent (%): 100% activity=the plants have died, 0% activity=like control plants).

Applied by the pre-emergence method at 320 g/ha of a.i., the following compounds show an activity of ≥80% against *Echinocloa crus-galli, Lolium multiflorum* and *Setaria viridis* Ex. I-1-a-2, I-1-a-4, I-1-a-8, I-1-a-10, I-1-a-11, I-1-a-12, I-1-a-13, I-1-a-40, I-1-a-49, I-1-a-51, I-1-a-54, I-1-a-55, I-1-b-1, I-1-b-5, I-1-b-7, I-2-b-1, I-2-b-2, I-1-c-1, I-1-c-11, I-1-c-12, I-1-c-13, I-1-c-15, I-1-c-16, I-1-c-18, I-1-c-19

2. Herbicidal Post-Emergence Action

Seeds of monocotyledonous and dicotyledonous weed and crop plants are placed in sandy loam in wood fibre pots, covered with soil and cultivated in a greenhouse under good growth conditions. 2 to 3 weeks after sowing, the test plants are treated at the one-leaf stage. The test compounds, formulated as wettable powders (WP) or emulsion concentrates (EC), are then, with a water application rate of 600 l/ha (converted), with 0.2% of wetting agent added, sprayed at various dosages onto the green parts of the plants. After the test plants have been kept in the greenhouse under optimum growth conditions for about 3 weeks, the activity of the preparations is rated visually in comparison to untreated controls (herbicidal activity in percent (%): 100% activity=the plants have died, 0% activity=like control plants).

Applied by the post-emergence method at 80 g/ha of a.i., the following compounds show an activity of ≥80% against *Alopecurus myosuroides, Echinochloa crus-galli, Lolium multiflorum* and *Setaria viridis*: Ex. I-1-a-10, I-1-a-11, I-1-a-12, I-1-a-49, I-1-a-51

Applied by the post-emergence method at 80 g/ha of a.i., the following compounds show an activity of ≥% against *Alopecurus myosuroides, Echinochloa crus-galli, Lolium multiflorum* and *Setaria viridis*: I-1-a-4, I-1-a-54, I-1-a-58, I-1-c-10, I-1-c-11, I-1-c-12, I-1-c-13, I-1-c-14

Example 2

1. Herbicidal Post-Emergence Action

Seeds of monocotyledonous and dicotyledonous weed and crop plants are placed in sandy loam in wood fibre pots or in plastic pots, covered with soil and cultivated in a greenhouse, during the vegetation period also outdoors outside of the greenhouse, under good growth conditions. 2 to 3 weeks after sowing, the test plants are treated at one- to three-leaf stage. The test compounds, formulated as wettable powders (WP) or liquid (EC) are, at a water application rate of 300 l/ha (converted), with wetting agent (0.2 to 0.3%) added, sprayed at various dosages onto the plants and the surface of the soil. 3 to 4 weeks after treatment of the test plants, the effect of the preparations is rated visually in comparison to untreated controls (herbicidal activity in percent: 100% activity=the plants have died, 0% activity=like control plants).

Use of Safeners:

If it is additionally to be tested as to whether safeners can improve the plant compatibility of test substances in the case of crop plants, the following options are used for applying the safeners:

seeds of the crop plants are, before sowing, dressed with the safener substance (the amount of safener stated in percent, based on the weight of the seed)

before application of the test substances, the crop plants are sprayed with the safener at a certain application rate per hectare (usually 1 day before the application of the test substances)

the safener is applied together with the test substance as a tank mix (the amount of safener stated in g/ha or as a ratio, based on the herbicide).

Container trials with cereal in a greenhouse mefenpyr 1 day prior to herbicide application

|  | Application rate g of a.i./ha | 28 days after application Summer wheat observed (%) |
|---|---|---|
| Ex. I-1-a-11 | 100 | 95 |
|  | 50 | 80 |
|  | 25 | 70 |
|  | 12.5 | 65 |
| Ex. I-1-a-11 + mefenpyr | 100 + 50 | 80 |
|  | 50 + 50 | 40 |
|  | 25 + 50 | 30 |
|  | 12.5 + 50 | 10 |

|  | Application rate g of a.i./ha | 10 days after application Summer barley observed (%) |
|---|---|---|
| Ex. I-1-a-13 | 50 | 30 |
|  | 25 | 20 |
|  | 12.5 | 20 |
| Ex. I-1-a-13 + mefenpyr | 50 + 50 | 10 |
|  | 25 + 50 | 2 |
|  | 12.5 + 50 | 0 |

|  | Application rate g of a.i./ha | 28 days after application Summer wheat observed (%) |
|---|---|---|
| Ex. I-1-a-13 | 100 | 50 |
|  | 50 | 30 |
|  | 25 | 10 |
| Ex. I-1-a-13 + mefenpyr | 100 + 50 | 30 |
|  | 50 + 50 | 10 |
|  | 25 + 50 | 5 |

|  | Application rate g of a.i./ha | 28 days after application Summer wheat observed (%) |
|---|---|---|
| Ex. I-1-b-7 | 100 | 60 |
|  | 50 | 50 |
|  | 25 | 10 |
| Ex. I-1-b-7 + mefenpyr | 100 + 50 | 5 |
|  | 50 + 50 | 5 |
|  | 25 + 50 | 2 |

Example 3

Phaedon Test (PHAECO Spray Treatment)

Solvents:

78.0 parts by weight of acetone 1.5 parts by weight of dimethylformamide

Emulsifier: 0.5 parts by weight of alkylaryl polyglycol ether

To produce a suitable preparation of active compound, 1 part by weight of active compound is mixed with the stated amounts of solvents and emulsifier, and the concentrate is diluted with emulsifier-containing water to the desired concentration.

Discs of chinese cabbage (*Brassica pekinensis*) are sprayed with an active compound preparation of the desired concentration and, after drying, populated with larvae of the mustard beetle (*Phaedon cochleariae*).

After the desired period of time, the effect in % is determined. 100% means that all beetle larvae have been killed; 0% means that none of the beetle larvae have been killed.

In this test, for example, the following compounds of the Preparation Examples show, at an application rate of 500 g/ha, an efficacy of ≥80%:

Ex. No. I-1-a-3, I-1-a-4, I-1-a-5, I-1-a-6, I-1-a-13, I-1-a-18, I-1-a-23, I-1-a-41, I-1-a-43, I-1-a-44, I-1-a-45, I-1-a-46, I-1-a-48, I-1-a-49, I-1-a-51, I-1-a-54, I-1-a-56, I-1-a-58, I-1-b-1, I-1-b-7, I-1-c-1, I-1-c-12, I-1-c-15, I-1-c-21, I-2-a-3, I-2-a-4, I-2-a-14, I-2-a-18, I-2-a-21, I-2-a-22, I-2-a-23, I-2-a-24, I-2-a-25, I-2-a-32, I-2-a-42, I-2-a-44, I-2-a-47, I-2-a-49, I-2-b-1, I-2-b-5, I-2-b-7, I-2-b-15, I-2-b-21, I-2-c-1, I-2-c-2

Example 4

*Spodoptera frugiperda* Test (Spray Treatment)

Solvents: 78.0 parts by weight of acetone 1.5 parts by weight of dimethylformamide Emulsifier: 0.5 part by weight of alkylaryl polyglycol ether To produce a suitable preparation of active compound, 1 part by weight of active compound is mixed with the stated amounts of solvents and emulsifier, and the concentrate is diluted with emulsifier-containing water to the desired concentration.

Discs of maize leaves (*Zea mays*) are sprayed with an active compound preparation of the desired concentration and, after drying, populated with caterpillars of the army worm (*Spodoptera frugiperda*).

After the desired period of time, the effect in % is determined. 100% means that all caterpillars have been killed; 0% means that none of the caterpillars have been killed.

In this test, for example, the following compounds of the Preparation Examples show, at an application rate of 500 g/ha, an efficacy of ≥80%:

Ex. No. I-1-a-1, I-1-a-2, I-1-a-3, I-1-a-4, I-1-a-34, I-1-a-36, I-1-a-43, I-1-a-58, I-1-b-7, I-1-c-1, I-1-c-2, I-1-c-3, I-1-c-4, I-2-a-4, I-2-a-18, I-2-a-32, I-2-b-15, I-2-b-16

Example 5

Tetranychus Test, OP Resistent (TETRUR Spray Treatment)

Solvents: 78.0 parts by weight of acetone
1.5 parts by weight of dimethylformamide
Emulsifier: 0.5 part by weight of alkylaryl polyglycol ether
To produce a suitable preparation of active compound, 1 part by weight of active compound is mixed with the stated amounts of solvents and emulsifier, and the concentrate is diluted with emulsifier-containing water to the desired concentration.

Discs of bean leaves (*Phaseolus vulgaris*) which are infested by all stages of the greenhouse red spidermite (*Tetranychus urticae*) are sprayed with an active compound preparation of the desired concentration.

After the desired period of time, the effect in % is determined. 100% means that all spidermites have been killed; 0% means that none of the spidermites have been killed.

In this test, for example, the following compounds of the Preparation Examples show, at an application rate of 100 g/ha, an efficacy of ≥80%:

Ex. No. I-1-a-1, I-1-a-2, I-1-a-3, I-1-a-4, I-1-a-11, I-1-a-13, I-1-a-20, I-1-a-27, I-1-a-40, I-1-a-41, I-1-a-44, I-1-a-46, I-1-b-1, I-1-b-3, I-1-b-6, I-1-b-7, I-1-c-2, I-1-c-21, I-2-a-1, I-2-a-4, I-2-a-5, I-2-a-6, I-2-a-10, I-2-a-12, I-2-a-16, I-2-a-18, I-2-a-20, I-2-a-21, I-2-a-23, I-2-a-24, I-2-a-25, I-2-a-26, I-2-a-42, I-2-a-43, I-2-a-47, I-2-a-51, I-2-b-2, I-2-b-5, I-2-b-8, I-2-b-11, I-2-b-14, I-2-b-15, I-2-b-16, I-2-b-22, I-2-b-23, I-2-b-24, I-2-b-25, I-2-c-1, I-2-c-2, I-2-c-3, I-2-c-4

In this test, for example, the following compounds of the Preparation Examples show, at an application rate of 500 g/ha, an efficacy of ≥80%:

Ex. No. I-1-a-9, I-1-a-10, I-1-c-2, I-1-c-3, I-1-c-4, I-2-a-50

Example 6

Myzus Test (MYZUPE Spray Treatment)

Solvents:
78.0 parts by weight of acetone
1.5 parts by weight of dimethylformamide
Emulsifier: 0.5 parts by weight of alkylaryl polyglycol ether
To produce a suitable preparation of active compound, 1 part by weight of active compound is mixed with the stated amounts of solvents and emulsifier, and the concentrate is diluted with emulsifier-containing water to the desired concentration.

Discs of chinese cabbage (*Brassica pekinensis*) which are infested by all stages of the green peach aphid (*Myzus persicae*) are sprayed with an active compound preparation of the desired concentration.

After the desired period of time, the effect in % is determined. 100% means that all aphids have been killed; 0% means that none of the aphids have been killed.

In this test, for example, the following compounds of the Preparation Examples show, at an application rate of 500 g/ha, an efficacy of ≥80%:

Ex. No. I-1-a-1, I-1-a-2, I-1-a-3, I-1-a-4, I-1-a-5, I-1-a-6, I-1-a-7, I-1-a-8, I-1-a-9, I-1-a-5, I-1-a-6, I-1-a-9, I-1-a-10, I-1-a-11, I-1-a-12, I-1-a-13, I-1-a-14, I-1-a-15, I-1-a-16, I-1-a-17, I-1-a-18, I-1-a-19, I-1-a-20, I-1-a-21, I-1-a-22, I-1-a-23, I-1-a-24, I-1-25, I-1-a-26, I-1-a-27, I-1-a-28, I-1-a-29, I-1-a-31, I-1-a-32, I-1-a-33, I-1-a-34, I-1-a-35, I-1-a-36, I-1-a-37, I-1-a-38, I-1-a-39, I-1-a-40, I-1-a-41, I-1-a-42, I-1-a-43, I-1-a-44, I-1-a-45, I-1-a-46, I-1-a-47, I-1-a-48, I-1-a-49, I-1-a-50, I-1-a-51, I-1-a-52, I-1-a-54, I-1-a-55, I-1-a-56, I-1-a-57, I-1-a-58, I-1-b-1, I-1-b-2, I-1-b-3, I-1-b-4, I-1-b-5, I-1-b-6, I-1-b-7, I-1-c-1, I-1-c-2, I-1-c-3, I-1-c-4, I-1-c-5, I-1-c-6, I-1-c-7, I-1-c-8, I-1-c-9, I-1-c-10, I-1-c-11, I-1-c-12, I-1-c-13, I-1-14, I-1-c-15, I-1-c-16, I-1-c-18, I-1-c-21, I-1-b-2, I-2-a-1, I-2-a-2, I-2-a-3, I-2-a-4, I-2-a-5, I-2-a-6, I-2-a-7, I-2-a-8, I-2-a-10, I-2-a-11, I-2-a-12, I-2-a-13, I-2-a-14, I-2-a-15, I-2-a-16, I-2-a-17, I-2-a-18, I-2-a-19, I-2-a-20, I-2-a-21, I-2-a-22, I-2-a-23, I-2-a-24, I-2-a-25, I-2-a-26, I-2-a-27, I-2-a-28, I-2-a-29, I-2-a-30, I-2-a-31, I-2-a-32, I-2-a-33, I-2-a-34, I-2-a-35, I-2-a-36, I-2-a-38, I-2-a-39, I-2-a-40, I-2-a-41, I-2-a-42, I-2-a-43, I-2-a-44, I-2-a-45, I-2-a-46, I-2-a-47, I-2-a-48, I-2-a-49, I-2-a-50, I-2-a-51, I-2-b-1, I-2-b-2, I-2-b-5, I-2-b-6, I-2-b-7, I-2-b-8, I-2-b-9, I-2-b-10, I-2-b-12, I-2-b-13, I-2-b-14, I-2-b-15, I-2-b-16, I-2-b-17, I-2-b-18, I-2-b-19, I-2-b-22, I-2-b-23, I-2-b-24, I-2-c-1, I-2-c-3, I-2-c-4

Example 7

Meloidogyne Test (MELGIN Spray Treatment)

Solvents: 80 parts by weight of acetone
To produce a suitable preparation of active compound, 1 part by weight of active compound is mixed with the stated amount of solvent, and the concentrate is diluted with water to the desired concentration Containers are filled with sand, solution of active compound, *Meloidogyne incognita* egg larvae suspension and lettuce seeds. The lettuce seeds germinate and the plants develop. On the roots, galls are formed.

After the desired period of time, the nematicidal activity is determined in % by the formation of galls. 100% means that no galls were found; 0% means that the number of galls on the treated plants corresponds to that of the untreated control.

In this test, for example, the following compounds of the Preparation Examples show, at an application rate of 500 g/ha, an efficacy of ≥80%:

Ex. No. I-2-a-4, I-2-a-5, I-2-b-9, I-2-a-11

Example 8

*Boophilus microplus* Test (BOOPMI Injection)

Solvent: dimethyl sulphoxide
To produce a suitable preparation of active compound, 1 part by weight of active compound is mixed with the stated amount of solvent, and the concentrate is diluted with water to the desired concentration The solution of active compound is injected into the abdomen (*Boophilus microplus*), the animals are transferred into dishes and kept in a climatized room. The activity is checked by examination for deposition of fertile eggs.

After the desired period of time, the activity in % is determined. 100% means that none of the ticks has laid fertile eggs.

In this test, for example, the following compounds of the Preparation Examples show, at an application rate of 20 μg/animal, an efficacy of ≥80%:

Ex. No. I-1-a-3, I-1-a-4, I-1-a-5, I-1-a-6, I-1-b-1, I-2-a-1

Example 9

*Lucilia cuprina* Test (LUCICU)

Solvent: Dimethyl sulphoxide
To produce a suitable preparation of active compound, 1 part by weight of active compound is mixed with the stated amount of solvent, and the concentrate is diluted with water to the desired concentration

*Lucilia cuprina* larvae are placed into containers containing horse meat treated with the preparation of active compound of the desired concentration.

After the desired period of time, the kill in % is determined. 100% means that all larvae have been killed; 0% means that none of the larvae have been killed.

In this test, for example, the following compounds of the Preparation Examples show, at an appliction rate of 100 ppm, an efficacy of ≥80%:

Ex. No. I-1-a-3, I-1-a-4, I-1-a-5, I-1-a-6, I-1-a-7, I-1-a-8, I-1-b-1, I-1-c-2, I-1-c-3, I-1-c-4, I-2-a-1

Example 10

*Myzus persicae* Test (MYZUPE)

Solvent: 7 parts by weight of dimethylformamide
Emulsifier: 2 parts by weight of alkylaryl polyglycol ether To produce a suitable preparation of active compound, 1 part by weight of active compound is mixed with the stated amounts of solvents and emulsifier, and the concentrate is diluted with emulsifier-containing water to the desired concentration. For the required application of ammonium salts, penetrants or ammonium salts and penetrants, these are in each case added with a pipette after dilution of the respective finished solution of the preparation at a concentration of 1000 ppm.

Paprika plants (*Capsicum annuum*) which are heavily infested by the green peach aphid (*Myzus persicaei*) are treated by being sprayed with the preparation of active compound of the desired concentration.

After the desired period of time, the kill in % is determined. 100% means that all animals have been killed; 0% means that none of the animals have been killed.

In this test, for example, the following compounds of the Preparation Examples show good efficacy: see table

| Activity increase by addition of RME and RME + AMS | | % efficacy after 6 days | | | |
|---|---|---|---|---|---|
| Active compound | | ppm | without additive | +AMS | +RME | +RME + AMS |
| Ex. I-1-a-8 | MYZUPE | 4 | 45 | 98 | 99 | 100 |
|  |  | 0.8 | 0 | 0 | 20 | 99 |
| Ex. I-1-a-4 | MYZUPE | 4 | 75 | 80 | 90 | 98 |
|  |  | 0.8 | 10 | 0 | 60 | 99 |

Example 11

*Aphis gossypii* Test (APHIGO)

Solvents: 7 parts by weight of dimethylformamide
Emulsifier: 2 parts by weight of alkylaryl polyglycol ether To produce a suitable preparation of active compound, 1 part by weight of active compound is mixed with the stated amounts of solvents and emulsifier, and the concentrate is diluted with emulsifier-containing water to the desired concentration. For the required application of ammonium salts, penetrants or ammonium salts and penetrants, these are in each case added with a pipette after dilution of the respective finished solution of the preparation at a concentration of 1000 ppm.

Cotton leaves (*Gossypium hirsutum*) which are heavily infested by the cotton aphid (*Aphis gossypii*) are sprayed with an active compound preparation of the desired concentration.

After the desired period of time, the kill in % is determined. 100% means that all aphids have been killed; 0% means that none of the aphids have been killed.

In this test, for example, the following compounds of the Preparation Examples show good efficacy: see table

| Activity increase by addition of RME and RME + AMS | | % efficacy after 6 days | | | |
|---|---|---|---|---|---|
| Active compound | | ppm | without additive | +AMS | +RME | +RME + AMS |
| Ex. I-1-a-4 | APHIGO | 4 | 60 | 75 | 75 | 80 |
|  |  | 0.8 | 10 | 0 | 15 | 45 |
| Ex. I-1-a-6 | APHIGO | 20 | 35 | 5 | 60 | 95 |

RME = rapeseed oil methyl ester
AMS = ammonium sulphate

Example 12

*Heliothis virescens* Test—Treatment of Transgenic Plants

Solvent: 7 parts by weight of acetone
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Soybean shoots (*Glycine max*) of the cultivar Roundup Ready (trademark of Monsanto Comp. USA) are treated by being dipped into the preparation of active compound of the desired concentration and are populated with the tobacco budworm Heliothis virescens while the leaves are still moist.

After the desired period of time, the kill of the insects is determined.

Example 13

Critical Concentration Test/Soil Insects—Treatment of Transgenic Plants

Test insect: *Diabrotica balteata*—larvae in the soil
Solvent: 7 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is poured onto the soil. Here, the concentration of active compound in the preparation is virtually immaterial; only the amount by weight of active compound per volume unit of soil, which is stated in ppm (mg/l), matters. The soil is filled into 0.25 l pots, and these are allowed to stand at 20° C.

Immediately after the preparation, 5 pregerminated maize corns of the cultivar YIELD GUARD (trademark of Monsanto Comp., USA) are placed into each pot. After 2 days, the appropriate test insects are placed into the treated soil. After a further 7 days, the efficacy of the active compound is determined by counting the maize plants that have emerged (1 plant=20% activity).

The invention claimed is:

1. A compound of the formula (I), an α isomer, a β isomer or a mixture thereof,

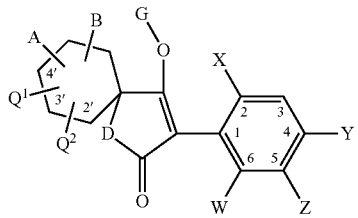

in which
W represents hydrogen, alkyl, alkenyl, alkynyl, optionally substituted cycloalkyl, halogen, alkoxy, alkenyloxy, haloalkyl, haloalkoxy or cyano,
X represents halogen, alkyl, alkenyl, alkynyl, optionally substituted cycloalkyl, alkoxy, alkenyloxy, alkylthio, alkylsulphinyl, alkylsulphonyl, haloalkyl, haloalkoxy, haloalkenyloxy, nitro or cyano,
Y and Z independently of one another represent hydrogen, alkyl, alkenyl, alkynyl, optionally substituted cycloalkyl, alkoxy, halogen, haloalkyl, haloalkoxy, cyano, nitro or in each case optionally substituted aryl or hetaryl,
A and B and the carbon atom (4'-position) to which they are attached represent a tetrahydrofuran ring

wherein "*" indicates the carbon atom at 4'-position,
which is optionally substituted by alkyl, haloalkyl, alkoxy, alkoxyalkyl or optionally substituted phenyl,
D represents NH or oxygen,
$Q^1$, $Q^2$ independently of one another represent hydrogen, alkyl, haloalkyl or alkoxy,
G represents hydrogen (a) or represents one of the groups (b)

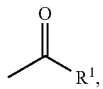

(c)

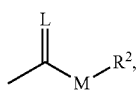

(d)

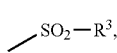

(e)

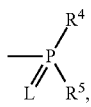

(f)

E, or (g)

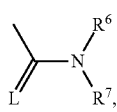

in which
E represents a metal ion or an ammonium ion,
L represents oxygen or sulphur,
M represents oxygen or sulphur,
$R^1$ represents in each case optionally halogen- or cyano-substituted alkyl, alkenyl, alkoxyalkyl, alkylthioalkyl or polyalkoxyalkyl or represents in each case optionally halogen-, alkyl- or alkoxy-substituted cycloalkyl or heterocyclyl or represents in each case optionally substituted phenyl, phenylalkyl, hetaryl, phenoxyalkyl or hetaryl-oxyalkyl,
$R^2$ represents in each case optionally halogen- or cyano-substituted alkyl, alkenyl, alkoxyalkyl or polyalkoxyalkyl or represents in each case optionally substituted cycloalkyl, phenyl or benzyl,
$R^3$, $R^4$ and $R^5$ independently of one another represent in each case optionally halogen-substituted alkyl, alkoxy, alkylamino, dialkylamino, alkylthio, alkenylthio or cycloalkylthio or represent in each case optionally substituted phenyl, benzyl, phenoxy or phenylthio,
$R^6$ and $R^7$ independently of one another represent hydrogen, represent in each case optionally halogen- or cyano-substituted alkyl, cycloalkyl, alkenyl, alkoxy, alkoxyalkyl, represent in each case optionally substituted phenyl or benzyl, or together with the nitrogen atom to which they are attached form an optionally substituted cycle which optionally contains oxygen or sulphur.

2. The compound of the formula (I) according to claim 1 in which
W represents hydrogen, $C_1$-$C_6$-alkyl, $C_2$-$C_6$-alkenyl, $C_2$-$C_6$-alkynyl, represents $C_3$-$C_6$-cycloalkyl which is optionally mono- or disubstituted by $C_1$-$C_2$-alkyl, $C_1$-$C_2$-alkoxy, fluorine, chlorine, trifluoromethyl or $C_3$-$C_6$-cycloalkyl, represents halogen, $C_1$-$C_6$-alkoxy, $C_1$-$C_4$-haloalkyl, $C_1$-$C_4$-haloalkoxy or cyano,
X represents halogen, $C_1$-$C_6$-alkyl, $C_2$-$C_6$-alkenyl, $C_2$-$C_6$-alkynyl, represents $C_3$-$C_6$-cycloalkyl which is optionally mono- or disubstituted by $C_1$-$C_2$-alkyl, $C_1$-$C_2$-alkoxy, fluorine, chlorine, trifluoromethyl or $C_3$-$C_6$-cycloalkyl, represents $C_1$-$C_6$-haloalkyl, $C_1$-$C_6$-alkoxy, $C_3$-$C_6$-alkenyloxy, $C_1$-$C_6$-alkylthio, $C_1$-$C_6$-alkylsulphinyl, $C_1$-$C_6$-alkylsulphonyl, $C_1$-$C_6$-haloalkoxy, $C_3$-$C_6$-haloalkenyloxy, nitro or cyano,
Y and Z independently of one another represent hydrogen, halogen, $C_1$-$C_6$-alkyl, $C_2$-$C_6$-alkenyl, $C_2$-$C_6$-alkynyl, represent $C_3$-$C_6$-cycloalkyl which is optionally mono- or disubstituted by $C_1$-$C_2$-alkyl, $C_1$-$C_2$-alkoxy, fluorine, chlorine, trifluoromethyl or $C_3$-$C_6$-cycloalkyl, represent $C_1$-$C_6$-alkoxy, $C_1$-$C_6$-haloalkyl, $C_1$-$C_6$-haloalkoxy, cyano, $C_2$-$C_6$-alkenyl, $C_2$-$C_6$-alkynyl or represent one of the (het)aryl radicals

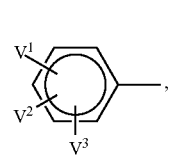
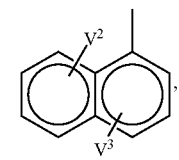
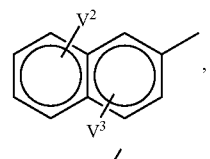
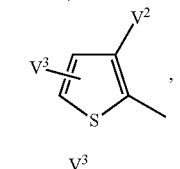
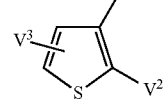
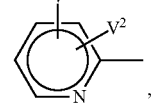

-continued

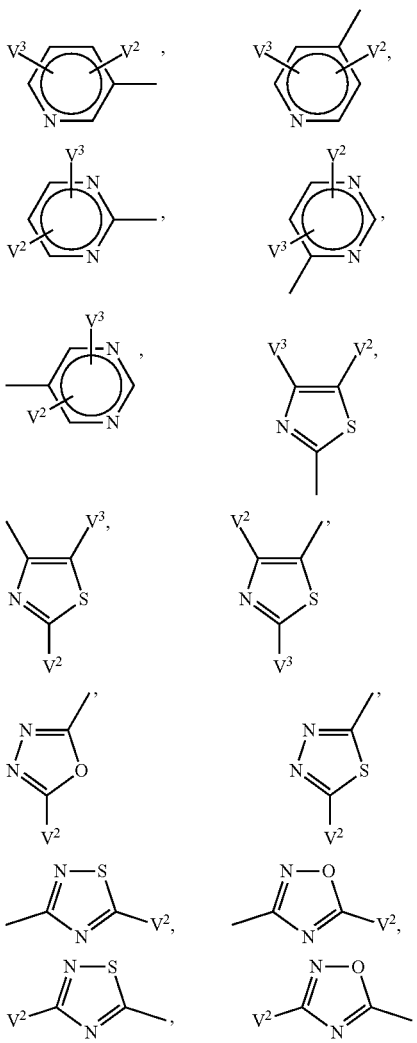

where in the case of (het)aryl only one of the radicals Y or Z may represent (het)aryl, $V^1$ represents hydrogen, halogen, $C_1$-$C_{12}$-alkyl, $C_1$-$C_6$-alkoxy, $C_1$-$C_6$-alkylthio, $C_1$-$C_6$-alkylsulphinyl, $C_1$-$C_6$-alkylsulphonyl, $C_1$-$C_4$-haloalkyl, $C_1$-$C_4$-haloalkoxy, nitro, cyano or represents phenyl, phenoxy, phenoxy-$C_1$-$C_4$-alkyl, phenyl-$C_1$-$C_4$-alkoxy, phenylthio-$C_1$-$C_4$-alkyl or phenyl-$C_1$-$C_4$-alkylthio, each of which is optionally mono- or polysubstituted by halogen, $C_1$-$C_6$-alkyl, $C_1$-$C_6$-alkoxy, $C_1$-$C_4$-haloalkyl, $C_1$-$C_4$-haloalkoxy, nitro or cyano, $V^2$ and $V^3$ independently of one another represent hydrogen, halogen, $C_1$-$C_6$-alkyl, $C_1$-$C_6$-alkoxy, $C_1$-$C_4$-haloalkyl or $C_1$-$C_4$-haloalkoxy, A and B and the carbon atom (4'-position) to which they are attached represent a tetrahydrofuran ring, which is optionally mono- or disubstituted by $C_1$-$C_6$-alkyl, $C_1$-$C_4$-haloalkyl, $C_1$-$C_6$-alkoxy or $C_1$-$C_4$-alkoxy-$C_1$-$C_4$-alkyl, D represents NH (1) or oxygen (2), $Q^1$ and $Q^2$ independently of one another represent hydrogen, $C_1$-$C_6$-alkyl, $C_1$-$C_2$-haloalkyl or $C_1$-$C_4$-alkoxy, G represents hydrogen (a) or represents one of the groups

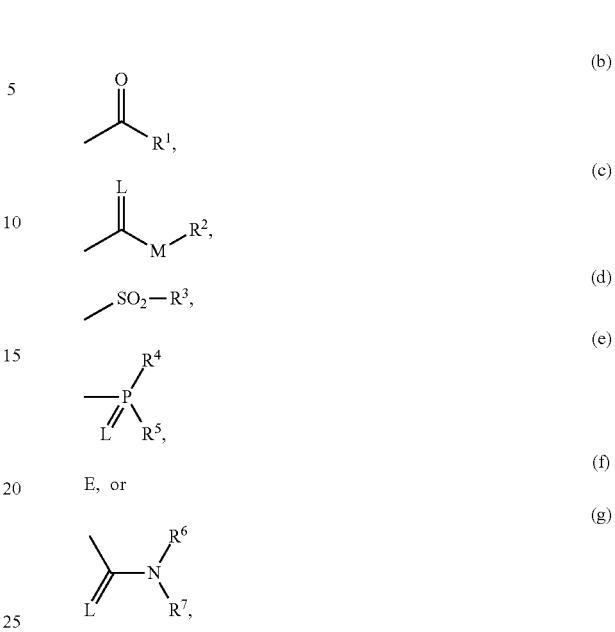

in which

E represents a metal ion or an ammonium ion,

L represents oxygen or sulphur and

M represents oxygen or sulphur, $R^1$ represents in each case optionally halogen- or cyano-substituted $C_1$-$C_{20}$-alkyl, $C_2$-$C_{20}$-alkenyl, $C_1$-$C_8$-alkoxy-$C_1$-$C_8$-alkyl, $C_1$-$C_8$-alkylthio-$C_1$-$C_8$-alkyl or poly-$C_1$-$C_8$-alkoxy-$C_1$-$C_8$-alkyl or represents optionally halogen-, $C_1$-$C_6$-alkyl- or $C_1$-$C_6$-alkoxy-substituted $C_3$-$C_8$-cycloalkyl in which optionally one or two not directly adjacent methylene groups are replaced by oxygen and/or sulphur, represents optionally halogen-, cyano-, nitro-, $C_1$-$C_6$-alkyl-, $C_1$-$C_6$-alkoxy-, $C_6$ haloalkyl-, $C_1$-$C_6$-haloalkoxy-, $C_1$-$C_6$-alkylthio- or $C_1$-$C_6$-alkylsulphonyl-substituted phenyl, represents optionally halogen-, nitro-, cyano-, $C_1$-$C_6$-alkyl-, $C_1$-$C_6$-alkoxy-, $C_1$-$C_6$-haloalkyl- or $C_1$-$C_6$-haloalkoxy-substituted phenyl-$C_1$-$C_6$-alkyl, represents optionally halogen- or $C_1$-$C_6$-alkyl-substituted 5- or 6-membered hetaryl having one or two heteroatoms from the group consisting of oxygen, sulphur and nitrogen, represents optionally halogen- or $C_1$-$C_6$-alkyl-substituted phenoxy-$C_1$-$C_6$-alkyl, or represents optionally halogen-, amino- or $C_1$-$C_6$-alkyl substituted 5- or 6-membered hetaryloxy-$C_1$-$C_6$-alkyl having one or two heteroatoms from the group consisting of oxygen, sulphur and nitrogen, $R^2$ represents in each case optionally halogen- or cyano-substituted alkyl, $C_2$-$C_{20}$-alkenyl, $C_1$-$C_8$-alkoxy-$C_2$-$C_8$-alkyl or poly-$C_1$-$C_8$-alkoxy-$C_2$-$C_8$-alkyl, represents optionally halogen-, $C_1$-$C_6$-alkyl- or $C_1$-$C_6$-alkoxy-substituted $C_3$-$C_8$-cycloalkyl, or represents in each case optionally halogen-, cyano-, nitro-, $C_1$-$C_6$-alkyl-, $C_1$-$C_6$-alkoxy-, $C_1$-$C_6$-haloalkyl- or $C_1$-$C_6$-haloalkoxy-substituted phenyl or benzyl, $R^3$ represents optionally halogen-substituted $C_1$-$C_8$-alkyl or in each case optionally halogen-, $C_1$-$C_6$-alkyl-, $C_1$-$C_6$-alkoxy-, $C_1$-$C_4$-haloalkyl-, $C_1$-$C_4$-haloalkoxy-, cyano- or nitro-substituted phenyl or benzyl, $R^4$ and $R^5$ independently of one another represent in each case optionally halogen-substituted $C_1$-$C_8$-alkyl, $C_1$-$C_8$-alkoxy, $C_1$-$C_8$-alkylamino, di-($C_1$-$C_8$-alkyl)amino, $C_1$-$C_8$-alkylthio or $C_3$-$C_8$-alkenylthio or represent in each case optionally halogen-, nitro-, cyano-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkyl- or $C_1$-$C_4$-haloalkyl-substituted phenyl, phenoxy or phenylthio, $R^6$ and $R^7$ independently of one another represent hydrogen, represent in each case optionally halogen- or cyano-substituted $C_1$-$C_8$-alkyl, $C_3$-$C_8$-cycloalkyl, $C_1$-$C_8$-alkoxy, $C_3$-$C_8$-alkenyl or $C_1$-$C_8$-alkoxy-$C_2$-$C_8$-alkyl, represent in each case optionally halogen-, $C_1$-$C_8$-alkyl-, $C_1$-$C_8$-haloalkyl- or $C_1$-$C_8$-alkoxy-substituted phenyl or benzyl or together represent an optionally $C_1$-$C_6$-alkyl-substituierten $C_3$-$C_6$-alkylene radical in which optionally one methylene group is replaced by oxygen or sulphur.

3. The compound of the formula (I) according to claim 1 in which

W represents hydrogen, chlorine, bromine, $C_1$-$C_4$-alkyl, $C_2$-$C_4$-alkenyl, $C_2$-$C_4$-alkynyl, represents $C_3$-$C_6$-cycloalkyl which is optionally monosubstituted by methyl, ethyl, methoxy, fluorine, chlorine, trifluoromethyl or cyclopropyl, represents $C_1$-$C_4$-alkoxy, $C_1$-$C_2$-haloalkyl or $C_1$-$C_2$-haloalkoxy, X represents chlorine, bromine, $C_1$-$C_4$-alkyl, $C_2$-$C_4$-alkenyl, $C_2$-$C_4$-alkynyl, represents $C_3$-$C_6$-cycloalkyl which is optionally monosubstituted by methyl, ethyl, methoxy, fluorine, chlorine, trifluoromethyl or cyclopropyl, represents $C_1$-$C_4$-alkoxy, $C_1$-$C_4$-haloalkyl, $C_1$-$C_4$-haloalkoxy or cyano, Y and Z independently of one another represent hydrogen, fluorine, chlorine, bromine, iodine, $C_1$-$C_4$-alkyl, $C_2$-$C_4$-alkenyl, $C_2$-$C_4$-alkynyl, represent $C_3$-$C_6$-cycloalkyl which is optionally monosubstituted by methyl, ethyl, methoxy, fluorine, chlorine, trifluoromethyl or cyclopropyl, represent $C_1$-$C_6$-alkoxy, $C_1$-$C_4$-haloalkyl, $C_1$-$C_4$-haloalkoxy, cyano, $C_2$-$C_4$-alkenyl, $C_2$-$C_4$-alkynyl or represent one of the (het)aryl radicals

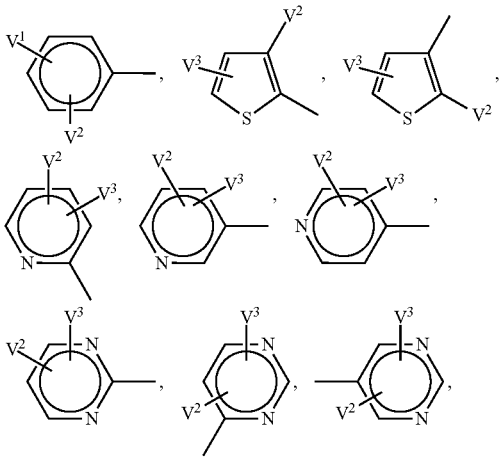

where in the case of (het)aryl only one of the radicals Y or Z may represent (het)aryl, $V^1$ represents hydrogen, fluorine, chlorine, bromine, $C_1$-$C_6$-alkyl, $C_1$-$C_4$-alkoxy, $C_1$-$C_2$-haloalkyl, $C_1$-$C_2$-haloalkoxy, nitro, cyano or represents phenyl which is optionally mono- or disubstituted by fluorine, chlorine, bromine, $C_1$-$C_4$-alkyl, $C_1$-$C_4$-alkoxy, $C_1$-$C_2$-haloalkyl, $C_1$-$C_2$-haloalkoxy, nitro or cyano, $V^2$ and $V^3$ independently of one another represent hydrogen, fluorine, chlorine, bromine, $C_1$-$C_4$-alkyl, $C_1$-$C_4$-alkoxy, $C_1$-$C_2$-haloalkyl or $C_1$-$C_2$-haloalkoxy, A and B and the carbon atom (4'-position) to which they are attached represent a tetrahydrofuran ring, which is optionally monosubstituted by $C_1$-$C_4$-alkyl, $C_1$-$C_3$-haloalkyl, $C_1$-$C_4$-alkoxy or $C_1$-$C_4$-alkoxy-$C_1$-$C_2$-alkyl, D represents NH (1) or oxygen (2), $Q^1$ and $Q^2$ independently of one another represent hydrogen, methyl, ethyl, trifluoromethyl, methoxy or ethoxy, G represents hydrogen (a) or represents one of the groups

(b)

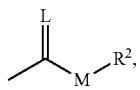

(c)

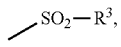

(d)

(e)

E, or (f)

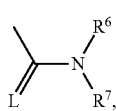

(g)

in which

E represents a metal ion or an ammonium ion,

L represents oxygen or sulphur and

M represents oxygen or sulphur, $R^1$ represents $C_1$-$C_{16}$-alkyl, $C_2$-$C_{16}$-alkenyl, $C_1$-$C_6$-alkoxy-$C_1$-$C_4$-alkyl, $C_1$-$C_6$-alkylthio-$C_1$-$C_4$-alkyl or poly-$C_1$-$C_6$-alkoxy-$C_1$-$C_4$-alkyl, each of which is optionally mono- to trisubstituted by fluorine or chlorine, or represents $C_3$-$C_7$-cycloalkyl which is optionally mono- or disubstituted by fluorine, chlorine, $C_1$-$C_5$-alkyl or $C_1$-$C_5$-alkoxy and in which optionally one or two not directly adjacent methylene groups are replaced by oxygen and/or sulphur, represents phenyl which is optionally mono- to trisubstituted by fluorine, chlorine, bromine, cyano, nitro, $C_1$-$C_4$-alkyl, $C_1$-$C_4$-alkoxy, $C_1$-$C_3$-haloalkyl, $C_1$-$C_3$-haloalkoxy, $C_1$-$C_4$-alkylthio or $C_1$-$C_4$-alkylsulphonyl, represents phenyl-$C_1$-$C_4$-alkyl which is optionally mono- or disubstituted by fluorine, chlorine, bromine, $C_1$-$C_4$-alkyl, $C_1$-$C_4$-alkoxy, $C_1$-$C_3$-haloalkyl or $C_1$-$C_3$-haloalkoxy, represents pyrazolyl, thiazolyl, pyridyl, pyrimidyl, furanyl or thienyl, each of which is optionally mono- or disubstituted by fluorine, chlorine, bromine or $C_1$-$C_4$-alkyl, represents phenoxy-$C_1$-$C_5$-alkyl which is optionally mono- or disubstituted by fluorine, chlorine, bromine or $C_1$-$C_4$-alkyl, or represents pyridyloxy-$C_1$-$C_5$-alkyl, pyrimidyloxy-$C_1$-$C_5$-alkyl or thiazolyloxy-$C_1$-$C_5$-alkyl, each of which is optionally mono- or disubstituted by fluorine, chlorine, bromine, amino or $C_1$-$C_4$-alkyl, $R^2$ represents $C_1$-$C_{16}$-alkyl, $C_2$-$C_{16}$-alkenyl, $C_1$-$C_6$-alkoxy-$C_2$-$C_6$-alkyl or poly-$C_1$-$C_6$-alkoxy-$C_2$-$C_6$-alkyl, each of which is optionally mono- to trisubstituted by fluorine or chlorine, represents $C_3$-$C_7$-cycloalkyl which is optionally mono- or disubstituted by fluorine, chlorine, $C_1$-$C_4$-alkyl or $C_1$-$C_4$-alkoxy, or represents phenyl or benzyl, each of which is optionally mono- to trisubstituted by fluorine, chlorine, bromine, cyano, nitro, $C_1$-$C_4$-alkyl, $C_1$-$C_3$-alkoxy, $C_1$-$C_3$-haloalkyl or $C_1$-$C_3$-haloalkoxy, $R^3$ represents $C_1$-$C_6$-alkyl which is optionally mono- to trisubstituted by fluorine or chlorine or represents phenyl or benzyl, each of which is optionally mono- or disubstituted by fluorine, chlorine, bromine, $C_1$-$C_1$-alkyl, $C_1$-$C_4$alkoxy, $C_1$-$C_2$-haloalkoxy, cyano or nitro, $R^4$ and $R^5$ independently of one another represent $C_1$-$C_6$-alkyl, $C_1$-$C_6$-alkoxy, $C_1$-$C_6$-alkylamino, di-($C_1$-$C_6$-alkyl)amino, $C_1$-$C_6$-alkylthio or $C_3$-$C_4$-alkenylthio, each of which is optionally mono- to trisubstituted by fluorine or chlorine, or represent phenyl, phenoxy or phenylthio, each of which is optionally mono- or disubstituted by fluorine, chlorine, bromine, nitro, cyano, $C_1$-$C_3$-alkoxy, $C_1$-$C_3$-haloalkoxy, $C_1$-$C_3$-alkylthio, $C_1$-$C_3$-haloalkylthio, $C_1$-$C_3$-alkyl or $C_1$-$C_3$-haloalkyl, $R^6$ and $R^7$ independently of one another represent hydrogen, represent $C_1$-$C_6$-alkyl, $C_3$-$C_6$-cycloalkyl, $C_1$-$C_6$-alkoxy, $C_3$-$C_6$-alkenyl or $C_1$-$C_6$-alkoxy-$C_2$-$C_6$-alkyl, each of which is optionally mono- to trisubstituted by fluorine or chlorine, represent phenyl or benzyl, each of which is optionally mono- to trisubstituted by fluorine, chlorine, bromine, $C_1$-$C_5$-haloalkyl, $C_1$-$C_5$-alkyl or $C_1$-$C_5$-alkoxy, or together represent an optionally $C_1$-$C_4$-alkyl-substituted $C_3$-$C_6$-alkylene radical in which optionally one methylene group is replaced by oxygen or sulphur.

4. The compound of the formula (I) according to claim 1 in which

W represents hydrogen, chlorine, bromine, methyl, ethyl, vinyl, ethynyl, propynyl, cyclopropyl, methoxy, ethoxy or trifluoromethyl, X represents chlorine, bromine, methyl, ethyl, propyl, isopropyl, vinyl, ethynyl, propynyl, cyclopropyl, methoxy, ethoxy, trifluoromethyl, difluoromethoxy, trifluoromethoxy or cyano, Y and Z independently of one another represent hydrogen, fluorine, chlorine, bromine, iodine, methyl, ethyl, vinyl, ethynyl, propynyl, cyclopropyl, methoxy, trifluoromethyl, trifluoromethoxy, cyano or a phenyl radical,

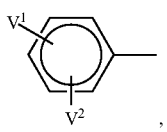

where in the case of phenyl only one of the radicals Y or Z may represent phenyl, $V^1$ represents hydrogen, fluorine, chlorine, bromine, methyl, ethyl, n-propyl, isopropyl, tert-butyl, methoxy, ethoxy, n-propoxy, isopropoxy, trifluoromethyl or trifluoromethoxy, $V^2$ represents hydrogen, fluorine, chlorine, methyl, ethyl, n-propyl, isopropyl, methoxy, ethoxy or trifluoromethyl, A and B and the carbon atom (4'-position) to which they are attached represent a tetrahydrofuran ring, which is optionally monosubstituted by methyl, ethyl, propyl, trifluoromethyl, methoxy, ethoxy, methoxymethyl or ethoxymethyl, D represents NH (1) or oxygen (2), $Q^1$ and $Q^2$ represent hydrogen, G represents hydrogen (a) or represents one of the groups

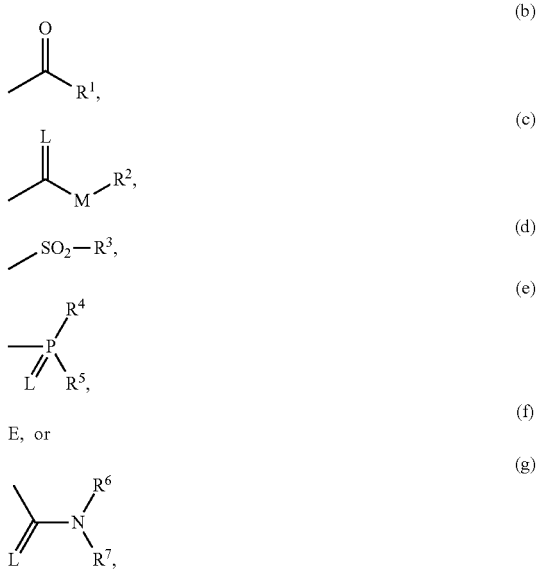

in which

E represents a metal ion or an ammonium ion,

L represents oxygen or sulphur and

M represents oxygen or sulphur, $R^1$ represents $C_1$-$C_{10}$-alkyl, $C_2$-$C_{10}$-alkenyl, $C_1$-$C_4$-alkoxy-$C_1$-$C_2$-alkyl, alkylthio-$C_1$-$C_2$-alkyl, each of which is optionally mono- to trisubstituted by fluorine or chlorine, or represents $C_3$-$C_6$-cycloalkyl which is optionally monosubstituted by fluorine, chlorine, methyl, ethyl or methoxy, represents phenyl which is optionally mono- or disubstituted by fluorine, chlorine, bromine, cyano, nitro, methyl, ethyl, n-propyl, isopropyl, methoxy, ethoxy, trifluoromethyl or trifluoromethoxy, or represents furanyl, thienyl or pyridyl, each of which is optionally monosubstituted by chlorine, bromine or methyl, $R^2$ represents $C_1$-$C_{10}$-alkyl, $C_2$-$C_{10}$-alkenyl or $C_1$-$C_4$-alkoxy-$C_2$-$C_4$-alkyl, each of which is optionally mono- to trisubstituted by fluorine or chlorine, represents cyclopentyl or cyclohexyl, or represents phenyl or benzyl, each of which is optionally mono- or disubstituted by fluorine, chlorine, cyano, nitro, methyl, ethyl, methoxy, trifluoromethyl or trifluoromethoxy, $R^3$ represents methyl, ethyl, propyl or isopropyl, each of which is optionally mono- to trisubstituted by fluorine or chlorine, or represents phenyl which is optionally monosubstituted by fluorine, chlorine, bromine, methyl, ethyl, isopropyl, tert-butyl, methoxy, ethoxy, isopropoxy, trifluoromethyl, trifluoromethoxy, cyano or nitro, R⁴ and R⁵ independently of one another represent $C_1$-$C_4$-alkoxy or $C_1$-$C_4$-alkylthio or represent phenyl, phenoxy or phenylthio, each of which is optionally monosubstituted by fluorine, chlorine, bromine, nitro, cyano, methyl, methoxy, trifluoromethyl or trifluoromethoxy, R⁶ and R⁷ independently of one another represent hydrogen, represent $C_1$-$C_4$-alkyl, $C_3$-$C_6$-cycloalkyl, $C_1$-$C_4$-alkoxy, $C_3$-$C_4$-alkenyl or $C_1$-$C_4$-alkoxy-$C_2$-$C_4$-alkyl, represent phenyl which is optionally mono- or disubstituted by fluorine, chlorine, bromine, methyl, methoxy or trifluoromethyl, or together represent a $C_8$-$C_6$-alkylene radical in which optionally one methylene group is replaced by oxygen or sulphur.

5. The compound of the formula (I) according to claim 1, in which

W represents hydrogen, chlorine, bromine, methyl, ethyl or methoxy,

X represents chlorine, bromine, methyl, ethyl or methoxy,

Y and Z independently of one another represent hydrogen, chlorine, bromine, methyl or represent the radical

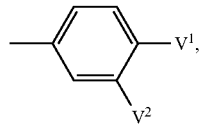

where in this case only one of the radicals Y or Z may represent

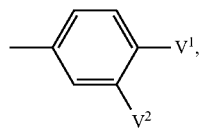

V¹ represents fluorine or chlorine,
V² represents hydrogen, fluorine or chlorine,
A and B and the carbon atom (4'-position) to which they are attached represent a tetrahydrofuran ring which is optionally monosubstituted by methyl, ethyl, propyl or methoxymethyl,
D represents NH (1) or oxygen (2),
Q¹ and Q² represent hydrogen,
G represents hydrogen (a) or represents one of the groups

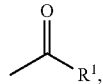 (b)

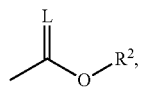 (c)

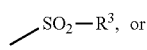 (d)

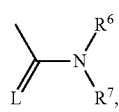 (g)

R¹ represents $C_1$-$C_{10}$-alkyl, $C_1$-$C_4$-alkoxy-$C_1$-$C_2$-alkyl, $C_3$-$C_6$-cycloalkyl, or represents phenyl which is optionally monosubstituted by chlorine, or represents thienyl, R² represents $C_1$-$C_{10}$-alkyl, $C_2$-$C_{10}$-alkenyl, or represents benzyl, R³ represents methyl, R⁶ and R⁷ together represent a $C_5$-$C_6$-alkylene radical in which optionally one methylene group is replaced by oxygen or sulphur.

6. The compound of the formula (I) according to claim 1 in which

W represents hydrogen, chlorine, bromine, methyl or ethyl,

X represents chlorine, bromine, methyl, ethyl, methoxy, ethoxy or cyclopropyl,

Y represents hydrogen, methyl, ethyl, chlorine, bromine, iodine, fluorine, trifluoromethoxy or cyclopropyl, Z represents hydrogen, bromine, methyl or the radicals

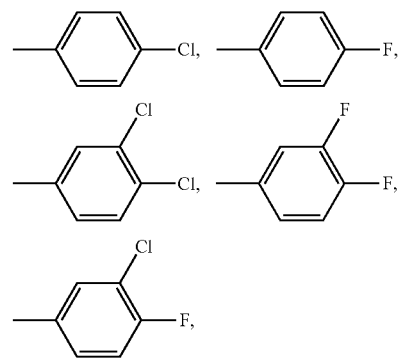

A and B and the carbon atom (4'-position) to which they are attached represent

wherein "*" indicates the carbon atom at 4'-position,

D represents NH (1) or oxygen (2),

Q¹ and Q² represent hydrogen,

G represents hydrogen (a) or one of the groups

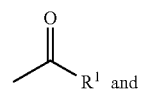 (b)

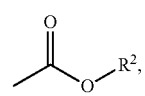 (c)

R¹ represents $C_1$-$C_6$-alkyl, $C_1$-$C_4$-alkoxy-$C_1$-$C_2$-alkyl or cyclopropyl, R² represents $C_1$-$C_6$-alkyl or benzyl.

7. Process for preparing compounds of the formula (I) according to claim 1, characterized in that, to obtain
(A) compounds of the formula (I-1-a)

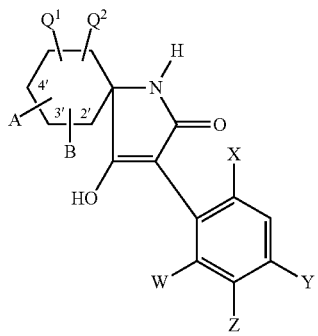
(I-1-a)

in which
A, B, $Q^1$, $Q^2$, W, X, Y and Z have the meanings given above,
compounds of the formula (II)

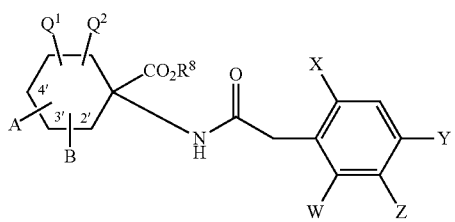
(II)

in which
A, B, $Q^1$, $Q^2$, W, X, Y and Z have the meanings given above and
$R^8$ represents alkyl
are condensed intramolecularly in the present of a diluent and in the presence of a base,
(B) compounds of the formula (I-2-a)

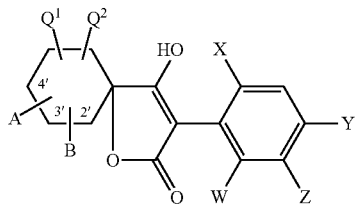
(I-2-a)

in which
A, B, $Q^1$, $Q^2$, W, X, Y and Z have the meanings given above,
compounds of the formula (III)

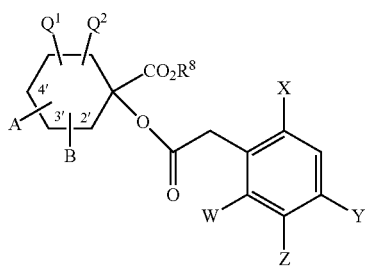
(III)

in which
A, B, $Q^1$, $Q^2$, W, X, Y, Z and $R^8$ have the meanings given above
are condensed intramolecularly in the presence of a diluent and in the presence of a base,
(C) compounds of the formulae (I-1-b) to (I-2-b) shown above in which $R^1$, A, B, $Q^1$, $Q^2$, W, X, Y and Z have the meanings given above,
compounds of the formulae (I-1-a) to (I-2-a) shown above in which A, B, $Q^1$, $Q^2$, W, X, Y and Z have the meanings given above are in each case reacted
α) with compounds of the formula (IV)

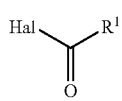
(IV)

in which
$R^1$ has the meaning given above and
Hal represents halogen
or
β) with carboxylic anhydrides of the formula (V)

$$R^1\text{—CO—O—CO—}R^1 \quad (V)$$

in which
$R^1$ has the meaning given above,
if appropriate in the presence of a diluent and if appropriate in the presence of an acid binder;
(D) compounds of the formulae (I-1-c) to (I-2-c) shown above in which $R^2$, A, B, $Q^1$, $Q^2$, M, W, X, Y and Z have the meanings given above and L represents oxygen, compounds of the formulae (I-1-a) to (I-2-a) shown above in which A, B, $Q^1$, $Q^2$, W, X, Y and Z have the meanings given above are in each case reacted
with chloroformic esters or chloroformic thioesters of the formula (VI)

$$R^2\text{-M-CO—Cl} \quad (VI)$$

in which
$R^2$ and M have the meanings given above,
if appropriate in the presence of a diluent and if appropriate in the presence of an acid binder;
(E) compounds of the formulae (I-1-c) to (I-2-c) shown above in which $R^2$, A, B, $Q^1$, $Q^2$, M, W, X, Y and Z have the meanings given above and L represents sulphur, compounds of the formulae (I-1-a) to (I-2-a) shown above in which A, B, $Q^1$, $Q^2$, W, X, Y and Z have the meanings given above are in each case reacted
with chloromonothioformic esters or chlorodithioformic esters of the formula (VII)

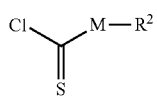
(VII)

in which
M and $R^2$ have the meanings given above,
if appropriate in the presence of a diluent and if appropriate in the presence of an acid binder,
(F) compounds of the formulae (I-1-d) to (I-2-d) shown above in which $R^3$, A, B, $Q^1$, $Q^2$, W, X, Y and Z have the meanings given above, compounds of the formulae (I-1-a) to (I-2-a) shown above in which A, B, $Q^1$, $Q^2$, W, X, Y and Z have the meanings given above are in each case reacted with sulphonyl chlorides of the formula (VIII)

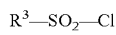  (VIII)

in which
R³ has the meaning given above,
if appropriate in the presence of a diluent and if appropriate in the presence of an acid binder,
(G) compounds of the formulae (I-1-e) to (I-2-e) shown above in which L, R⁴, R⁵, A, B, Q¹, Q², W, X, Y and Z have the meanings given above, compounds of the formulae (I-1-a) to (I-2-a) shown above in which A, B, Q¹, Q², W, X, Y and Z have the meanings given above are in each case reacted
with phosphorus compounds of the formula (IX)

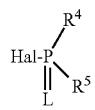  (IX)

in which
L, R⁴ and R⁵ have the meanings given above and
Hal represents halogen,
if appropriate in the presence of a diluent and if appropriate in the presence of an acid binder,
(H) compounds of the formulae (I-1-0 to (I-24) shown above in which E, A, B, Q¹, Q², W, X, Y and Z have the meanings given above, compounds of the formulae (I-1-a) to (I-2-a) in which A, B, Q¹, Q², W, X, Y and Z have the meanings given above are in each case reacted
with metal compounds or amines of the formulae (X) and (XI), respectively,

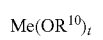  (X)

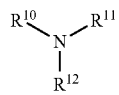  (XI)

in which
Me represents a mono- or divalent metal,
t represents the number 1 or 2 and
R¹⁰, R¹¹, R¹² independently of one another represent hydrogen or alkyl,
if appropriate in the presence of a diluent,
(I) compounds of the formulae (I-1-g) to (I-2-g) shown above in which L, R⁶, R⁷, A, B, Q¹, Q², W, X, Y and Z have the meanings given above, compounds of the formulae (I-1-a) to (I-2-a) shown above in which A, B, Q¹, Q², W, X, Y and Z have the meanings given above are in each case reacted
α) with isocyanates or isothiocyanates of the formula (XII)

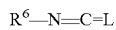  (XII)

in which
R⁶ and L have the meanings given above,
if appropriate in the presence of a diluent and if appropriate in the presence of a catalyst, or β) with carbamoyl chlorides or thiocarbamoyl chlorides of the formula (XIII)

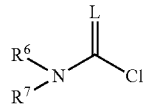  (XIII)

in which
L, R⁶ and R⁷ have the meanings given above,
if appropriate in the presence of a diluent and if appropriate in the presence of an acid binder,
(Jα) compounds of the formulae (I-1a) to (I-2-g) shown above in which A, B, D, G, Q¹, Q², W, X, Y and Z have the meaning given above, compounds of the formulae (I-1-a') to (I-2-g') in which A, B, D, G, Q¹, Q², W, X and Y have the meaning given above and Z' represents bromine or iodine

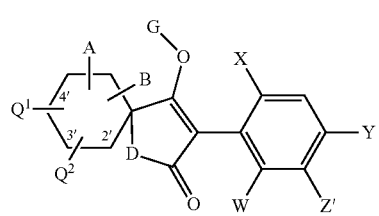  (I-1-a' to I-2-g')

and
(Jβ) compounds of the formulae (I-1-a) to (I-2-g) shown above in which A, B, D, G, Q¹, Q², W, X, Y and Z have the meaning given above, compounds of the formulae (I-1-a") to (I-2-g") in which A, B, D, G, Q¹, Q², W, X and Z have the meaning given above and Y' represents bromine or iodine

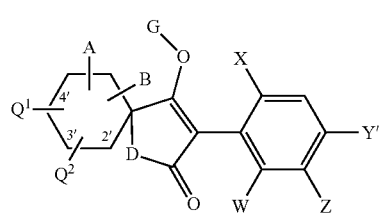  (I-1-a" to I-2-g")

are coupled with (het)aryl derivatives capable of coupling of the formulae (XVα) and (XVβ), respectively,

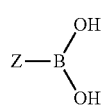  (XVα)

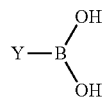  (XVβ)

or esters thereof in the presence of a solvent, in the presence of a catalyst and in the presence of a base.

8. A composition for controlling pests and/or unwanted vegetation, comprising at least one compound of the formula (I) according to claim 1.

9. A method for controlling animal pests and/or unwanted vegetation, comprising applying at least one compound of the formula (I) according to claim 1 to the pests, unwanted vegetation and/or their habitat.

10. A process for preparing a composition for controlling pests and/or unwanted vegetation, comprising mixing at least one compound of the formula (I) according to claim 1 with extenders and/or surfactants.

11. A method for controlling pests and/or unwanted vegetation, comprising applying the composition according to claim 8 to the pests, unwanted vegetation and/or their habitat.

* * * * *